United States Patent [19]

Takase et al.

[11] Patent Number: 6,110,933
[45] Date of Patent: *Aug. 29, 2000

[54] AMINO ACID DERIVATIVES AND THEIR USE AS PHOSPHOLIPASE $A_2$ INHIBITOR

[75] Inventors: Shigehiro Takase, Ishioka; Nobuharu Shigematsu; Seiji Yoshimura, both of Tsukuba; Satoshi Okada, Kyoto; Keiji Hemmi, deceased, late of Tsukuba, by Mitsue Hemmi, heir; Hirokazu Tanaka, Takarazuka; Takanao Otsuka; Yasuhisa Tsurumi, both of Tsukuba; Masanori Okamoto, Osaka; Masakuni Okuhara, Tsukuba; Naoki Fukami, Ibaraki, all of Japan

[73] Assignee: Fujisawa Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/669,395

[22] PCT Filed: Jan. 23, 1995

[86] PCT No.: PCT/JP95/00068

§ 371 Date: Nov. 12, 1996

§ 102(e) Date: Nov. 12, 1996

[87] PCT Pub. No.: WO95/19959

PCT Pub. Date: Jul. 27, 1995

[30] Foreign Application Priority Data

Jan. 24, 1994 [GB] United Kingdom .................. 9401268
Oct. 31, 1994 [GB] United Kingdom .................. 9421962

[51] Int. Cl.[7] .................. A61K 31/325; A61K 31/16; C07D 217/00; C07D 215/02
[52] U.S. Cl. .................. 514/307; 514/311; 514/277; 514/299; 514/279; 546/139; 546/151; 546/152; 546/164; 540/166; 540/174; 540/175
[58] Field of Search .................. 546/139, 152, 546/146, 151, 164, 166, 174, 175; 514/307, 311

[56] References Cited

FOREIGN PATENT DOCUMENTS 0336356 10/1989 European Pat. Off. .
92/17452 10/1992 WIPO .

OTHER PUBLICATIONS

Lettieri et al., Boll. Chim. Farm. (1981), 120 (5), pp. 308–310.
Ahmad et al., J. Indian Chem. Soc., Dec. (1979), vol. LVI (12), pp. 1265–1268.
Donia S. G., Pak. J. Sci. ind. res., Oct. (1992), vol. 35, No. 10, pp. 388–390, 1990.
Bhat et al., Ind. J. Chem. Sect. B, (1981)vol. 20 B (4), pp. 331–333.
Jouln et al., Tetrahederon Letters, (1987), vol. 28, No. 15, pp. 1665–1668.
Hanabusa et al., J. Macromol. Sci–Chem.,(1989) A26(12), pp. 1571–1584.
Cantacuzene et al., Tetrahederon, 1989, vol. 45, No. 3, pp. 741–745.
Ichikawa et al., Chemical abstracts No. 116:6968g, EP 443,592, 1991.
Mendes et al. (CA 113:6315 abstract of EP 346208) 1989.

*Primary Examiner*—Shelley A. Dodson
*Assistant Examiner*—Sabiha N. Qazi
*Attorney, Agent, or Firm*—Oblon, Spivak, McClelland, Maier & Neustadt, P.C.

[57] ABSTRACT

The present invention relates to a novel fatty acid derivative of the following formula:

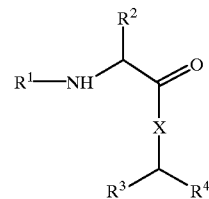

wherein
$R^1$ is acyl group, etc.;
$R^2$ is acyl(lower)alkyl;
$R^3$ is lower alkyl, etc.;
$R^4$ is hydrogen, etc.; and
X is —O—, etc;
and a pharmaceutically acceptable salt thereof, which is useful as a medicament; the processes for the preparation of said fatty acid derivative or a salt thereof; a pharmaceutical composition comprising said fatty acid derivative or a pharmaceutically acceptable salt thereof; etc.

12 Claims, No Drawings

AMINO ACID DERIVATIVES AND THEIR USE AS PHOSPHOLIPASE A₂ INHIBITOR

This application is a 371 of PCT/JP95/00068 filed Jan. 23, 1995.

TECHNICAL FIELD

The present invention relates to a novel fatty acid derivative and a pharmaceutically acceptable salt thereof which are useful as a medicament.

BACKGROUND ART

A phospholipase $A_2$ inhibitor having the structure of that of the present invention has not been known.

DISCLOSURE OF INVENTION

The present invention relates to novel fatty acid derivative and a pharmaceutically acceptable salt thereof, which are phospholipase $A_2$ inhibitors and are useful for the prevention and/or the treatment of pancreatitis, hepatitis, chronic renal failure, etc; shock (e.g. endotoxin shock, gram-negative septic shock, etc), arthritis (e.g. rheumatoid arthritis, osteoarthritis, etc), respiratory disease (e.g. bronchial asthma, bronchitis, adult respiratory distress syndrome, etc), heart disease (e.g. myocardial ischemia, etc), allergic disease, thrombosis, arteriosclerosis, pain, autoimmune disease, dermal disease (e.g. atopic dermatitis, psoriasis, contact dermatitis, etc), inflammatory bowel disease (e.g. Crohn's disease, ulcerative colitis, etc), ophthalmic disease (e.g. allergic ophthalmic disease, inflammatory ophthalmic disease, etc), nasal diseases (e.g. allergic rhinitis, etc), gout, trauma induced inflammation (e.g. spinal cord injury, etc), liver diseases (e.g. cirrhosis, hepatitis, etc), or the like; to a process for preparation thereof, to a pharmaceutical composition comprising the same, and to a method for using the same therapeutically in human being and animals for the prevention and/or treatment of the aforesaid diseases.

The object fatty acid derivative can be represented by the following formula (I):

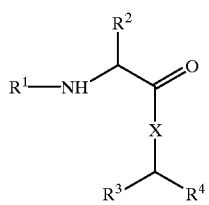

(I)

wherein
$R^1$ is acyl group or lower aliphatic hydrocarbon group which may have one or more suitable substituent(s),
$R^2$ is acyl(lower)alkyl,
$R^3$ is lower alkyl or higher alkyl,
$R^4$ is hydrogen, acyl group, acyl(lower)alkyl, or cyano(lower)alkyl, and

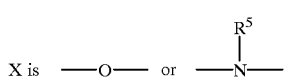

[wherein $R^5$ is hydrogen or acyl(lower)alkyl].

It is to be noted the object compound (I) may include one or more stereoisomers due to asymmetric carbon atom(s) and double bond, and all of such isomers and a mixture thereof are included within the scope of the present invention.

It is further to be noted isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc) and any form of the crystal of the compound (I) are included within the scope of the present invention.

The object compound (I) or a salt thereof can be prepared according to the following reaction schemes.

Process 1

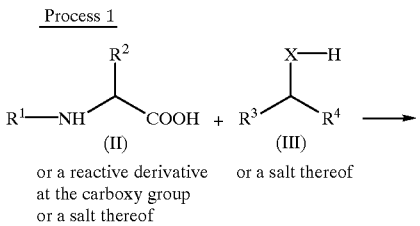

or a reactive derivative at the carboxy group or a salt thereof or a salt thereof

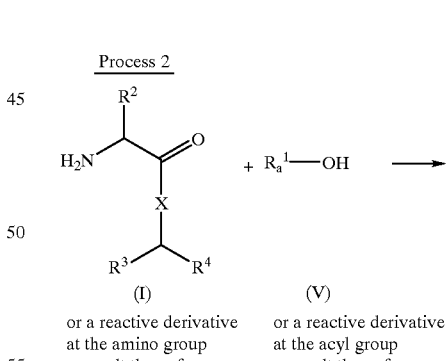

(I)
or a salt thereof

Process 2

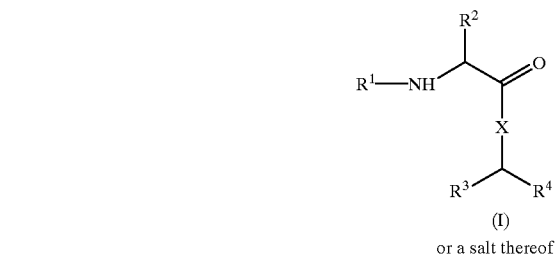

(I)
or a reactive derivative at the amino group or a salt thereof (V)
or a reactive derivative at the acyl group or a salt thereof

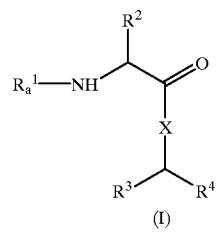

(I)
or a salt thereof

Process 3

[Structure (VI) or a salt thereof] →(amidating agent)→ [Structure (Ia) or a salt thereof]

Process 4

[Structure (Ib) or a salt thereof] →(elimination reaction of carboxy protective group)→ [Structure (Ic) or a salt thereof]

Process 5

[Structure (IV) or a reactive derivative at the amino group or a salt thereof] →(lower aliphatic hydrocarbon compound substituted with oxo which may have one or more suitable substituent(s) in the presence of a reducing agent)→ [Structure (Id) or a salt thereof]

Process 6

[Structure (Ie) or a salt thereof] →(amidating agent)→ [Structure (If) or a salt thereof]

Process 7

[Structure (VII) or a salt thereof] →(amidating agent)→ [Structure (Ia) or a salt thereof]

wherein $R^1$, $R^2$, $R^3$, $R^4$ and X are each as defined above, $R_a^1$ is acyl group, $R_b^1$ is amidated carboxy, $R_c^1$ is lower aliphatic hydrocarbon group which may have one or more suitable substituent(s), $R_a^2$ is protected carboxy(lower)alkyl, $R_b^2$ is carboxy(lower)alkyl, $R_a^4$ is carboxy or carboxy(lower)alkyl, $R_b^4$ is amidated carboxy or amidated carboxy(lower)alkyl, and Y is a leaving group.

Suitable pharmaceutically acceptable salts of the object compound (I) are conventional ones and include a metal salt such as an alkali metal salt (e.g. sodium salt, potassium salt, etc) and an alkaline earth metal salt (e.g. calcium salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumarate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "lower aliphatic hydrocarbon group" in the term "lower aliphatic hydrocarbon group which may have one or more suitable substituent(s)" may include lower alkyl, lower alkenyl and lower alkynyl.

Suitable example of "lower alkyl" may include straight or branched one such as methyl, ethyl, propyl, isopropyl, butyl, t-butyl, pentyl, hexyl or the like, in which the preferred one may be $(C_1-C_4)$alkyl.

Suitable example of "lower alkenyl" may include straight or branched ones having 2 to 6 carbon atoms such as vinyl, allyl, 2-propenyl, 1,3-butadienyl, 3-methyl-2-butenyl, 4-pentenyl, 2-hexenyl, or the like, in which the preferred one may be $(C_2-C_4)$alkenyl.

Suitable example of "lower alkynyl" may include straight or branched ones having 2 to 6 carbon atoms such as ethynyl, 2-propynyl, 1,3-butadiynyl, 3-methyl-2-butynyl, 4-pentynyl, 2-hexynyl, or the like, in which the preferred one may be $(C_2-C_4)$alkynyl.

Said "lower aliphatic hydrocarbon group" may have one or more (preferably 1 to 3) suitable substituent(s) such as acyl group, heterocyclic group, acylamino, heterocyclicamino, heterocyclic(lower)alkylamino, or the like, in which the preferred substituent may be heterocyclic group, the more preferred one may be unsaturated 3 to 8-membered heteromonocyclic group containing 1 to 4 nitrogen atom(s), and the most preferred one may be pyridyl.

Suitable "lower aliphatic hydrocarbon compound" moiety in the term "lower aliphatic hydrocarbon compound substituted with oxo" may be the corresponding hydrocarbon compound to the ones as exemplified for "lower aliphatic hydrocarbon group", and this "lower aliphatic hydrocarbon compound substituted with oxo" may have one or more (preferably 1 to 3) suitable substituent(s) as exemplified for those of "lower aliphatic hydrocarbon group".

Suitable "higher alkyl" may include straight or branched ones such as heptyl, 2-methylheptyl, octyl, nonyl, decyl, undecyl, dodecyl, tridecyl, 11-methyldodecyl, 12-methyltridecyl, tetradecyl, pentadecyl, hexadecyl, heptadecyl, octadecyl, nonadecyl, icosyl or the like, in which the preferred one may be $(C_7-C_{16})$alkyl, and the more preferred one may be heptyl, nonyl, undecyl, dodecyl, 11-methyldodecyl, tridecyl or 12-methyltridecyl.

Suitable "acyl group" may be aliphatic acyl, aromatic acyl, heterocyclic acyl, arylaliphatic acyl and heterocyclicaliphatic acyl derived from carboxylic acid, carbonic acid, carbamic acid, sulfonic acid, and the like.

Suitable example of the "acyl group" thus explained may be:

(1) lower alkanoyl [e.g. formyl, acetyl, propionyl, butyryl, isobutyryl, valeryl, hexanoyl, pivaloyl, etc] which may have one or more (preferably 1 to 3) suitable substituent (s) such as halogen (e.g. fluoro, chloro, bromo, iodo); hydroxy; lower alkoxy (e.g. methoxy, ethoxy, propoxy, butoxy, t-butoxy, pentyloxy, hexyloxy, etc); amino; protected amino, preferably, acylamino such as lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc); or the like; di(lower)alkylamino (e.g. dimethylamino, N-methylethylamino, diethylamino, N-propylbutylamino, dipentylamino, dihexylamino, etc); lower alkoxyimino (e.g. methoxyimino, ethoxyimino, propoxyimino, butoxyimino, t-butoxyimino, pentyloxyimino, hexyloxyimino, etc); ar(lower)alkoxyimino such as phenyl(lower)alkoxyimino (e.g. benzyloxyimino, phenethyloxyimino, benzhydryloxyimino, etc); or the like;

(2) higher alkanoyl [e.g. heptanoyl, octanoyl, nonanoyl, decanoyl, undecanoyl, lauroyl, tridecanoyl, myristoyl, pentadecanoyl, palmitoyl, 14-methylpentadecanoyl, 15-methylhexadecanoyl, 10,12-dimethyltetradecanoyl, heptadecanoyl, stearoyl, nonadecanoyl, icosanoyl, etc] which may have one or more (preferably 1 to 3) suitable substituent(s) as exemplified for those of "lower alkanoyl";

(3) lower alkenoyl [e.g. acryloyl, crotonoyl, isocrotonoyl, methacryloyl, 3-pentenoyl, 2,4-pentadienoyl, 5-hexenoyl, 2,4-hexadienoyl, etc] which may have one or more (preferably 1 to 3) suitable substituent(s) as exemplified for those of "lower alkanoyl";

(4) higher alkenoyl [e.g. 4-heptenoyl, 3-octenoyl, 3,6-decadienoyl, 3,7,11-trimethyl-2,6,10-dodecatrienoyl, 4,10-heptadecadienoyl, etc] which may have one or more (preferably 1 to 3) suitable substituent(s) as exemplified for those of "lower alkanoyl";

(5) protected carboxy, in which the preferred one may be esterified carboxy such as lower alkoxycarbonyl [e.g. methoxycarbonyl, ethoxycarbonyl, propoxycarbonyl, butoxycarbonyl, t-butoxycarbonyl, pentyloxycarbonyl, hexyloxycarbonyl, etc], halo(lower)alkoxycarbonyl [e.g. (chloromethoxy) carbonyl, (2,2,2-trichloroethoxy)carbonyl, (2,2,2-trifluoroethoxy)carbonyl, (2-chloropropoxy)carbonyl, (1-fluoro-4-bromobutoxy)carbonyl, (4-chloropentyloxy)-=carbonyl, (6-chlorohexyloxy)carbonyl, etc], higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc], aryloxycarbonyl [e.g. phenoxycarbonyl, naphthyloxycarbonyl, etc], ar(lower)alkoxycarbonyl which may have one or more (preferably 1 to 3) suitable substituent(s) such as phenyl (lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc], or the like;

(6) carboxy;

(7) lower alkylsulfonyl [e.g. methylsulfonyl, ethylsulfonyl, propylsulfonyl, isopropylsulfonyl, pentylsulfonyl, butylsulfonyl, etc];

(8) arylsulfonyl [e.g. phenylsulfonyl, 1-(or 2-)-naphthylsulfonyl, etc] which may have one or more (preferably 1 to 3) suitable substituent(s) such as lower alkyl, di(lower)alkylamino, lower alkylamino (e.g. methylamino, ethylamino, propylamino, butylamino, t-butylamino, pentylamino, hexylamino, etc), or the like;

(9) ar(lower)alkylsulfonyl such as phenyl(lower) alkylsulfonyl [e.g. benzylsulfonyl, phenethylsulfonyl, benzhydrylsulfonyl, etc], or the like;

(10) aryl(lower)alkanoyl [e.g. benzoyl, naphthoyl (e.g. 1-naphthoyl, 2-naphthoyl, etc), anthrylcarbonyl, 2-phenylacetyl, 2-phenylpropionyl, 4-(1-naphthyl) butyryl, 3-phenylvaleryl, 2,5-diphenylhexanoyl, etc] which may have one or more (preferably 1 to 3) suitable substituent(s) such as lower alkoxy, aryl (e.g. phenyl, naphthyl, anthryl, etc), or the like;

(11) aryl(lower)alkenoyl (e.g. 3-phenylacryloyl, 2-phenylacryloyl, 2-naphthylacryloyl, 3-phenylcrotonoyl, 4-phenylisocrotonoyl, 2-benzylacryloyl, 5-phenyl-3-pentenoyl, 3-naphthyl-2,4-pentadienoyl, 2-phenyl-5-hexenoyl, 6-phenyl-2,4-hexadienoyl, etc);

(12) heterocyclic(lower)alkanoyl which may have one or more (preferably 1 to 3) suitable substituent(s) such as lower alkyl, acyl, ar(lower)alkyl (e.g. benzyl, phenethyl, etc) which may have lower alkoxy, lower alkylenedioxy (e.g. methylenedioxy, etc) or the like;
(13) heterocyclicsulfonyl;
(14) amidated carboxy such as carbamoyl, N-heterocyclic-carbamoyl which may have one or more (preferably 1 to 3) suitable substituent(s) such as lower alkyl, halogen, or the like, N-lower alkyl-N-heterocyclic-carbamoyl, N-lower alkylcarbamoyl (e.g. N-methylcarbamoyl, N-ethylcarbamoyl, N-propylcarbamoyl, N-butylcarbamoyl, N-t-butylcarbamoyl, N-pentylcarbamoyl, N-hexylcarbamoyl, etc) which may have one or more (preferably 1 to 3) suitable substituent(s) such as heterocyclic group, hydroxy, or the like, N-ar(lower)alkylcarbamoyl such as N-(mono- or di- or tri-)phenyl(lower)alkylcarbamoyl (e.g. N-benzylcarbamoyl, N-phenethylcarbamoyl, N-benzhydrylcarbamoyl, N-tritylcarbamoyl, etc), or the like; or the like.

Suitable "heterocyclic group" and "heterocyclic" moiety in the terms "heterocyclic-amino", "heterocyclic(lower)alkylamino", "heterocyclic(lower)alkanoyl", "heterocyclicsulfonyl", "N-heterocyclic-carbamoyl", and "N-lower alkyl-N-heterocyclic-carbamoyl" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g. 1H-azepinyl, etc), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl, etc) etc;

saturated 3 to 8-membered (more preferably 5 to 7 membered) heteromonocyclic group containing 1 to 4 nitrogen atom(s), for example, perhydroazepinyl (e.g. perhydro-1H-azepinyl, etc), pyrrolidinyl, imidazolidinyl, piperidyl, piperazinyl, etc;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, quinoxalinyl, imidazopyridyl [e.g. imidazo[4,5-c]pyridyl, etc], tetrahydroimidazopyridyl [e.g. 4,5,6,7-tetrahydro[4,5-c]pyridyl, etc], etc;

saturated condensed heterocyclic group containing 1 to 4 nitrogen atom(s), for example, 7-azabicyclo[2.2.1]-heptyl, 3-azabicyclo[3.2.2]nonanyl, etc;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc), etc;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc), dihydrothiazinyl, etc;

saturated 3 to 8-membered (more preferably 5 or 6-membered) heteromonocyclic group containing 1 to 2 sulfur atom(s) and 1 to 3 nitrogen atom(s), for example, thiazolidinyl, etc;

unsaturated condensed heterocyclic group containing 1 to 2 sulfur atom(s) and 1 to 3 nitrogen atom(s), for example, benzothiazolyl, benzothiadiazolyl, etc;

saturated condensed heterocyclic group containing 1 to 4 nitrogen atom(s), and saturated 3 to 8-membered heteromonocyclic group containing 1 to 2 oxygen atom(s) and 1 to 3 nitrogen atom(s), unsaturated 3 to 8-membered (more preferably 5 or 6-membered) heteromonocyclic group containing an oxygen atom, for example, furyl, etc;

unsaturated 3 to 8-membered (more preferably 5 or 6-membered) heteromonocyclic group containing an oxygen atom and 1 to 2 sulfur atom(s), for example, dihydrooxathiinyl, etc;

unsaturated condensed heterocyclic group containing 1 to 2 sulfur atom(s), for example, benzothienyl, benzodithiinyl, etc;

unsaturated condensed heterocyclic group containing an oxygen atom and 1 to 2 sulfur atom(s), for example, benzoxathiinyl, etc; or the like.

In aforesaid "acyl group", the preferred one may be
(1) lower alkoxycarbonyl, in which the more preferred one may be $(C_1-C_4)$alkoxycarbonyl, and the most preferred one may be t-butoxycarbonyl;
(2) lower alkenoyl, in which the more preferred one may be $(C_3-C_6)$alkenoyl, and the most preferred one may be crotonoyl, isocrotonoyl or 2,4-hexadienyl;
(3) aryl(lower)alkanoyl which may have one or more suitable substituent(s), in which the more preferred one may be phenyl(lower)alkanoyl or naphthyl(lower)alkanoyl, each of which may have 1 to 3 lower alkoxy or phenyl, the much more preferred one may be phenyl$(C_1-C_4)$alkanoyl which may have $(C_1-C_4)$alkoxy or phenyl, or naphthyl $(C_1-C_4)$alkanoyl, the most preferred one may be benzoyl, 4-methoxybenzoyl, 2-biphenylcarbonyl, or 1-naphthoyl;
(4) aryl(lower)alkenoyl, in which the more preferred one may be phenyl$(C_2-C_5)$alkenoyl, and the most preferred one may be 3-phenylacryloyl;
(5) aryloxycarbonyl, in which the more preferred one may be phenoxycarbonyl;
(6) arylsulfonyl which may have one or more suitable substituent(s), in which the more preferred one may be naphthylsulfonyl which may have 1 to 3 di(lower)alkylamino, the much more preferred one may be naphthylsulfonyl which may have di$(C_1-C_4)$alkylamino, and the most preferred one may be 5-dimethylamino-1-naphthylsulfonyl;
(7) heterocyclic(lower)alkanoyl which may have one or more suitable substituent(s), in which the more preferred one may be
(i) heterocyclic(lower)alkanoyl, wherein heterocyclic moiety is unsaturated 3 to 8-membered heteromonocyclic group containing 1 to 4 nitrogen atom(s), which may have 1 to 3 lower alkyl, the more preferred one may be pyridyl$(C_1-C_4)$-alkanoyl which may have $(C_1-C_4)$alkyl, pyrazinyl$(C_1-C_4)$-alkanoyl, or imidazolyl$(C_1-C_4)$alkanoyl, the much more preferred one may be pyridylcarbonyl which may have $(C_1-C_4)$ alkyl, 2-(pyridyl)acetyl, pyrazinylcarbonyl, or 2-(imidazolyl)-acetyl, and the most preferred one may be 2-(or 3-or 4-)-pyridylcarbonyl, (5-methyl-2-pyridyl)carbonyl, 2-(2-pyridyl)-acetyl, 2-pyrazinylcarbonyl, and 2-(2-imidazolyl)acetyl;

(ii) heterocyclic(lower)alkanoyl, wherein heterocyclic moiety is unsaturated condensed heterocyclic group containing 1 to 4 nitrogen atom(s), which may have 1 to 3 lower alkoxycarbonyl, the more preferred one may be quinolyl ($C_1$–$C_4$)alkanoyl, isoquinolyl($C_1$–$C_4$) alkanoyl, quinoxalinyl-($C_1$–$C_4$)alkanoyl, or tetrahydroimidazopyridyl($C_1$–$C_4$)alkanoyl, the much more preferred one may be quinolylcarbonyl, isoquinolylcarbonyl, quinoxalinylcarbonyl, tetrahydroimidazopyridylcarbonyl which may have 1 to 3 ($C_1$–$C_4$)alkoxycarbonyl, the most preferred one may be 2-(or 3- or 5-)quinolylcarbonyl, 1-(or 3-)-isoquinolylcarbonyl, 2-quinoxalinylcarbonyl, 4,5,6,7-tetrahydro-3H-imidazo[4,5-c]pyridin-6-ylcarbonyl, and 3-t-butoxycarbonyl-5-t-butoxycarbonyl-4,5,6,7-tetrahydro-3H-imidazo[4,5-c]pyridin-6-ylcarbonyl;

(iii) heterocyclic(lower)alkanoyl, wherein heterocyclic moiety is saturated 3 to 8-membered heteromonocyclic group containing 1 to 4 nitrogen atom(s), which may have 1 to 3 lower alkoxycarbonyl or phenyl(lower) alkyl which may have lower alkylenedioxy, the more preferred one may be pyrrolidinyl($C_1$–$C_4$)alkanoyl which may have 1 to 3 ($C_1$–$C_4$)-alkoxycarbonyl, piperidyl($C_1$–$C_4$)alkanoyl which may have 1 to 3 ($C_1$–$C_4$)-alkoxycarbonyl, or piperazinyl which may have 1 to 3 phenyl($C_1$–$C_4$)alkyl having ($C_1$–$C_4$) alkylenedioxy, and the most preferred one may be 1-t-butoxycarbonyl-2-pyrrolidinylcarbonyl, 1-(or 2- or 4-)piperidylcarbonyl, and 1-t-butoxycarbonyl-2-(or 4-)piperidylcarbonyl;

(iv) heterocyclic(lower)alkanoyl, wherein heterocyclic moiety is saturated 3 to 8-membered heteromonocyclic group containing 1 to 2 oxygen atom(s) and 1 to 3 nitrogen atom(s), the more preferred one may be morpholinyl ($C_1$–$C_4$)alkanoyl, the much more preferred one may be morpholinylcarbonyl, and the most preferred one may be morpholinocarbonyl; or the like;

(8) heterocyclicsulfonyl, in which the more preferred one may be heterocyclicsulfonyl, wherein heterocyclic moiety is unsaturated condensed heterocyclic group containing 1 to 4 nitrogen atom(s), the much more preferred one may be quinolylsulfonyl, and the most preferred one may be 8-quinolylsulfonyl;

(9) carbamoyl;

(10) N-heterocyclic-carbamoyl which may have one or more suitable substituent(s), in which the more preferred one may be (i) N-heterocycliccarbamoyl, wherein heterocyclic moiety is unsaturated 3 to 8-membered heteromonocyclic group containing 1 to 4 nitrogen atom(s), which may have 1 to 3 lower alkyl or halogen, the much more preferred one may be N-pyridylcarbamoyl which may have 1 to 3 ($C_1$–$C_4$)alkyl or halogen, and the most preferred one may be N-(2-pyridyl)carbamoyl, N-(5-methyl-2-pyridyl)carbamoyl, and N-(5-chloro-2-pyridyl)carbamoyl;

(ii) N-heterocyclic-carbamoyl, wherein heterocyclic moiety is unsaturated condensed heterocyclic group containing 1 to 4 nitrogen atoms, the more preferred one may be N-quinolylcarbamoyl, and the most preferred one may be N-[2-(or 3-)quinolyl]carbamoyl;

(iii) N-heterocyclic-carbamoyl, wherein heterocyclic moiety is unsaturated condensed heterocyclic group containing 1 to 2 oxygen atom(s) and 1 to 3 nitrogen atom(s), which may have 1 to 3 halogen, the more preferred one may be N-benzoxazolylcarbamoyl which may have 1 to 3 halogen, and the most preferred one may be N-(5-chloro-2-benzoxazolyl)carbamoyl;

(iv) N-heterocyclic-carbamoyl, wherein heterocyclic moiety is unsaturated condensed heterocyclic group containing 1 to 2 sulfur atom(s) and 1 to 3 nitrogen atom(s), the more preferred one may be N-benzothiazolylcarbamoyl, and the most preferred one may be N-(2-benzothiazolyl)carbamoyl;

(v) N-heterocyclic-carbamoyl, wherein heterocyclic moiety is saturated 3 to 8-membered heteromonocyclic group containing 1 to 2 oxygen atom(s) and 1 to 3 nitrogen atom(s), the more preferred one may be N-morpholinylcarbamoyl, and the most preferred one may be N-morpholinocarbamoyl;

(11) N-lower alkyl-N-heterocyclic-carbamoyl, in which the more preferred one may be N-lower alkyl-N-heterocyclic-carbamoyl, wherein heterocyclic moiety is unsaturated 3 to 8-membered heteromonocyclic group containing 1 to 4 nitrogen atom(s), the much more preferred one may be N-($C_1$–$C_4$)alkyl-N-pyridylcarbamoyl, and the most preferred one may be N-methyl-N-(2-pyridyl)carbamoyl;

(12) N-heterocyclic(lower)alkylcarbamoyl, in which the more preferred one may be N-heterocyclic(lower) alkylcarbamoyl, wherein heterocyclic moiety is unsaturated 3 to 8-membered heteromonocyclic group containing 1 to 4 nitrogen atom(s), the much more preferred one may be N-pyridyl($C_1$–$C_4$)-alkylcarbamoyl, and the most preferred one may be (2-pyridyl)methylcarbamoyl;

(13) N-lower alkylcarbamoyl which may have one or more hydroxy, in which the more preferred one may be N-($C_1$–$C_4$)-alkylcarbamoyl which may have 1 to 3 hydroxy, and the most preferred one may be N-(2-hydroxypropyl)carbamoyl;

(14) higher alkanoyl which may have one or more suitable, substituent(s), in which the more preferred one may be higher alkanoyl which may have 1 to 3 hydroxy, the much more preferred one may be ($C_{10}$–$C_{18}$)alkanoyl which may have hydroxy, and the most preferred one may be 3-hydroxy-15-methylhexadecanoyl.

Suitable "lower alkanoyl" moiety in the term "heterocyclic(lower)alkanoyl" can be referred to the ones as exemplified for "lower alkanoyl".

Suitable "lower alkyl" moiety in the term "N-heterocyclic (lower)alkylcarbamoyl" can be referred to the ones as exemplified for "lower alkyl".

Suitable example of "acyl" moiety in the term "acyl (lower)alkyl" may be the ones as exemplified for "acyl group".

The preferred "acyl" moiety in the term "acyl(lower) alkyl" may be carboxy; protected carboxy, in which the more preferred one may be lower alkoxycarbonyl, halo (lower)alkoxycarbonyl, or ar(lower)alkoxycarbonyl, the much more preferred one may be ($C_1$–$C_4$)alkoxycarbonyl, halo($C_1$–$C_4$)alkoxycarbonyl or phenyl-($C_1$–$C_4$) alkoxycarbonyl, and the most preferred one may be methoxycarbonyl, 2,2,2-trichloroethoxycarbonyl or benzyloxycarbonyl; amidated carboxy, in which the more preferred one may be carbamoyl, N-lower alkylcarbamoyl, or N-ar(lower)alkylcarbamoyl, the much more preferred one may be carbamoyl, N-($C_1$–$C_4$)alkylcarbamoyl, or N-phenyl ($C_1$–$C_4$)-alkylcarbamoyl, and the most preferred one may be carbamoyl, N-methylcarbamoyl, or N-benzylcarbamoyl.

Suitable example of "lower alkyl" moiety in the terms "acyl(lower)alkyl", "protected carboxy(lower)alkyl", "carboxy(lower)alkyl", "amidated carboxy(lower)alkyl", and "cyano(lower)alkyl", in which the preferred one may be ($C_1$–$C_4$)alkyl.

Suitable "protected carboxy" moiety in the term of "protected carboxy(lower)alkyl" can be referred to the ones as exemplified for "protected carboxy".

Suitable "amidated carboxy" moiety in the term of "amidated carboxy(lower)alkyl" can be referred to the ones as exemplified for "amidated carboxy".

Suitable "a leaving group" may include halogen, lower alkoxy, aryloxy (e.g. phenoxy, etc), and the like.

Suitable "amidating agent" may be the amino compound corresponding to the object "amidated carboxy", and the concrete example thereof may be ammonia or its chemical equivalent, heterocyclic-amine, N-lower alkyl-heterocyclic-amine, lower alkylamine which may have one or more (preferably 1 to 3) suitable substituent(s), ar(lower)alkylamine, or the like.

Suitable "heterocyclic" moiety and "lower alkyl" moiety in these compounds can be referred to the ones as exemplified for "heterocyclic group" and "lower alkyl", respectively.

Suitable examples of "suitable substituent(s)" in the term "lower alkylamine which may have one or more suitable substituent(s)" can be referred to the ones as exemplified for the "suitable substituent(s)" of "N-lower alkylcarbamoyl which may have one or more suitable substituent(s)".

In the following, some of the preferred embodiments of the fatty acid derivative (I) of the present invention are shown.

(1) the derivative (I), wherein
  $R^1$ is lower alkoxycarbonyl,
  $R^2$ is carboxy(lower)alkyl,
  $R^3$ is higher alkyl,
  $R^4$ is carbamoyl(lower)alkyl, and
  X is —O—.
(2) the derivative (I), wherein
  $R^1$ is lower alkenoyl, and
  $R^2$, $R^3$, $R^4$ and X are each as defined above in (1).
(3) the derivative (I), wherein
  $R^1$ is phenyl(lower)alkanoyl or naphthyl(lower)alkanoyl, each of which may have 1 to 3 lower alkoxy or phenyl, and
  $R^2$, $R^3$, $R^4$ and X are each as defined above in (1).
(4) the derivative (I), wherein
  $R^1$ is phenyl(lower)alkenoyl, and
  $R^2$, $R^3$, $R^4$ and X are each as defined above in (1).
(5) the derivative (I), wherein
  $R^1$ is phenoxycarbonyl, and
  $R^2$, $R^3$, $R^4$ and X are each as defined above in (1).
(6) the derivative (I), wherein
  $R^1$ is naphthylsulfonyl which may have 1 to 3 di(lower)alkylamino, and
  $R^2$, $R^3$, $R^4$ and X are each as defined above in (1).
(7) the derivative (I), wherein
  $R^1$ is heterocyclic(lower)alkanoyl, wherein heterocyclic moiety is unsaturated 3 to 8-membered heteromonocyclic group containing 1 to 4 nitrogen atom(s), which may have 1 to 3 lower alkyl [the more preferred one may be pyridyl(lower)alkanoyl which may have (lower)alkyl, pyrazinyl(lower)alkanoyl, or imidazolyl (lower)alkanoyl], and
  $R^2$, $R^3$, $R^4$ and X are each as defined above in (1).
(8) the derivative (I), wherein
  $R^1$ is heterocyclic(lower)alkanoyl, wherein heterocyclic moiety is unsaturated condensed heterocyclic group containing 1 to 4 nitrogen atom(s), which may have 1 to 3 lower alkoxycarbonyl [the more preferred one may be quinolyl(lower)alkanoyl, isoquinolyl(lower)alkanoyl, quinoxalinyl(lower)alkanoyl, or tetrahydroimidazopyridyl(lower)alkanoyl], and
  $R^2$, $R^3$, $R^4$ and X are each as defined above in (1).
(9) the derivative (I), wherein
  $R^1$ is heterocyclic(lower)alkanoyl, wherein heterocyclic moiety is saturated 3 to 8-membered heteromonocyclic group containing 1 to 4 nitrogen atom(s), which may have 1 to 3 lower alkoxycarbonyl or phenyl(lower)alkyl which may have lower alkylenedioxy [the more preferred one may be pyrrolidinyl(lower)alkanoyl which may have 1 to 3 (lower)alkoxycarbonyl, piperidyl(lower)alkanoyl which may have 1 to 3 (lower)alkoxycarbonyl; or piperazinyl(lower)alkyl which may have 1 to 3 phenyl(lower)alkyl having (lower)alkylenedioxy], and
  $R^2$, $R^3$, $R^4$ and X are each as defined above in (1).
(10) the derivative (I), wherein
  $R^1$ is heterocyclic(lower)alkanoyl, wherein heterocyclic moiety is saturated 3 to 8-membered heteromonocyclic group containing 1 to 2 oxygen atom(s) and 1 to 3 nitrogen atom(s) [the more preferred one may be morpholinyl(lower)alkanoyl], and
  $R^2$, $R^3$, $R^4$ and X are each as defined above in (1).
(11) the derivative (I), wherein
  $R^1$ is heterocyclicsulfonyl, wherein heterocyclic moiety is unsaturated condensed heterocyclic group containing 1 to 4 nitrogen atom(s) [the much more preferred one may be quinolylsulfonyl], and
  $R^2$, $R^3$, $R^4$ and X are each as defined above in (1).
(12) the derivative (I), wherein
  $R^1$ is N-heterocyclic-carbamoyl, wherein heterocyclic moiety is unsaturated 3 to 8-membered heteromonocyclic group containing 1 to 4 nitrogen atom(s), which may have 1 to 3 lower alkyl or halogen [the more preferred one may be N-pyridylcarbamoyl which may have 1 to 3 (lower)alkyl or halogen], and
  $R^2$, $R^3$, $R^4$ and X are each as defined above in (1).
(13) the derivative (I), wherein
  $R^1$ is N-heterocyclic-carbamoyl, wherein heterocyclic moiety is unsaturated condensed heterocyclic group containing 1 to 4 nitrogen atoms [the more preferred one may be N-quinolylcarbamoyl], and
  $R^2$, $R^3$, $R^4$ and X are each as defined above in (1).
(14) the derivative (I), wherein
  $R^1$ is N-heterocyclic-carbamoyl, wherein heterocyclic moiety is unsaturated condensed heterocyclic group containing 1 to 2 oxygen atom(s) and 1 to 3 nitrogen atom(s), which may have 1 to 3 halogen, [the more preferred one may be N-benzoxazolylcarbamoyl which may have 1 to 3 halogen], and
  $R^2$, $R^3$, $R^4$ and X are each as defined above in (1).
(15) the derivative (I), wherein
  $R^1$ is N-heterocyclic-carbamoyl, wherein heterocyclic moiety is unsaturated condensed heterocyclic group containing 1 to 2 sulfur atom(s) and 1 to 3 nitrogen atom(s) [the more preferred one may be N-benzothiazolylcarbamoyl] and
  $R^2$, $R^3$, $R^4$ and X are each as defined above in (1).
(16) the derivative (I), wherein
  $R^1$ is N-heterocyclic-carbamoyl, wherein heterocyclic moiety is saturated 3 to 8-membered heteromonocyclic group containing 1 to 2 oxygen atom(s) and 1 to 3 nitrogen atom(s) [the more preferred one may be N-morpholinylcarbamoyl], and $R^2$, $R^3$, $R^4$ and X are each as defined above in (1).

(17) the derivative (I), wherein $R^1$ is N-lower alkyl-N-heterocyclic-carbamoyl, wherein heterocyclic moiety is unsaturated 3 to 8-membered heteromonocyclic group containing 1 to 4 nitrogen atom(s) [the more preferred one may be N-(lower)alkyl-N-pyridylcarbamoyl], and $R^2$, $R^3$, $R^4$ and X are each as defined above in (1).

(18) the derivative (I), wherein $R^1$ is N-heterocyclic(lower)alkylcarbamoyl, wherein heterocyclic moiety is unsaturated 3 to 8-membered heteromonocyclic group containing 1 to 4 nitrogen atom(s) [the more preferred one may be N-pyridyl(lower)alkylcarbamoyl], and

(19) the derivative (I), wherein $R^1$ is N-lower alkylcarbamoyl which may have 1 to 3 hydroxy, and $R^2$, $R^3$, $R^4$ and X are each as defined above in (1).

(20) the derivative (I), wherein $R^1$ is higher alkanoyl which may have 1 to 3 hydroxy, and $R^2$, $R^3$, $R^4$ and X are each as defined above in (1).

The processes for preparing the object compound (I) of the present invention are explained in detail in the following.

Process 1

The compound (I) or a salt thereof can be prepared by reacting the compound (II) or a reactive derivative at the carboxy group or a salt thereof with the compound (III) or a salt thereof.

Suitable salts of the compounds (II) and (III) can be referred to the ones as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc], dialkylphosphorous acid, sulfurous acid, thiosulfuric acid, sulfuric acid, sulfonic acid [e.g. methanesulfonic acid, etc], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc] or aromatic carboxylic acid [e.g. benzoic acid, etc]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl

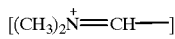

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc] or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc], and the like. These reactive derivatives can optionally be selected from them according to the kind of the compound (II) to be used.

In the case that the group X is

in the compound (III), the compound (III) can be used in the form of its reactive derivative at the amino group.

Suitable said reactive derivative at the amino group may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

The reaction is usually carried out in a conventional solvent such as water, alcohol [e.g. methanol, ethanol, etc], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; 1-ethyl-3-(3-dimethylaminopropyl)carbodiimide, or the like.

The reaction may also be carried out in the presence of an inorganic or organic base such as an alkali metal carbonate, alkali metal bicarbonate, tri(lower)alkylamine (e.g. triethylamine, etc), pyridine, di(lower)alkylaminopyridine, N-(lower)alkylmorpholine, N,N-di(lower)alkylbenzylamine, or the like.

The reaction temperature is not critical, and the reaction is usually carried out under cooling to warming.

Process 2

The compound (I) or a salt thereof can be prepared by reacting the compound (IV) or a reactive derivative at the amino group or a salt thereof with the compound (V) or a reactive derivative at the acyl group or a salt thereof.

Suitable salts of the compounds (IV) and (V) can be referred to the ones as exemplified for the compound (I).

The reaction of this process can be carried out according to a similar manner to that of Process 1, and so the reaction condition can be referred to the explanation therein.

Process 3

The compound (Ia) or a salt thereof can be prepared by reacting the compound (VI) or a salt thereof with amidating agent.

Suitable salts of the compounds (Ia) and (VI) can be referred to the ones as exemplified for the compound (I).

The reaction of this process can be carried out according to the manner disclosed in Examples or a similar manner thereto.

Process 4

The compound (Ic) or a salt thereof can be prepared by subjecting a compound (Ib) or a salt thereof to elimination reaction of carboxy protective group.

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc], an alkaline earth metal [e.g. magnesium, calcium, etc], the hydroxide or carbonate or bicarbonate thereof, trialkylamine [e.g. trimethylamine, triethylamine, etc], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc] and an inorganic acid [e.g. hydrochloric acid, hydrobromic acid, sulfuric acid, hydrogen chloride, hydrogen bromide, etc].

The elimination using Lewis acid such as trihaloacetic acid [e.g. trichloroacetic acid, trifluoroacetic acid, etc] aluminium halide (e.g. aluminium chloride, etc) or the like is preferably carried out in the presence of cation trapping agents [e.g. anisole, phenol, etc].

The reaction is usually carried out in a solvent such as water, an alcohol [e.g. methanol, ethanol, etc], nitromethane, methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction method applicable for the elimination reaction may include chemical reduction and catalytic reduction.

Suitable reducing agents to be used in chemical reduction are a combination of metal [e.g. tin, zinc, iron, etc] or metallic compound [e.g. chromium chloride, chromium acetate, etc] and an organic or inorganic acid [e.g. formic acid, acetic acid, propionic acid, trifluoroacetic acid, p-toluenesulfonic acid, hydrochloric acid, hydrobromic acid, etc].

Suitable catalysts to be used in catalytic reduction are conventional ones such as platinum catalysts [e.g. platinum plate, spongy platinum, platinum black, colloidal platinum, platinum oxide, platinum wire, etc], palladium catalysts [e.g. spongy palladium, palladium black, palladium oxide, palladium on carbon, colloidal palladium, palladium on barium sulfate, palladium on barium carbonate, etc], nickel catalysts [e.g. reduced nickel, nickel oxide, Raney nickel, etc], cobalt catalysts [e.g. reduced cobalt, Raney cobalt, etc], iron catalysts [e.g. reduced iron, Raney iron, etc], copper catalysts [e.g. reduced copper, Raney copper, Ullman copper, etc] and the like.

The reduction is usually carried out in a conventional solvent which does not adversely influence the reaction such as water, methanol, ethanol, propanol, dioxane, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc, or a mixture thereof.

The reaction temperature of this reduction is not critical and the reaction is usually carried out under cooling to warming.

Process 5

The compound (Id) or a salt thereof can be prepared by reacting the compound (IV) or a reactive derivative at the amino group or a salt thereof with lower aliphatic hydrocarbon compound substituted with oxo which may have one or more suitable substituent(s) in the presence of a reducing agent.

Suitable salt of the compound (Id) can be referred to the ones as exemplified for the compound (I).

Suitable "a reducing agent" may include a conventional reducing agent such as sodium borohydride, lithium aluminum hydride, sodium cyanoborohydride, or the like.

The reaction of this process can be carried out according to the manner disclosed in Examples or a similar manner thereto.

Process 6

The compound (If) or a salt thereof can be prepared by reacting the compound (Ie) or a salt thereof with amidating agent.

Suitable salts of the compounds (Ie) and (If) can be referred to the ones as exemplified for the compound (I).

The reaction of this process can be carried out according to a similar manner to that of Process 1, and so the reaction conditions can be referred to the explanation therein.

Process 7

The compound (Ia) or a salt thereof can be prepared by reacting the compound (VII) or a salt thereof with amidating agent.

Suitable salt of the compound (VII) can be referred to the ones as exemplified for the compound (I).

The reaction of this process can be carried out according to the manner disclosed in Examples or a similar manner thereto.

It is to be noted the compound (I) or a salt thereof can be prepared by the methods other than aforesaid Processes 1 to 7, for examples, by the other methods disclosed in Examples in this specification.

Among the starting compounds, there are some novel compounds, and they can be prepared by the methods, for examples, disclosed in Preparations in this specification.

Biological Property of the Compound (I)

In order to show the utility of the object compound (I), the biological test data on phospholipase $A_2$ assay of the representative compound of the compound (I) is shown in the following.

Test on the inhibitory effect against phospholipase $A_2$($PLA_2$)

[I] Test Method

The substrate, [$^{14}C$]phosphatidylcholine (L-3-phosphatidylcholine, 1-stearyl-2-[1-$^{14}C$]arachidonyl, was dried under $N_2$ gas and suspended in deionized water with a probe sonicater. The standard reaction mixture in a total volume of 800 μl contained Tris-HCl buffer (10 mM, pH 7.4), $CaCl_2$ (5 mM) and 10 ng/ml enzyme, $PLA_2$ group I (from porcine pancreas, 700 units/mg, Boehringer Mannheim Yamanouchi Co., Ltd.). The reaction was started by addition of 5 μM [$^{14}C$]phosphatidylcholine (L-3-phosphatidylcholine, 1-stearyl-2-[1-$^{14}C$]arachidonyl to the enzyme solution. Following incubation at 37° C. for 30 minutes, the reaction was terminated by addition of 2 ml of Dole's reagent[1]). To determine the release of $^{14}C$-arachidonic acid from the phospholipid substrate, free fatty acid was extracted by the method of Natori et al[2]), and counted in 8 ml of Liquifluor (Du Pont, New England Nuclear). On the inhibition assay, inhibitor or vehicle was preincubated with enzyme at 37° C. for 30 minutes. Each sample was dissolved in methanol (1.25% final). All data are the average of at least duplicate determinations corrected for none enzymatic hydrolysis. Data were expressed as percent inhibition.

[1]) Dole, V. P. & H. Meinertz: Microdetermination of long-chain fatty acid in plasma and tissues. J. Biol. Chem. 235: 2595–2599, 1960
[2]) Natori, Y; K. Karasawa, H. Arai, Y. Tamori-Natori & S. Nojima; Partial purification and properties of phospholipase $A_2$ from rat liver mitochondria. J. Biochem. 93; 631–637, 1983

[II] Test Compound (3S)-3-[(2S)-5-Carboxy-2-(p-methoxybenzoylamino)-pentanoyl]oxyhexadecanamide (the compound of Example 9)

| [III] Test Result Percent inhibition | |
|---|---|
| Dose | % |
| 83 ng/ml | 87.1 |

It was confirmed that the same test compound also inhibited $PLA_2$ group II.

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous, intramuscular and intra-articular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The object compound (I) or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation including aerosols from metered dose inhaler, nebulizer or dry powder inhaler.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being of an animal, in case of oral administration, a daily dose of 0.001–200 mg of the object compound (I) per kg weight of a human being or an animal is generally given for the prevention and/or the treatment of aforesaid diseases in a human being or an animal.

The following preparations and examples are given only for the purpose of illustrating the present invention in more detail.

PREPARATION 1

To a solution of (S)-methyl 3-hydroxyhexadecanoate (10.0 g) in methanol (200 ml) was added aqueous 1N sodium hydroxide (77 ml). The mixture was refluxed for one hour and cooled to 0° C. The resulting precipitate was collected by filtration, and the solid was dissolved in a mixture of ethyl acetate (250 ml) and 1N hydrochloric acid (200 ml). The organic layer was washed with brine (200 ml), dried over magnesium sulfate, and concentrated under reduced pressure. The resulting solid was dissolved in tetrahydrofuran (100 ml). To this solution were added 1-hydroxybenzotriazole (7.56 g) and 1-ethyl-3-(3-dimethylaminopropyl)carbodiimide hydrochloride (10.7 g). After the mixture was stirred for one hour, 28% ammonium hydroxide (5 ml) was added to the mixture and this was stirred at room temperature overnight. Then this mixture was poured into a mixture of ethyl acetate (300 ml) and 0.1N hydrochloric acid (250 ml). The resulting crystalline solid was collected by filtration, washed with ethyl acetate, and recrystallized from 2-propanol (25 ml) to obtain (S)-3-hydroxyhexadecanamide (5.79 g).

NMR (DMSO-$d_6$, δ): 0.84 (3 H, t, J=7 Hz), 1.40-1.14 (24 H, m), 2.11 (2 H, d, J=6 Hz), 3.75 (1 H, m), 4.58 (1 H, d, J=5 Hz), 6.88 (1 H, s, br), 7.24 (1 H, s, br)

EXAMPLE 1

To a suspended solution of (S)-3-hydroxyhexadecanamide (3.45 g) and (S)-5-benzyloxycarbonyl-2-(tertiarybutoxycarbonylamino) pentanoic acid (4.50 g) in dichloromethane (150 ml) were added benzotriazol-1-yloxy-tris(dimethylamino) phosphonium hexafluorophosphate (5.66 g) and 4-dimethylaminopyridine (3.13 g). The mixture was stirred overnight. The precipitates were filtered off, and the filtrate was concentrated under reduced pressure. The residue was dissolved in ethyl acetate (150 ml) and washed with 1N hydrochloric acid (100 ml×3), water (100 ml), saturated sodium bicarbonate (100 ml×2), and brine (100 ml). Then, the solution was dried over magnesium sulfate, and concentrated under reduced pressure. The residue was chromatographed on a silica gel column to give (3S)-3-[(2S)-5-benzyloxycarbonyl-2-(tertiarybutoxycarbonylamino)-pentanoyl]oxyhexadecanamide (3.85 g).

NMR (DMSO-$d_6$, δ): 0.85 (3 H, t, J=7 Hz), 1.05–1.32 (24 H, m), 1.37 (9 H, s), 1.41–1.70 (4 H, m), 2.31 (4 H, m), 3.84 (1 H, br s), 5.07 (3 H, m), 6.84 (1 H, br s), 7.22 (1 H, d, J=8 Hz), 7.35 (5 H, s)

EXAMPLE 2

A solution of (3S)-3-[(2S)-5-benzyloxycarbonyl-2-(tertiarybutoxycarbonylamino)pentanoyl] oxyhexadecanamide (100 mg) in trifluoroacetic acid (1 ml) was stirred at room temperature for 20 minutes. Then, the mixture was concentrated under reduced pressure, and dissolved in ethyl acetate (15 ml). This solution was washed with saturated sodium bicarbonate aqueous solution (15 ml×2), dried over magnesium sulfate, and evaporated. The residue was dissolved in methanol (3 ml), and to this solution was added benzoic anhydride (40 mg). This mixture was allowed to stand at room temperature overnight. Then, the mixture was washed with saturated sodium bicarbonate aqueous solution, dried over magnesium sulfate, and concentrated under reduced pressure. The residue was chromatographed on a silica gel column to give (3S)-3-[(2S)-5-benzyloxy-carbonyl-2-(benzoylamino)pentanoyl] oxyhexadecanamide (76.8 mg).

NMR (CDCl$_3$, δ): 0.88 (3 H, t, J=7 Hz), 1.18–1.39 (22 H, m), 1.55–2.10 (6 H, m), 2.40–2.50 (4 H, m), 4.73 (1 H, m), 5.10–5.22 (3 H, m), 5.32 (1 H, m), 5.81 (1 H, br s), 5.96 (1 H, br s), 6.94 (1 H, d, J=7 Hz), 7.36 (5 H, s), 7.53 (1 H, t, J=7 Hz), 7.83 (2 H, d, J=7 Hz)

The following compounds (Examples 3 to 5) were obtained according to a similar manner to that of Example 2.

EXAMPLE 3

(3S)-3-[(2S)-5-Benzyloxycarbonyl-2-{(1-naphthoyl)amino}pentanoyl]oxyhexadecanamide NMR (CDCl$_3$—CD$_3$OD, δ): 0.88 (3 H, t, J=7 Hz), 1.18–1.41 (22 H, m), 1.62–2.14 (6 H, m), 2.42–2.53 (4 H, m), 4.83 (1 H, m), 5.11 (2 H, s), 5.28–5.41 (2 H, m), 5.93 (1 H, s, br), 6.66 (1 H, d, J=8 Hz), 7.33 (5 H, s, br), 7.35–7.60 (3 H, m), 7.67 (1 H, d, J=8 Hz), 7.88 (1 H, m), 7.95 (1 H, d, J=8 Hz), 8.34 (1 H, m)

EXAMPLE 4

(3S)-3-[(2S)-5-Benzyloxycarbonyl-2-(p-methoxybenzoylamino)pentanoyl]oxyhexadecanamide NMR (CDCl$_3$, δ): 0.88 (3 H, t, J=7 Hz), 1.13–1.37 (22 H, m), 1.57–2.08 (6 H, m), 2.38–2.50 (4 H, m), 3.86 (3 H, s), 4.70 (1 H, m), 5.12 (2 H, s), 5.33 (2 H, m), 5.98 (1 H, s, br), 6.85 (1 H, d, J=8 Hz), 6.94 (2 H, d, J=8 Hz), 7.28–7.41 (5 H, m), 7.78 (2 H, d, J=8 Hz)

EXAMPLE 5

(3S)-3-[(2S)-5-Benzyloxycarbonyl-2-{(2-quinolyl)carbonylamino}pentanoyl]oxyhexadecanamide NMR (CDCl$_3$, δ): 0.87 (3 H, t, J=7 Hz), 1.15–1.58 (22 H, m), 1.57–2.17 (6 H, n), 2.40–2.53 (4 H, m), 4.80 (1 H, m), 5.11 (2 H, s), 5.32 (1 H, m), 5.36 (1 H, s, br), 5.96 (1 H, s, br), 7.34 (5 H, m), 7.64 (1 H, dd, J=7 Hz, 8 Hz), 7.79 (1 H, dd, J=7 Hz, 8 Hz), 7.89 (1 H, d, J=8 Hz), 8.17 (1 H, d, J=8 Hz), 8.26 (1 H, d, J=8 Hz), 8.32 (1 H, d, J=8 Hz), 8.86 (1 H, d, J=8 Hz)

EXAMPLE 6

A solution of (3S)-3-[(2S)-5-benzyloxycarbonyl-2-(tertiarybutoxycarbonylamino)pentanoyl]oxyhexadecanamide (100 mg) in methanol (2 ml) was hydrogenated over 10% palladium on carbon (20 mg) under atmospheric pressure of hydrogen for 3.5 hours at room temperature. Then, the catalyst was filtered off with celite and the filtrate was concentrated under reduced pressure. The residue was recrystallized from a mixture of ethyl acetate (0.5 ml) and n-hexane (1 ml) to give (3S)-3-[(2S)-5-carboxy-2-(tertiarybutoxycarbonylamino)-pentanoyl]oxyhexadecanamide (40 mg).

NMR (DMSO-d$_6$, δ): 0.85 (3 H, t, J=7 Hz), 1.1–1.7 (37 H, m), 2.16 (2 H, m), 2.30 (2 H, dd, J=5 Hz, 4 Hz), 3.82 (1 H, m), 5.09 (1 H, m), 6.84 (1 H, br s), 7.21 (1 H, d, J=7.5 Hz), 7.35 (1 H, br s)

The following compounds (Examples 7 to 10) were obtained according to a similar manner to that of Example 6.

EXAMPLE 7

(3S)-3-[(2S)-5-Carboxy-2-(benzoylamino)-pentanoyl]oxyhexadecanamide

NMR (CDCl$_3$—CD$_3$OD, δ): 0.82 (3 H, t, J=6 Hz), 1.14–1.33 (22 H, m), 1.51–2.00 (6 H, m), 2.30 (2 H, m), 2.44 (2 H, d, J=6 Hz), 4.66 (1 H, m), 5.25 (1 H, m), 7.32 (2 H, d, J=7 Hz), 7.48 (1 H, d, J=6 Hz), 7.80 (2 H, d, J=7 Hz)

EXAMPLE 8

(3S)-3-[(2S)-5-Carboxy-2-{(1-naphthoyl)amino}-pentanoyl]oxyhexadecanamide

NMR (CDCl$_3$—CD$_3$OD, δ): 0.84 (3 H, t, J=7 Hz), 1.15–1.40 (22 H, m), 1.60–2.10 (6 H, m), 2.30–2.53 (4 H, m), 4.78 (1 H, m), 5.29 (1 H, m), 7.41–7.58 (4 H, m), 7.65 (1 H, dd, J=7 Hz, 1 Hz), 7.85 (1 H, m), 7.92 (1 H, d, J=8 Hz), 8.29 (1 H, m)

EXAMPLE 9

(3S)-3-[(2S)-5-Carboxy-2-(p-methoxybenzoylamino)-pentanoyl]oxyhexadecanamide

NMR (CD$_3$OD, δ): 0.89 (3 H, t, J=7 Hz), 1.18–1.44 (22 H, m), 1.57–2.04 (6 H, m), 2.34 (2 H, t, J=7 Hz), 2.39–2.60 (2 H, m), 3.84 (3 H, s), 4.52 (1 H, m), 5.27 (1 H, m), 6.98 (2 H, d, J=8 Hz), 7.85 (2 H, d, J=8 Hz)

EXAMPLE 10

(3S)-3-[(2S)-5-Carboxy-2-{(2-quinolyl)carbonylamino}-pentanoyl]oxyhexadecanamide NMR (CDCl$_3$, δ): 0.86 (3 H, t, J=7 Hz), 1.00–1.45 (22 H, m), 1.50–2.20 (6 H, m), 2.28–2.66 (4 H, m), 4.85 (1 H, m), 5.38 (1 H, m), 6.37 (1 H, s, br), 7.62 (1 H, t, J=8 Hz), 7.77 (1 H, t, J=8 Hz), 7.87 (1 H, d, J=8 Hz), 8.25 (1 H, d, J=8 Hz), 8.31 (1 H, d, J=8 Hz), 8.84 (1 H, d, J=8 Hz)

PREPARATION 2

(S)-N-Benzyl-3-hydroxyhexadecanamide was obtained according to a similar manner to that of Preparation 1.

NMR (CDCl$_3$, δ): 0.88 (1 H, t, J=7 Hz), 1.16–1.77 (28 H, m), 2.30 (1 H, dd, J=8 Hz, 14 Hz), 2.40 (1 H, dd, J=3 Hz, 14 Hz), 4.02 (1 H, m), 4.47 (2 H, d, J=5 Hz), 6.08 (1 H, br s), 7.20–7.39 (5 H, m)

Preparation 3

(S)-Methyl 3-hydroxyhexadecanoate (1.0 g) was dissolved in a solution of 40% methylamine in methanol (15 ml). This mixture was stirred at room temperature for 2 hours. The resulting crystalline solid was collected by filtration to give (S)-N-methyl-3-hydroxyhexadecanamide (0.71 g).

NMR (DMSO-d$_6$, δ): 0.86 (3 H, t, J=7 Hz), 1.10–1.46 (24 H, m), 2.12 (2 H, d, J=7 Hz), 2.55 (3 H, d, J=5 Hz), 3.77 (1 H, m), 4.59 (1 H, d, J=5 Hz), 7.51 (1 H, m)

PREPARATION 4

A solution of (3S)-3-[(2S)-5-benzyloxycarbonyl-2-(tertiarybutoxycarbonylamino)pentanoyl]oxyhexadecanamide (4.90 g) in 4N hydrogen chloride in ethyl acetate (10 ml) was stirred at room temperature for an hour, and then at 0° C. for an additional one hour. This solution was diluted with diethyl ether (25 ml). The resulting precipitate was collected by filtration, and washed with diethyl ether (30 ml). This crystalline solid was dried over potassium hydroxide under vacuum to yield (3S)-3-[(2S)-5-benzyloxycarbonyl-2-aminopentanoyl)oxyhexadecanamide hydrochloride (4.35 g).

NMR (CDCl$_3$, δ): 0.88 (3 H, t; J=7 Hz), 1.07–1.42 (22 H, m), 1.45–2.21 (6 H, m), 2.34–2.69 (4 H, m), 4.07 (1 H, m), 5.09 (2 H, s), 5.30 (1 H, m), 6.78 (1 H, br s), 7.35 (5 H, m)

PREPARATION 5

(3S)-3-[(2S)-5-Carboxy-2-aminopentanoyl]-oxyhexadecanamide was obtained according to a similar manner to that of Example 6.

NMR (CDCl$_3$—CD$_3$OD (20:1), δ): 0.87 (3 H, t, J=7 Hz), 1.05–1.41 (22 H, m), 1.47–2.21 (6 H, m), 2.28–2.76 (4 H, m), 4.08 (1 H, m), 5.33 (1 H, m)

PREPARATION 6

To a solution of (R)-3-hydroxyhexadecanamide (100 mg) and pyridine (210 µl) in dichloromethane (10 ml) was added methanesulfonyl chloride (144 µl). This mixture was stirred at room temperature overnight, and the resulting precipitate was filtered off. The filtrate was concentrated, and dissolved in ethyl acetate (20 ml). This solution was washed with 1N-hydrochloric acid (20 ml×3), saturated sodium carbonate (20 ml×2), and brine (20 ml). After drying over MgSO$_4$ and concentration, the residue was chromatographed on a silica gel, eluting with a mixture of dichloromethane and methanol (50:1) to give (R)-3-methanesulfonyloxyhexadecanamide (40 mg).

NMR (CDCl$_3$, δ): 0.87 (3 H, t, J=7 Hz), 1.35–1.50 (22 H, m), 1.81 (2 H, m), 2.62 (2 H, d, J=7 Hz), 3.04 (3 H, s), 5.04 (1 H, m), 5.45 (1 H, br s), 5.68 (1 H, br s)

PREPARATION 7

A solution of (R)-3-methanesulfonyloxyhexadecanamide (32 mg) and sodium azide (12 mg) in N,N-dimethylformamide (1 ml) was heated at 60° C. for 2 hours. The cooled mixture was partitioned between ethyl acetate (20 ml) and water (10 ml). The organic phase was washed with water (10 ml), and brine (10 ml), dried, and concentrated under vacuum, then the residue was recrystallized at −20° C. from a mixture of ethyl acetate (0.2 ml) and n-hexane (2 ml) to give (S)-3-azidohexadecanamide (14 mg).

NMR (CDCl$_3$, δ): 0.88 (3 H, t, J=7 Hz), 1.18–1.64 (24 H, m), 2.34 (1 H, dd, J=15 Hz, 8 Hz), 2.42 (1 H, dd, J=15 Hz, 6 Hz), 3.85 (1 H, m), 5.40 (1 H, br s), 5.62 (1 H, br s)

PREPARATION 8

A mixture of (S)-3-azidohexadecanamide (0.17 g) and 10% palladium on carbon (20 mg) was hydrogenated at atmospheric pressure for 5 hours. The catalyst was filtered off with celite, and the filtrate was concentrated under reduced pressure. The residue was recrystallized from ethyl acetate (3 ml) to give (S)-3-aminohexadecanamide (106 mg).

NMR (DMSO-d$_6$, δ): 0.85 (3 H, t, J=7 Hz), 1.13–1.52 (24 H, m), 1.94 (1 H, dd, J=14 Hz, 8 Hz), 2.08 (1 H, dd, J=14 Hz, 5 Hz), 2.89 (1 H, m), 6.72 (1 H, br s), 7.36 (1 H, br s)

The following compounds (Preparations 9 and 10) were obtained according to a similar manner to that of Preparation 1.
Preparation 9
3-Hydroxydecanamide NMR (DMSO-d$_6$, δ): 0.86 (3 H, t, J=7 Hz), 1.14–1.48 (12 H, m), 2.11 (2 H, d, J=7 Hz), 3.75 (1 H, m), 4.57 (1 H, d, J=5 Hz), 6.77 (1 H, br s), 7.24 (1 H, br s)

PREPARATION 10

(R)-3-Hydroxyhexadecanamide

NMR (DMSO-d$_6$, δ): 0.84 (3 H, t, J=7 Hz), 1.40-1.14 (24 H, m), 2.11 (2 H, d, J=6 Hz), 3.75 (1 H, m), 4.58 (1 H, d, J=5 Hz), 6.88 (1 H, br s), 7.26 (1 H, br s)

PREPARATION 11

(S)-Methyl 3-hydroxyhexadecanoate and benzyl bromide were reacted according to a similar manner to that of Preparation 1 to give (S)-benzyl 3-hydroxyhexadecanoate.

NMR (CDCl$_3$, δ): 0.87 (3 H, t, J=7 Hz), 1.16–1.58 (24 H, m), 2.46 (1 H, dd, J=16 Hz, 8 Hz), 2.56 (1 H, dd, J=16 Hz, 3 Hz), 2.84 (1 H, d, J=4 Hz), 4.02 (1 H, m), 5.15 (2 H, s), 7.36 (5 H, m)

PREPARATION 12

(S)-Methyl 3-hydroxyhexadecanoate and 2,2,2-trichloroethyl alcohol were reacted according to a similar manner to that of Preparation 1 to give (S)-(2,2,2-trichloroethyl) 3-hydroxyhexadecanoate.

NMR (CDCl$_3$, δ): 0.87 (3 H, t, J=7 Hz), 1.17–1.62 (24 H, m), 2.53 (1 H, d, J=5 Hz), 2.58 (1 H, dd, J=16 Hz, 8 Hz), 2.67 (1 H, dd, J=16 Hz, 4 Hz), 4.18 (1 H, m), 4.76 (1 H, d, J=12 Hz), 4.80 (1 H, d, J=12 Hz)

The following compounds (Preparations 13 and 14) were obtained according to a similar manner to that of Preparation 3.

PREPARATION 13

2-Hydroxy-N-methylpentadecanamide

NMR (CDCl$_3$, δ): 0.87 (3 H, t, J=7 Hz), 1.15–1.47 (22 H, m), 1.63 (1 H, m), 1.83 (1 H, m), 2.36 (1 H, d, J=5 Hz), 2.86 (3 H, d, J=6 Hz), 4.12 (1 H, m), 6.43 (1 H, br s)

PREPARATION 14

N-(N-Methylcarbamoylmethyl)tridecylamine

NMR (DMSO-d$_6$, δ): 0.86 (3 H, t, J=7 Hz), 1.15–1.34 (22 H, m), 2.03 (1 H, br s), 2.41 (2 H, t, J=7 Hz), 2.40 (3 H, d, J=5 Hz), 3.02 (2 H, s), 7.68 (1 H, br s)

PREPARATION 15

A solution of methyl 3-(tridecylamino)propionate (0.77 g) in 10N-methanolic ammonia (7 ml) was allowed to stand at room temperature for 7 days. The resultant crystal was collected by filtration and washed with a small portion of methanol to give 3-(tridecylamino)propionamide (0.16 g).

NMR (CDCl$_3$, δ): 0.88 (3 H, t, J=7 Hz), 1.18–1.59 (22 H, m), 2.36 (2 H, t, J=7 Hz), 2.61 (2 H, t, J=8 Hz), 2.87 (2 H, t, J=7 Hz), 5.30 (1 H, br s), 7.79 (1 H, br s)

PREPARATION 16

To an ice-cooled solution of methyl 3-oxododecanoate in methanol was added sodium borohydride (83 mg). After stirring for 20 minutes, 1N-hydrochloric acid (2.2 ml) was added. After concentration, the residue was dissolved in ethyl acetate (30 ml) and 0.1 N-hydrochloric acid (20 ml). The organic phase was washed with water (20 ml), saturated aqueous sodium bicarbonate (20 ml), and brine (20 ml), dried, and concentrated. The residue was dissolved in methanol (3 ml), and to this solution was added 1N-sodium hydroxide (2.4 ml). The mixture was refluxed for an hour, and diluted with water (30 ml). This aqueous solution was washed with dichloromethane (20 ml), acidified with 1N-hydrochloric acid (2.6 ml), and extracted with ethyl acetate (30 ml). This organic phase was washed with brine (20 ml), dried, and concentrated. The residue was recrystallized from a mixture of ethyl acetate (1 ml) and n-hexane (3 ml) to give 3-hydroxydodecanoic acid (0.27 g).

NMR (DMSO-d$_6$, δ): 0.86 (3 H, t, J=7 Hz), 1.13–1.47 (16 H, m), 2.22 (1 H, dd, J=8 Hz, 14 Hz), 2.29 (1 H, dd, J=7 Hz, 14 Hz), 3.79 (1 H, m)

PREPARATION 17

3-Hydroxytetradecanoic acid was obtained according to a similar manner to that of Preparation 16.

NMR (DMSO-$d_6$, δ): 0.86 (3 H, t, J=7 Hz), 1.12–1.48 (20 H, m), 2.22 (1 H, dd, J=8 Hz, 15 Hz), 2.28 (1 H, dd, J=5 Hz, 15 Hz), 3.78 (1 H, m)

PREPARATION 18

To a solution of 3-hydroxydodecanoic acid (0.26 g) in tetrahydrofuran (4 ml) was added 1-ethyl-3-(3-dimethylaminopropyl)carbodiimide hydrochloride (0.18 g) and 1-hydroxybenzotriazole (0.24 g). After stirring for 30 minutes, 28% ammonium hydroxide (0.17 ml) was added and the mixture was stirred at room temperature overnight. Then, the mixture was diluted with ethyl acetate (100 ml) and washed with 0.1 N-hydrochloric acid (100 ml×2), saturated sodium bicarbonate (50 ml), and brine (50 ml). After drying over magnesium sulfate and evaporation, the residue was recrystallized from isopropyl alcohol (1 ml) to give 3-hydroxydodecanamide (0.20 g).

NMR (DMSO-$d_6$, δ): 0.86 (3 H, t, J=7 Hz), 1.13–1.47 (16 H, m), 2.10 (2 H, d, J=7 Hz), 3.75 (1 H, m), 4.57 (1 H, d, J=5 Hz), 6.77 (1 H, br s), 7.25 (1 H, br s)

PREPARATION 19

3-Hydroxytetradecanamide was obtained according to a similar manner to that of Preparation 18.

NMR (DMSO-$d_6$, δ): 0.85 (3 H, t, J=7 Hz), 1.15–1.41 (20 H, m), 2.11 (2 H, d, J=7 Hz), 3.74 (1 H, m), 4.57 (1 H, d, J=5 Hz), 6.77 (1 H, br s), 7.24 (1 H, br s)

PREPARATION 20

To methanol (10 ml), cooled in an ice-brine bath, was added thionyl chloride (0.87 ml) dropwise. After stirring at 0° C. for 10 minutes, 2-hydroxypentadecanoic acid (1.54 g) was added. The mixture was stirred at room temperature for 3 hours, and concentrated under vacuum. The residue was dissolved in ethyl acetate (60 ml), and washed with water (40 ml×2), saturated aqueous sodium bicarbonate (30 ml), and brine (30 ml). The organic phase was dried, concentrated to dryness, and triturated in diisopropyl ether to give methyl 2-hydroxypentadecanoate (0.77 g).

NMR (CDCl$_3$, δ): 0.88 (3 H, t, J=7 Hz), 1.16–1.42 (22 H, m), 1.58–1.75 (2 H, m), 2.67 (1 H, d, J=7 Hz), 3.78 (3 H, s), 4.18 (1 H, m)

PREPARATION 21

To an ice-cooled solution of tridecanal (1.0 g), methyl 3-aminopropionate hydrochloride (704 mg), and sodium acetate (414 mg) in methanol (20 ml) was added sodium cyanoborohydride (317 mg). After stirring for 45 minutes, the mixture was quenched with water (20 ml), concentrated, and extracted with ethyl acetate (40 ml). The organic phase was washed with brine, dried, and concentrated under reduced pressure. The residue was purified on silica gel, eluting with 5% methanol in chloroform to give methyl 3-tridecylaminopropionate (0.78 g).

NMR (CDCl$_3$, δ): 0.88 (3 H, t, J=7 Hz), 1.18–1.41 (20 H, m), 1.55 (2 H, m), 2.62 (2 H, t, J=7 Hz), 2.69 (2 H, t, J=8 Hz), 2.96 (2 H, t, J=7 Hz), 3.71 (3 H, s)

PREPARATION 22

Methyl 2-(tridecylamino)acetate was obtained according to a similar manner to that of Preparation 21.

NMR (CDCl$_3$, δ): 0.88 (3 H, t, J=7 Hz), 1.14–1.63 (22 H, m), 2.58 (2 H, m), 3.40 (2 H, s), 3.72 (3 H, s)

PREPARATION 23

To an ice-cooled solution of tetradecanal (18.75 g) in diethyl ether (100 ml) was added acetic acid (5.66 ml) and potassium cyanide (6.64 g). The mixture was warmed to room temperature and stirred for 72 hours. The resulting solution was washed with water, and the aqueous phase was extracted with diethyl ether (50 ml). The combined organic phase was dried, and concentrated to dryness. The residue was purified by silica gel chromatography and triturated in diisopropyl ether (10 ml) to give 2-hydroxypentadecanenitrile (4.66 g).

NMR (CDCl$_3$, δ): 0.88 (3 H, t, J=7 Hz), 1.16–1.42 (20 H, m), 1.50 (2 H, m), 1.86 (2 H, m), 2.27 (1 H, d, J=7 Hz), 4.48 (1 H, ddd, J=7 Hz, 7 Hz, 7 Hz)

PREPARATION 24

2-Hydroxypentadecanenitrile (1.0 g) was suspended in concentrated hydrochloric acid (15 ml), and this suspension was vigorously stirred at room temperature for 24 hours. Then, this mixture was diluted with water (45 ml). The insoluble powder was collected by filtration, washed with water (10 ml×3), and dried to give 2-hydroxypentadecanamide (1.06 g).

NMR (DMSO-$d_6$, δ): 0.86 (3 H, t, J=7 Hz), 1.13–1.66 (24 H, m), 3.75 (1 H, m), 5.22 (1 H, d, J=6 Hz), 7.05 (1 H, br s), 7.11 (1 H, br s)

PREPARATION 25

2-Hydroxypentadecanenitrile (3.63 g) was suspended in concentrated hydrochloric acid (54 ml), and stirred for 66 hours. This mixture was stirred at 60° C. for 6 hours, and refluxed for 95 minutes. Then, this was cooled to room temperature, and diluted with water (150 ml). The resulting precipitate was collected by filtration, and recrystallized from the mixture of ethyl acetate (4 ml) and n-hexane (16 ml) to give 2-hydroxypentadecanoic acid (2.30 g).

NMR (DMSO-$d_6$, δ): 0.85 (3 H, t, J=7 Hz), 1.13–1.38 (22 H, m), 1.41–1.66 (2 H, m), 3.90 (1 H, dd, J=8 Hz, 5 Hz)

PREPARATION 26

(3R)-[(2R)-5-Benzyloxycarbonyl-2-aminopentanoyl]oxyhexadecanamide hydrochloride (1.67 g) was obtained according to a similar manner to that of Preparation 4.

NMR (DMSO-$d_6$, δ): 0.85 (3 H, t, J=7 Hz), 1.14–1.32 (22 H, m), 1.50–1.85 (6 H, m), 2.39 (4 H, m), 4.01 (1 H, m), 5.09 (2 H, s), 5.22 (1 H, m), 6.87 (1 H, m), 7.35 (5 H, m), 7.42 (1 H, br s), 8.28 (2 H, br s)

PREPARATION 27

(3S)-(2,2,2-Trichloroethyl) 3-[(2S)-5-benzyloxycarbonyl-2-(tertiarybutoxycarbonylamino)pentanoyl]oxyhexadecanoate (15.5 g) was dissolved with 4N-hydrogen chloride in ethyl acetate (30 ml), and this solution was stirred at room temperature for 40 minutes. After evaporation, the residue was dissolved in toluene (100 ml). To this solution was added triphosgene (5.67 g) and charcoal (100 mg), and this mixture was refluxed for 2 hours. Then, the solvent was removed by distillation, and the residue was crystallized in n-hexane (60 ml) at 4° C. to give (3S)-2,2,2-trichloroethyl) 3-[(2S)-5-benzyloxycarbonyl-2-isocyanatopentanoyl]-oxyhexadecanoate (8.0 g).

NMR (CDCl$_3$, δ): 0.88 (3 H, t, J=7 Hz), 1.15–1.39 (22 H, m), 1.60–2.00 (6 H, m), 2.39 (2 H, t, J=7 Hz), 4.36 (2 H, m), 4.72 (1 H, d, J=12 Hz), 4.77 (1 H, d, J=12 Hz), 5.12 (2 H, s), 5.34 (1 H, m), 7.35 (5 H, m)

PREPARATION 28

Isobutyl bromide (27.4 g) was added to magnesium (5.0 g) in tetrahydrofuran (100 ml). The mixture was stirred for 1 hour under nitrogen atmosphere. The mixture was added to a solution of 1,10-dibromodecane (50.0 g) and dilithium tetrachlorocuprate (1 m mole) in tetrahydrofuran (100 ml) at 0° C. under nitrogen atmosphere. The mixture was stirred at 0° C. for 1 hour and poured into a mixture of 7% hydrochloric acid (200 ml) and ethyl acetate (200 ml). The organic layer was washed with water, dried over magnesium sulfate and evaporated. The residue was distilled under reduced pressure to give a mixture of the product and 1,10-dibromodecane as a colorless oil (27.23 g) (bp.115–120° C./0.5 Torr). The mixture was chromatographed on a silica gel column eluting with n-hexane to give 1-bromo-12-methyltridecane as an oil (15.3 g).

NMR (CDCl$_3$, δ): 3.41 (2 H, t, J=7 Hz), 1.86 (2 H, m), 1.4–1.6 (1 H, m), 1.1–1.4 (18 H, m), 0.86 (6 H, d, J=7 Hz)

PREPARATION 29

Magnesium (1.5 g) was added to a solution of 1-bromo-12-methyltridecane (15.0 g) in tetrahydrofuran (200 ml). The mixture was refluxed for 10 minutes under nitrogen atmosphere and stirred for 1 hour at room temperature. A solid of carbon dioxide (50 g) was added to the mixture. To the mixture was added a mixture of 1% hydrochloric acid (300 ml) and ethyl acetate (150 ml). The organic layer was washed with water, dried over magnesium sulfate and evaporated. The residue was chromatographed on a silica gel column eluting with chloroform to give 13-methyltetradecanoic acid as an oil (7.54 g).

NMR (CDCl$_3$, δ): 2.35 (2 H, t, J=7 Hz), 1.4–1.7 (3 H, m), 1.1–1.4 (18 H, m), 0.88 (6 H, d, J=7 Hz)

PREPARATION 30

To a solution of 13-methyltetradecanoic acid (7.45 g) in dichloromethane (50 ml) was added oxalyl chloride (3 ml) and N,N-dimethylformamide (0.05 ml). The mixture was stirred for 1 hour and evaporated. The residue was dissolved in n-hexane (50 ml) and insoluble salts was filtered off. The filtrate was evaporated and the residue was dissolved in dichloromethane (50 ml). The solution was added to a solution of 2,2-dimethyl-1,3-dioxane-4,6-dione (4.42 g) and pyridine (4.90 g) in dichloromethane (50 ml) at 0° C. The mixture was stirred at 0° C. for 1 hour and at room temperature for 1 hour. The mixture was washed with diluted hydrochloric acid and water, dried over magnesium sulfate and evaporated. The residue was dissolved in benzyl alcohol (50 ml) and stirred at 100° C. for 1 hour. The solvent was removed under reduced pressure. The residue was chromatographed on a silica gel column eluting with a mixture of n-hexane and ethyl acetate (10:1) to give benzyl 15-methyl-3-oxohexadecanoate of a colorless oil (6.40 g).

NMR (CDCl$_3$, δ): 7.35 (5 H, s), 5.18 (2 H, s), 3.49 (2 H, s), 2.50 (2 H, t, J=7 Hz), 1.4–1.7 (3 H, m), 1.1–1.3 (18 H, m), 0.86 (6 H, d, J=7 Hz)

PREPARATION 31

To a solution of benzyl 15-methyl-3-oxohexadecanoate (3.74 g) in 2-propanol (50 ml) was added sodium borohydride (0.38 g) at 0° C. The mixture was stirred at 0° C. for 2 hours and poured into a mixture of ethyl acetate and diluted hydrochloric acid. The organic layer was washed with water, dried over magnesium sulfate and evaporated. The residue was chromatographed on a silica gel column eluting with a mixture of n-hexane and ethyl acetate (10:1) to give benzyl 3-hydroxy-15-methylhexadecanoate as a colorless oil (2.10 g).

NMR (CDCl$_3$, δ): 7.38 (5 H, s), 5.16 (2 H, s), 4.03 (1 H, m), 2.89 (1 H, d, J=3 Hz), 2.4–2.6 (2 H, m), 1.4–1.6 (3 H, m), 1.1–1.4 (20 H, m), 0.88 (6 H, d, J=7 Hz)

PREPARATION 32

To a solution of benzyl 3-hydroxy-15-methylhexadecanoate (1.77 g) and N-tertiarybutoxycarbonyl-L-phenylalanine (1.25 g) in dichloromethane (50 ml) was added benzotriazol-1-yloxy-tris(dimethylamino)phosphonium hexafluorophosphate (2.08 g) and 4-dimethylaminopyridine (1.22 g). The mixture was stirred at room temperature for 14 hours and evaporated. The residue was poured into a mixture of ethyl acetate and diluted hydrochloric acid. The organic layer was washed with water, dried over magnesium sulfate and evaporated to give almost pure benzyl 3-(N-tertiary butoxycarbonyl-L-phenylalanyl)oxy-15-methylhexadecanoate, which can be used for next step without further purification (2.87 g).

NMR (CDCl$_3$, δ): 7.1–7.4 (10 H, m), 5.25 (1 H, m), 5.12 (2 H, s), 4.92 (1 H, m), 4.50 (1 H, m), 2.8–3.2 (2 H, m), 2.5–2.7 (2 H, m), 1.5–1.7 (3 H, m), 1.40 (9 H, s), 1.1–1.4 (20 H, m), 0.88 (6 H, d, J=7 Hz)

PREPARATION 33

To a solution of benzyl 3-(N-tertiarybutoxycarbonyl-L-phenylalanyl)oxy-15-methylhexadecanoate (2.85 g) in methanol (50 ml) was added 10% palladium on active carbon (0.5 g) and water (5 ml). The mixture was stirred at room temperature under hydrogen atmosphere for 1 hour. The catalyst was filtered off and the solvent was removed under reduced pressure to give 3-(N-tertiarybutoxycarbonyl-L-phenylalanyl)oxy-15-methylhexadecanoic acid as an oil (2.31 g).

NMR (CDCl$_3$, δ): 7.1–7.4 (5 H, m), 5.22 (1 H, m), 5.00 (1 H, d, J=7 Hz), 4.52 (1 H, m), 2.9–3.2 (2 H, m), 2.5–2.7 (2 H, m), 1.5–1.7 (3 H, m), 1.40 (9 H, s), 1.1–1.4 (20 H, m), 0.88 (6 H, d, J=7 Hz)

PREPARATION 34

To a solution of 3-(N-tertiarybutoxycarbonyl-L-phenylalanyl)oxy-15-methylhexadecanoic acid (2.30 g) in tetrahydrofuran (30 ml) was added 1-hydroxybenzotriazole (0.58 g) and 1-ethyl-3-(3-dimethylaminopropyl) carbodiimide hydrochloride (0.82 g). The mixture was stirred at room temperature for 30 minutes. 28% Ammonia solution (0.5 ml) was added to the mixture and then the mixture was stirred at room temperature for 2 hours. The mixture was poured into a mixture of ethyl acetate and diluted hydrochloric acid. The organic layer was washed with water, dried over magnesium sulfate and evaporated. The residue was chromatographed on a silica gel column eluting with chloroform to give 3-(N-tertiarybutoxycarbonyl-L-phenylalanyl)oxy-15-methylhexadecanamide as white wax (1.41 g).

NMR (CDCl$_3$, δ): 7.1–7.4 (5 H, m), 4.9–5.3 (2 H, m), 4.3–4.6 (1 H, m), 2.9–3.2 (2 H, m), 2.3–2.6 (2 H, m), 1.4–1.7 (3 H, m), 1.4 (9 H, s), 1.1–1.3 (20 H, m), 0.86 (6 H, d, J=7 Hz)

PREPARATION 35

To a solution of 3-(N-tertiarybutoxycarbonyl-L-phenylalanyl)oxy-15-methylhexadecanamide (1.40 g) and anisole (1.0 g) in dichloromethane (30 ml) was added trifluoroacetic acid (5 ml). The mixture was stirred at room temperature for 30 minutes and evaporated. The residue was dissolved in diethyl ether (50 ml) and washed with sodium bicarbonate aqueous solution and water, dried over magnesium sulfate and evaporated. The residue was chromatographed on a silica gel column eluting with a mixture of chloroform and methanol (10:1) to give the product as white powder.

(S)-15-methyl-3-(L-phenylalanyl)oxyhexadecanamide (0.60 g)

[α]$_D^{23}$ −1.2° (c 0.5, CHCl$_3$)

NMR (CDCl$_3$, δ): 7.2–7.4 (5 H, m), 5.60 (1 H, br s), 5.25 (1 H, br s), 5.18 (1 H, m), 3.72 (1 H, t, J=7 Hz), 3.08 (1 H, dd, J=15 Hz, 6 Hz), 2.85 (1 H, dd, J=15 Hz, 6 Hz), 2.40 (2 H, m), 1.4–1.7 (5 H, m), 1.1–1.4 (20 H, m), 0.86 (6 H, d, J=7 Hz)

(R)-15-methyl-3-(L-phenylalanyl)oxyhexadecanamide (0.50 g)

[α]$_D^{23}$ +8.7° (c 0.5, CHCl$_3$)

NMR (CDCl$_3$, δ): 7.2–7.4 (5 H, m), 5.79 (1 H, br s), 5.42 (1 H, br s), 5.18 (1 H, m), 3.72 (1 H, m), 3.08 (1 H, dd, J=15 Hz, 6 Hz), 2.85 (1 H, dd, J=15 Hz, 6 Hz), 2.48 (2 H, d, J=6 Hz), 1.4–1.7 (5 H, m), 1.1–1.4 (20 H, m), 0.86 (6 H, d, J=7 Hz)

PREPARATION 36

To a solution of (S)-15-methyl-3-(L-phenylalanyl)-oxyhexadecanamide (0.58 g) in methanol (30 ml) was added 1N-sodium hydroxide aqueous solution (3 ml). The mixture was stirred at room temperature for 30 minutes and poured into a mixture of ethyl acetate and diluted hydrochloric acid. The organic layer was washed with water, dried over magnesium sulfate and evaporated. The residue was crystallized from diisopropyl ether to give (S)-3-hydroxy-15-methylhexadecanamide as white powder (0.20 g).

mp: 94–96° C.

[α]$_D^{23}$ +17.26° (c 0.5, CHCl$_3$)

NMR (CDCl$_3$, δ): 5.85 (1 H, br s), 5.56 (1 H, br s), 4.00 (1 H, m), 3.32 (1 H, br s), 2.2–2.5 (2 H, m), 1.1–1.7 (21 H, m), 0.86 (6 H, d, J=7 Hz)

PREPARATION 37

(S)-3-Hydroxy-15-methylhexadecanamide (0.20 g) was added to a solution of potassium hydroxide (0.1 g) in ethanol (10 ml). The mixture was refluxed for 15 hours, cooled and poured into a mixture of ethyl acetate and diluted hydrochloric acid. The organic layer was washed with water, dried over magnesium sulfate and evaporated. The residue was chromatographed on a silica gel column eluting with a mixture of chloroform and methanol (10:1) to give (S)-3-hydroxy-15-methylhexanoic acid as white powder (67 mg).

[α]$_D^{25}$ +11.18° (c 0.3, CHCl$_3$)

NMR (CDCl$_3$, δ): 4.03 (1 H, m), 2.4–2.7 (2 H, m), 1.4–1.6 (3 H, m), 1.1–1.4 (20 H, m), 0.86 (6 H, d, J=7 Hz)

PREPARATION 38

To a solution of (S)-3-hydroxy-15-methylhexadecanamide (0.18 g) and 5-benzyloxycarbonyl-2-(L-tertiarybutoxy-carbonylamino)pentanoic acid (0.22 g) in dichloromethane (10 ml) was added benzotriazol-1-yloxy-tris(dimethylamino)-phosphonium hexafluorophosphate (0.28 g) and 4-dimethylaminopyridine (0.16 g). The mixture was stirred at room temperature for 14 hours and evaporated. The residue was poured into a mixture of ethyl acetate and diluted hydrochloric acid. The organic layer was washed with water, dried over magnesium sulfate and evaporated. The residue was chromatographed on a silica gel column eluting with a mixture of chloroform and methanol (50:1) to give (3S)-3-[(2S)-5-benzyloxycarbonyl-2-(tertiarybutoxycarbonylamino)-pentanoyl]oxy-15-methylhexadecanamide as an oil (0.20 g).

NMR (CDCl$_3$, δ): 7.35 (5 H, s), 5.90 (1 H, br s), 5.31 (1 H, br s), 5.25 (1 H, m), 5.12 (2 H, s), 5.06 (1 H, m), 4.23 (1 H, m), 2.35–2.5 (4 H, m), 1.5–1.9 (5 H, m), 1.44 (9 H, s), 1.1–1.4 (22 H, m), 0.87 (6 H, d, J=7 Hz)

The following compounds (Examples 11 and 12) were obtained according to a similar manner to that of Example 1.

EXAMPLE 11

(3S)-N-Methyl-3-[(2S)-5-benzyloxycarbonyl-2-(tertiarybutoxycarbonylamino)pentanoyl]oxyhexadecanamide NMR (CDCl$_3$, δ): 0.88 (3 H, t, J=7 Hz), 1.12–1.90 (37 H, m), 2.74 (3 H, d, J=5 Hz), 4.21 (1 H, m), 5.05 (1 H, d, J=7 Hz), 5.12 (2 H, s), 5.23 (1 H, m), 5.99 (1 H, br s), 7.35 (5 H, m)

EXAMPLE 12

(3S)-N-Benzyl-3-[(2S)-5-benzyloxycarbonyl-2-(tertiarybutoxycarbonylamino)pentanoyl]oxyhexadecanamide NMR (CDCl$_3$, δ): 0.88 (3 H, t, J=7 Hz), 1.17–1.37 (22 H, m), 1.43 (9 H, s), 1.37–1.48 (2 H, m), 1.50–1.82 (4 H, m), 2.31 (2 H, t, J=6 Hz), 2.46 (2 H, d, J=5 Hz), 4.14 (1 H, m), 4.39 (2 H, m), 5.01 (1 H, d, J=7 Hz), 5.06 (2 H, s), 5.27 (1 H, m), 6.41 (1 H, m), 7.22–7.41 (10 H, m)

EXAMPLE 13

(3S)-3-[(2S)-5-Benzyloxycarbonyl-2-(5-dimethylamino-1-naphthylsulfonylamino)pentanoyl]oxyhexadecanamide was obtained according to a similar manner to that of Example 2.

NMR (CDCl$_3$, δ): 0.88 (3 H, t, J=6 Hz), 0.98–1.72 (28 H, m), 2.11–2.26 (4 H, m), 2.86 (6 H, s), 3.83 (1 H, m), 4.99 (1 H, m), 5.05 (2 H, s), 5.28 (1 H, br s), 5.54 (1 H, d, J=8 Hz), 5.61 (1 H, br s), 7.17 (1 H, d, J=7 Hz), 7.26–7.40 (5 H, m), 7.45–7.61 (2 H, m), 8.22 (1 H, d, J=7 Hz), 8.27 (1 H, d, J=8 Hz), 8.53 (1 H, d, J=8 Hz)

EXAMPLE 14

To a solution of (3S)-3-[(2S)-5-benzyloxycarbonyl-2-aminopentanoyl]oxyhexadecanamide hydrochloride (2.17 g) in dichloromethane (8 ml) were added phenyl chlorocarbonate (0.65 ml) and triethylamine (1.68 ml). This mixture was stirred at room temperature overnight, and then poured into a mixture of ethyl acetate (80 ml) and 1N hydrochloric acid (80 ml). The organic layer was washed with water, saturated aqueous sodium bicarbonate, and brine successively. This solution was dried and evaporated to dryness. The residue was chromatographed on silica gel (200 cc) eluting with a mixture of dichloromethane and methanol (20:1) to give (3S)-3-[(2S)-5-benzyloxycarbonyl-2-(phenoxycarbonylamino)-pentanoyl]oxyhexadecanamide (1.73 g).

NMR (CDCl$_3$, δ): 0.87 (3 H, t, J=7 Hz), 1.12–1.48 (22 H, m), 1.54–2.03 (6 H, m), 2.46–2.54 (4 H, m), 4.38 (1 H, m), 5.12 (2 H, s), 5.30. (H, m), 5.69 (1 H, d, J=7 Hz), 5.76 (1 H, br s), 7.13 (2 H, d, J=8 Hz), 7.22 (1 H, dd, J=7 Hz, 7 Hz), 7.29–7.52 (7 H, m)

The following compounds (Examples 15 to 17) were obtained according to a similar manner to that of Example 14.

EXAMPLE 15

(3S)-3-[(2S)-5-Carboxy-2-{(2E,4E)-hexadienoylamino}-pentanoyl]oxyhexadecanamide

NMR (CD$_3$OD, δ): 0.88 (3 H, t, J=7 Hz), 1.07–1.45 (22 H, m), 1.48–1.99 (6 H, m), 1.83 (3 H, t, J=6 Hz), 2.22–2.60 (4 H, m), 4.42 (1 H, m), 5.25 (1 H, m), 5.97 (1 H, d, J=15 Hz), 6.13 (1 H, dt, J=15 Hz, 6 Hz), 6.23 (1 H, dd, J=10 Hz, 15 Hz), 7.24 (1 H, dd, J=10 Hz, 15 Hz)

EXAMPLE 16

(3S)-3-[(2S)-5-Carboxy-2-cinnamoylaminopentanoyl]-oxyhexadecanamide

NMR (CD$_3$OD, δ): 0.88 (3 H, t, J=7 Hz), 1.09–1.53 (22 H, m), 1.53–2.03 (6 H, m), 2.34 (2 H, m), 2.49 (2 H, m), 4.48 (1 H, m), 5.39 (1 H, m), 6.49 (1 H, d, J=21 Hz), 7.33–7.45 (3 H, m), 7.49–7.62 (3 H, m)

EXAMPLE 17

(3S)-3-[(2S)-5-Carboxy-2-(crotonoylamino)pentanoyl]-oxyhexadecanamide

NMR (CDCl$_3$—CD$_3$OD (20:1), δ): 0.85 (3 H, t, J=6 Hz), 1.14–1.50 (22 H, m), 1.50–1.78 (6 H, m), 1.85 (3 H, d, J=7 Hz), 2.30 (2 H, m), 2.46 (2 H, d, J=6 Hz), 4.55 (1 H, m), 5.24 (1 H, m), 5.87 (1 H, dd, J=14 Hz, 2 Hz), 6.83 (1 H, m)

EXAMPLE 18

A solution of (3S)-3-[(2S)-5-benzyloxycarbonyl-2-(phenoxycarbonylamino)pentanoyl]oxyhexadecanamide (1.70 g) and 2-aminopyridine (2.56 g) in pyridine (10 ml) was stirred at 70° C. for 64 hours, and then poured into a mixture of ethyl acetate (100 ml) and 1N hydrochloric acid (100 ml). The organic phase was washed with 1N hydrochloric acid (100 ml), 0.5N hydrochloric acid (100 ml), saturated aqueous sodium bicarbonate (100 ml), and brine (50 ml) successively, dried over magnesium sulfate, and evaporated to dryness. The residue was chromatographed on silica gel (300 cc) eluting with a mixture of dichloromethane and acetone (2:1 - 1:1) to give (3S)-3-[(2S)-5-benzyloxycarbonyl-2-{3-(2-pyridyl)ureido}pentanoyl] oxyhexadecanamide (1.14 g).

NMR (CDCl$_3$, δ): 0.87 (3 H, t, J=7 Hz), 1.00–1.40 (22 H, m), 1.48–2.12 (6 H, m), 2.33–2.57 (4 H, m), 4.54 (1 H, m), 5.12 (2 H, s), 5.22 (1 H, m), 6.08 (1 H, br s), 6.30 (1 H, br s), 6.82 (1 H, d, J=7 Hz), 6.89 (1 H, dd, J=5 Hz, 5 Hz), 7.27–7.42 (5 H, m), 7.60 (1 H, dd, J=5 Hz, 7 Hz), 8.19 (1 H, d, J=5 Hz), 8.48 (1 H, s)

EXAMPLE 19

(3S)-3-[(2S)-5-Benzyloxycarbonyl-2-{3-(2-pyridylmethyl)ureido}pentanoyl]oxyhexadecanamide was obtained according to a similar manner to that of Example 18.

NMR (CDCl$_3$, δ): 0.88 (3 H, t, J=7 Hz), 1.15–1.38 (22 H, m), 1.50–1.90 (6 H, m), 2.33–2.52 (4 H, m), 4.41 (1 H, m), 4.47 (1 H, m), 5.12 (2 H, s), 5.21 (1 H, m), 5.52 (1 H, br s), 5.68 (1 H, m), 6.13 (1 H, br s), 7.20 (1 H, dd, J=5 Hz, 8 Hz), 7.27 (1 H, d, J=8 Hz), 7.34 (5 H, m), 7.67 (1 H, t, J=8 Hz), 8.52 (1 H, d, J=5 Hz)

The following compounds (Examples 20 to 25) were obtained according to a similar manner to that of Example 6.

EXAMPLE 20

(3S)-3-[(2S)-5-Carboxy-2-(phenoxycarbonylamino)-pentanoyl]oxyhexadecanamide

NMR (CDCl$_3$, δ): 0.88 (3 H, t, J=7 Hz), 1.06–1.43 (22 H, m), 1.50–2.10 (6 H, m), 2.27–2.69 (4 H, m), 4.41 (1 H, m), 5.34 (1 H, br s), 5.90 (1 H, d, J=8 Hz), 6.12 (1 H, br s), 7.09 (1 H, br s), 7.12 (2 H, d, J=8 Hz), 7.21 (1 H, t, J=8 Hz), 7.36 (2 H, t, J=8 Hz)

EXAMPLE 21

(3S)-3-[(2S)-5-Carboxy-2-{3-(2-pyridyl)ureido}-pentanoyl]oxyhexadecanamide

NMR (CDCl$_3$—CD$_3$OD (20:1), δ): 0.88 (3 H, t, J=7 Hz), 1.13–1.43 (22 H, m), 1.55–2.07 (6 H, m), 2.37 (2 H, m), 2.49 (2 H, d, J=7 Hz), 4.54 (1 H, dd, J=6 Hz, 7 Hz), 5.26 (1 H, m), 7.92 (1 H, dd, J=5 Hz, 7 Hz), 7.03 (1 H, d, J=8 Hz), 7.62 (1 H, dd, J=7 Hz, 8 Hz), 8.21 (1 H, d, J=5 Hz)

EXAMPLE 22

(3S)-3-[(2S)-5-Carboxy-2-{3-(2-pyridylmethyl)ureido}pentanoyl]oxyhexadecanamide

NMR (CDCl$_3$—CD$_3$OD (10:1), δ): 0.88 (3 H, t, J=7 Hz), 1.07–1.40 (22 H, m), 1.46–1.93 (6 H, m), 2.05–2.56 (4 H, m), 4.40 (1 H, m), 4.45 (2 H, s), 5.23 (1 H, m), 7.22 (1 H, dd, J=5 Hz, 8 Hz), 7.34 (1 H, d, J=8 Hz), 7.70 (1 H, t, J=8 Hz), 8.48 (1 H, d, J=5 Hz)

EXAMPLE 23

(3S)-3-[(2S)-5-Carboxy-2-{(5-dimethylamino-1-naphthyl)sulfonylamino}pentanoyl]oxyhexadecanamide NMR (CDCl$_3$, δ): 0.89 (3 H, t, J=7 Hz), 0.95–1.70 (28 H, m), 2.20–2.36 (4 H, m), 2.87 (6 H, s), 3.89 (1 H, m), 5.03 (1 H, m), 5.93 (1 H, br s), 6.04 (1 H, br s), 6.82 (1 H, br s), 7.18 (1 H, d, J=8 Hz), 7.42–7.61 (2 H, m), 8.21 (1 H, d, J=7 Hz), 8.28 (1 H, d, J=8 Hz), 8.53 (1 H, d, J=8 Hz)

EXAMPLE 24

(3S)-N-Methyl-3-[(2S)-5-carboxy-2-(tertiarybutoxycarbonylamino)pentanoyl] oxyhexadecanamide NMR (CDCl$_3$, δ): 0.88 (3 H, t, J=6 Hz), 1.15–1.37 (22 H, m), 1.44 (9 H, s), 1.54–2.43 (6 H, m), 2.29–2.51 (4 H, m), 2.78 (3 H, d, J=4 Hz), 4.25 (1 H, m), 5.14 (1 H, d, J=7 Hz), 5.24 (1 H, m), 6.13 (1 H, br s)

EXAMPLE 25

(3S)-N-Benzyl-3-[(2S)-5-carboxy-2-(tertiarybutoxycarbonylamino)pentanoyl] oxyhexadecanamide NMR (CDCl$_3$, δ): 0.87 (3 H, t, J=6 Hz), 1.43 (9 H, s), 1.15–1.83 (28 H, m), 2.29 (2 H, m), 2.48 (2 H, d, J=7 Hz), 4.16 (1 H, m), 4.41 (2 H, m), 5.06 (1 H, d, J=8 Hz), 5.26 (1 H, m), 6.37 (1 H, m), 7.16–7.39 (5 H, m)

EXAMPLE 26

To a solution of (3S)-3-[(2S)-5-benzyloxycarbonyl-2-aminopentanoyl]oxyhexadecanamide hydrochloride (1.79 g), 3-quinolinecarboxylic acid (630 mg) and 1-hydroxybenzotriazole (536 mg) in N,N-dimethylformamide (40 ml) was added 1-ethyl-3-(3-dimethylaminopropyl)carbodiimide (616 mg) at 0° C., and the mixture was stirred at room temperature for 2 hours. The solution was diluted with ethyl acetate (200 ml) and washed with 0.5N hydrochloric acid (200 ml), 10% aqueous citric acid (200 ml), saturated aqueous sodium bicarbonate (200 ml) and brine, successively. The organic layer was dried over magnesium sulfate and evaporated in vacuo to give (3S)-3-[(2S)-5-benzyloxycarbonyl-2-{(3-quinolyl)carbonylamino}pentanoyl]oxyhexadecanamide (2.16 g).

mp 85–87° C.

NMR (CDCl$_3$, δ): 9.35 (1 H, s), 8.62 (1 H, s), 8.16 (1 H, d, J=10 Hz), 7.90 (1 H, d, J=10 Hz), 7.32 (1 H, t, J=10 Hz), 7.12 (1 H, t, J=10 Hz), 7.28–7.40 (5 H, m), 5.92 (1 H, br s), 5.46 (1 H, br s), 5.35 (1 H, m), 5.12 (2 H, s), 4.30 (1 H, m), 2.40–2.54 (4 H, m), 1.6–2.1 (6 H, m), 1.1–1.4 (22 H, m), 0.88 (3 H, t, J=7 Hz)

FAB-MS: 660 (M+H)

EXAMPLE 27

To a solution of (3S)-3-[(2S)-5-benzyloxycarbonyl-2-{(3-quinolyl)carbonylamino}pentanoyl]-oxyhexadecanamide (1.97 g) and anisole (9.73 ml) in dichloromethane (40 ml) was added dropwise aluminum chloride (3.98.g) in nitromethane (40 ml) at 0° C., and the mixture was stirred at room temperature for 2 hours. The solution was diluted with ethyl acetate (200 ml) and washed with 10% aqueous citric acid (200 ml), water (20 ml) and brine (200 ml), successively. The organic layer was dried over magnesium sulfate and evaporated in vacuo. The resulting crystalline was triturated with diethyl ether to give (3S)-3-[(2S)-5-carboxy-2-{(3-quinolyl)carbonylamino}pentanoyl]oxyhexadecanamide (2.16 g).

mp : 113–120° C.

NMR (DMSO-d$_6$, δ): 9.30 (1 H, d, J=2 Hz), 9.10 (1 H, d, J=7 Hz), 8.86 (1 H, d, J=2 Hz), 8.10 (1 H, d, J=5 Hz), 8.07 (1 H, d, J=5 Hz), 7.87 (1 H, t, J=7 Hz), 7.70 (1 H, t, J=7 Hz), 7.35 (1 H, s), 6.84 (1 H, s), 5.15 (1 H, m), 4.42 (1H m), 2.2–2.45 (4 H, m), 1.4–1.9 (6 H, m), 1.1–1.35 (22 H, m), 0.85 (3 H, t, J=7 Hz)

FAB-MS: 570 (M+H)

EXAMPLE 28

To a solution of (3S)-3-[(2S)-5-benzyloxycarbonyl-2-aminopentanoyl]oxyhexadecanamide hydrochloride (0.20 g) and 2-pyridinecarbaldehyde (79.2 mg) in methanol (4 ml) was added sodium cyanoborohydride (46.4 mg) at room temperature and the mixture was stirred at the same temperature for 30 minutes. The solution was diluted with ethyl acetate (20 ml) and washed with saturated aqueous sodium bicarbonate (20 ml×2) and brine (20 ml×2), successively. The organic layer was dried over magnesium sulfate and concentrated in vacuo. The residue was purified by thin layered chromatography (10% methanol in chloroform) to give (3S)-3-[(2S)-5-benzyloxycarbonyl-2-(2-pyridylmethylamino)pentanoyl]-oxyhexadecanamide (0.25 g).

NMR (CDCl$_3$, δ): 8.52 (1 H, dd, J=5.2 Hz), 7.64 (1 H, dd, J=7.5 Hz), 7.3–7.4 (6 H, m), 6.16 (1 H, br s), 5.38 (1 H, br s), 5.26 (1 H, m), 5.10 (2 H, s), 3.85 (2 H, ABq), 3.30 (1 H, m), 2.50 (2 H, d, J=7 Hz), 2.38 (2 H, m), 1.4–1.9 (6 H, m), 1.2–1.4 (22 H, m), 0.90 (3 H, t, J=7 Hz)

EXAMPLE 29

(3S)-3-[(2S)-5-Benzyloxycarbonyl-2-(phenoxycarbonylamino)pentanoyl]oxyhexadecanenitrile was obtained according to a similar manner to that of Example 14.

NMR (CDCl$_3$, δ): 7.31–7.44 (7 H, m), 7.21 (1 H, t, J=7 Hz), 7.14 (2 H, d, J=8 Hz), 5.60 (1 H, d, J=7 Hz), 5.13 (2 H, s), 5.06 (1 H, m), 4.44 (1 H, m), 2.74 (1 H, dd, J=16 Hz, 5 Hz), 2.60 (1 H, dd, J=16 Hz, 6 Hz), 2.45 (2 H, m), 1.61–2.05 (6 H, m), 1.15–1.41 (22 H, m), 0.88 (3 H, t, J=7 Hz)

EXAMPLE 30

(3R)-3-[(2R)-5-Benzyloxycarbonyl-2-{3-(2-pyridyl)ureido}pentanoyl]oxyhexadecanamide was obtained according to a similar manner to that of Example 18.

NMR (CDCl$_3$, δ): 8.48 (1 H, s), 8.19 (1 H, d, J=5 Hz), 7.60 (1 H, dd, J=7 Hz, 5 Hz), 7.27–7.42 (5 H, m), 6.89 (1 H, dd, J=5 Hz, 5 Hz), 6.82 (1 H, d, J=7 Hz), 6.30 (1 H, br s), 6.08 (1 H, br s), 5.22 (1 H, m), 5.12 (2 H, s), 4.54 (1 H, m), 2.33–2.57 (4 H, m), 1.48–2.12 (6 H, m), 1.00–1.40 (22 H, m), 0.87 (3 H, t, J=7 Hz)

EXAMPLE 31

To a solution of (3S)-(2,2,2-trichloroethyl) 3-[(2S)-5-benzyloxycarbonyl-2-{3-methyl-3-(2-pyridyl)ureido}pentanoyl]oxyhexadecanoate (240 mg) in aqueous 80% acetic acid was added zinc powder (203 mg). This mixture was stirred at room temperature for an hour. Then, the insoluble powder was filtered off with celite. After evaporation, the residue was dissolved in ethyl acetate (20 ml) and washed with water (20 ml×2) and brine (20 ml). This solution was dried over magnesium sulfate and evaporated to dryness, and redissolved in tetrahydrofuran (2 ml). To this solution was added 1-ethyl-3-(3-dimethylaminopropyl)carbodiimide hydrochloride (50 mg) and 1-hydroxybenzotriazole (71 mg). After stirring for 30 minutes, 28% ammonium hydroxide (90 μl) was added and the mixture was stirred at room temperature overnight. Then, the mixture was diluted with ethyl acetate (20 ml) and washed with 1N-hydrochloric acid (20 ml×2), saturated sodium bicarbonate (20 ml), and brine (20 ml). After drying over magnesium sulfate and evaporation, the residue was chromatographed on a silica gel to give (3S)-3-[(2S)-5-benzyloxycarbonyl-2-{3-methyl-3-(2-pyridyl)ureido}pentanoyl]oxyhexadecanamide (145 mg).

NMR (CDCl$_3$, δ): 8.29 (1 H, m), 7.72 (1 H, m), 7.34 (5 H, m), 6.92–7.03 (2 H, m), 6.20 (1 H, m), 5.17–5.28 (2 H, m), 5.10 (2 H, s), 4.52 (1 H, m), 3.38 (3 H, s), 2.38–2.52 (4 H, m), 1.48–2.03 (6 H, m), 1.14–1.36 (22 H, m), 8.88 (3 H, t, J=7 Hz)

The following compounds (Examples 32 to 42) were obtained according to a similar manner to that of Example 31.

EXAMPLE 32

(3S)-3-[(2S)-5-Benzyloxycarbonyl-2-(piperidinocarbonylamino)pentanoyl]oxyhexadecanamide NMR (CDCl$_3$, δ): 7.35 (5 H, m), 6.21 (1 H, br s), 5.28 (1 H, br s), 5.22 (1 H, br s), 5.11 (2 H, s), 4.40 (1 H, m), 3.34 (4 H, m), 2.31–2.53 (4 H, m), 1.42–1.95 (12 H, m), 1.06–1.34 (22 H, m), 0.87 (3 H, t, J=7 Hz)

EXAMPLE 33

(3S)-3-[(2S)-5-Benzyloxycarbonyl-2-{4-(3,4-methylenedioxybenzyl)-1-piperazinylcarbonylamino}-pentanoyl]oxyhexadecanamide NMR (CDCl$_3$, δ): 7.35 (5 H, m), 6.86 (1 H, s), 6.77 (1 H, d, J=9 Hz), 6.73 (1 H, d, J=9 Hz), 6.11 (1 H, br s), 5.95 (2 H, s), 5.25 (1 H, br s), 5.23 (1 H, m), 5.17 (1 H, d, J=7 Hz), 5.11 (2 H, s), 4.39 (1 H, m), 3.33–3.46 (6 H, m), 2.32–2.50 (8 H, m), 1.53–1.93 (6 H, m), 1.14–1.37 (22 H, m), 0.88 (3 H, t, J=7 Hz)

EXAMPLE 34

(3S)-3-[(2S)-5-Benzyloxycarbonyl-2-(morpholinocarbonylamino)pentanoyl]oxyhexadecanamide NMR (CDCl$_3$, δ): 7.35 (5 H, m), 6.01 (1 H, br s), 5.19–5.34 (3 H, m), 5.12 (2 H, s), 4.42 (1 H, m), 3.68 (4 H, m), 3.37 (4 H, m), 2.37–2.53 (4 H, m), 1.50–1.95 (6 H, m), 1.16–1.37 (22 H, m), 0.88 (3 H, t, J=7 Hz)

EXAMPLE 35

(3S)-3-[(2S)-5-Benzyloxycarbonyl-2-{3-((2S)-2-hydroxypropyl)ureido}pentanoyl]oxyhexadecanamide NMR (DMSO-d$_6$, δ): 7.35 (5 H, m), 6.83 (1 H, br s), 6.35 (1 H, d, J=8 Hz), 6.04 (1 H, t, J=6 Hz), 5.08 (2 H, s), 5.08 (1 H, m), 4.09 (1 H, m), 3.57 (1 H, m), 3.00 (1 H, m), 2.85 (1 H, m), 2.23–2.40 (4 H, m), 1.36–1.71 (6 H, m), 1.08–1.31 (22 H, m), 0.98 (3 H, d, J=7 Hz), 0.84 (3 H, t, J=7 Hz)

EXAMPLE 36

(3S)-3-[(2S)-5-Benzyloxycarbonyl-2-(3-morpholinoureido)pentanoyl]oxyhexadecanamide NMR (CDCl$_3$, δ): 7.35 (5 H, m), 6.53 (1 H, d, J=8 Hz), 5.95 (1 H, br s), 5.32 (1 H, br s), 5.23 (1 H, m), 5.11 (2 H, s), 4.42 (1 H, m), 3.58–3.94 (4 H, m), 2.35–3.11 (8 H, m), 1.52–2.00 (6 H, m), 1.16–1.38 (22 H, m), 0.88 (3 H, t, J=7 Hz)

EXAMPLE 37

(3S)-3-[(2S)-5-Benzyloxycarbonyl-2-{3-(5-chloro-2-pyridyl)ureido}pentanoyl]oxyhexadecanamide NMR (CDCl$_3$, δ): 9.51 (1 H, d, J=7 Hz), 8.85 (1 H, br s), 8.16 (1 H, d, J=2 Hz), 7.55 (1 H, dd, J=8 Hz, 2 Hz), 7.34 (5 H, m), 6.85 (1 H, d, J=8 Hz), 6.30 (1 H, br s), 6.24 (1 H, br s), 5.20 (1 H, m), 5.12 (2 H, s), 4.51 (1 H, m), 2.47–2.57 (2 H, m), 2.44 (2 H, t, J=7 Hz), 1.52–2.06 (6 H, m), 1.10–1.36 (22 H, m), 0.88 (3 H, t, J=7 Hz)

EXAMPLE 38

(3S)-3-[(2S)-5-Benzyloxycarbonyl-2-{3-(5-methyl-2-pyridyl)ureido}pentanoyl]oxyhexadecanamide NMR (CDCl$_3$, δ): 8.02 (1 H, d, J=2 Hz), 7.89 (1 H, br s), 7.42 (1 H, dd, J=8 Hz, 2 Hz), 7.35 (5 H, m), 6.67 (1 H, d, J=8 Hz), 6.29 (1 H, br s), 5.86 (1 H, br s), 5.20 (1 H, m), 5.12 (2 H, s), 4.53 (1 H, m), 2.39–2.52 (4 H, m), 2.25 (3 H, s), 1.48–2.08 (6 H, m), 1.12–1.37 (22 H, m), 0.87 (3 H, t, J=7 Hz)

EXAMPLE 39

(3S)-3-[(2S)-5-Benzyloxycarbonyl-2-{3-(2-quinolyl)ureido}pentanoyl]oxyhexadecanamide NMR (DMSO-d$_6$, δ): 9.99 (1 H, s), 8.24 (1 H, d, J=8 Hz), 7.84 (1 H, d, J=8 Hz), 7.75 (1 H, d, J=8 Hz), 7.65 (1 H, dd, J=8 Hz, 7 Hz), 7.43 (1 H, dd, J=8 Hz, 7 Hz), 7.37 (1 H, br s), 7.30 (5 H, m), 6.86 (1 H, br s), 5.18 (1 H, m), 5.08 (2 H, s), 4.39 (1 H, m), 2.36–2.49 (4 H, m), 1.47–1.97 (6 H, m), 1.12–1.43 (22 H, m), 0.85 (3 H, t, J=7 Hz)

EXAMPLE 40

(3S)-3-[(2S)-5-Benzyloxycarbonyl-2-{3-(3-quinolyl)ureido}pentanoyl]oxyhexadecanamide NMR (DMSO-d$_6$, δ): 9.12 (1 H, br s), 8.75 (1 H, d, J=2 Hz), 8.46 (1 H, d, J=2 Hz), 7.90 (1 H, d, J=8 Hz), 7.82 (1 H, d, J=8 Hz), 7.57 (1 H, dd, J=8 Hz, 6 Hz), 7.52 (1 H, dd, J=8 Hz, 6 Hz), 7.35 (5 H, m), 6.85 (2 H, m), 5.16 (1 H, m), 5.10 (2 H, s), 4.23 (1 H, m), 2.27–2.49 (4 H, m), 1.42–1.85 (6 H, m), 0.98–1.37 (22 H, m), 0.84 (3 H, t, J=7 Hz)

EXAMPLE 41

(3S)-3-[(2S)-5-Benzyloxycarbonyl-2-{3-(2-benzothiazolyl)ureido}pentanoyl]oxyhexadecanamide NMR (CDCl$_3$, δ): 7.70 (1 H, d, J=8 Hz), 7.65 (1 H, d, J=8 Hz), 7.19–7.40 (7 H, m), 6.52 (1 H, br s), 6.10 (1 H, br s), 5.37 (1 H, m), 5.07 (2 H, s), 4.53 (1 H, m), 2.45–2.59 (2 H, m), 2.40 (2 H, t, J=7 Hz), 1.49–2.05 (6 H, m), 1.10–1.37 (22 H, m), 0.86 (3 H, t, J=7 Hz)

EXAMPLE 42

(3S)-3-[(2S)-5-Benzyloxycarbonyl-2-{3-(5-chloro-2-benzoxazolyl)ureido}pentanoyl]oxyhexadecanamide NMR (CDCl$_3$, δ): 9.21 (1 H, br s), 9.11 (1 H, d, J=7 Hz), 7.52 (1 H, d, J=2 Hz), 7.28–7.37 (6 H, m), 7.18 (1 H, dd, J=8 Hz, 2 Hz), 6.22 (1 H, br s), 6.12 (1 H, br s), 5.25 (1 H, m), 5.12 (2 H, s), 4.53 (1 H, m), 2.54 (2 H, m), 2.47 (2 H, t, J=7 Hz), 1.60–2.06 (6 H, m), 1.16–1.37 (22 H, m), 0.87 (3 H, t, J=7 Hz)

EXAMPLE 43

A solution of (3S)-(2,2,2-trichloroethyl) 3-[(2S)-5-benzyloxycarbonyl-2-isocyanatopentanoyl]oxyhexadecanoate (0.33 g) and 2-(methylamino)pyridine (113 mg) in dichloromethane (5 ml) was stirred at room temperature overnight. The mixture was poured into ethyl acetate (20 ml), and washed with aqueous 1 N-hydrochloric acid (20 ml×2), saturated sodium bicarbonate (20 ml), and brine (20 ml). Then, the solution was dried over magnesium sulfate, and evaporated to dryness. The residue was chromatographed on a silica gel to give (3S)-(2,2,2-trichloroethyl) 3-[(2S)-5-benzyloxycarbonyl-2-{3-methyl-3-(2-pyridyl)ureido}pentanoyl]oxyhexadecanoate (0.25 g).

NMR (CDCl$_3$, δ): 8.28 (1 H, m), 7.70 (1 H, m), 7.34 (5 H, m), 6.91–7.01 (2 H, m), 5.30 (1 H, m), 5.11 (2 H, s), 4.76 (1 H, d, J=12 Hz), 4.70 (1 H, d, J=12 Hz), 4.58 (1 H, m), 3.38 (3 H, s), 2.78 (1 H, dd, J=16 Hz, 7 Hz), 2.71 (1 H, dd, J=16 Hz, 6 Hz), 2.51 (2 H, t, J=7 Hz), 1.51–1.99 (6 H, m), 1.12–1.38 (22 H, m), 0.87 (3 H, t, J=7 Hz)

The following compounds (Examples 44 to 54) were obtained according to a similar manner to that of Example 43.

EXAMPLE 44

(3S)-(2,2,2-Trichloroethyl) 3-[(2S)-5-benzyloxycarbonyl-2-{3-((2S)-2-hydroxypropyl)ureido}pentanoyl]oxyhexadecanoate NMR (CDCl$_3$, δ): 7.37 (5 H, m), 5.29 (1 H, m), 5.12 (2 H, s), 4.77 (1 H, d, J=12 Hz), 4.71 (1 H, d, J=12 Hz), 4.43 (1 H, m), 3.91 (1 H, m), 3.31 (1 H, m), 3.05 (1 H, m), 2.74

(2 H, m), 2.38 (2 H, m), 1.45–1.90 (6 H, m), 1.20–1.37 (22 H, m), 1.18 (3 H, d, J=7 Hz), 0.88 (3 H, t, J=7 Hz)

EXAMPLE 45

(3S)-(2,2,2-Trichloroethyl) 3-[(2S)-5-benzyloxycarbonyl-2-{3-(5-chloro-2-pyridyl)ureido}pentanoyl]oxyhexadecanoate NMR (CDCl$_3$, δ): 9.48 (1 H, d, J=7 Hz), 8.20 (1 H, d, J=2 Hz), 7.77 (1 H, s), 7.55 (1 H, dd, J=8 Hz), 7.34 (5 H, m), 6.75 (1 H, d, J=8 Hz), 5.32 (1 H, m), 5.11 (2 H, s), 4.76 (1 H, d, J=12 Hz), 4.70 (1 H, d, J=12 Hz), 4.62 (1 H, m), 2.75 (2 H, m), 2.42 (2 H, t, J=7 Hz), 1.61–2.07 (6 H, m), 1.14–1.40 (22 H, m), 0.88 (3 H, t, J=7 Hz)

EXAMPLE 46

(3S)-(2,2,2-Trichloroethyl) 3-[(2S)-5-benzyloxycarbonyl-2-{3-(5-methyl-2-pyridyl)ureido}pentanoyl]oxyhexadecanoate NMR (CDCl$_3$, δ): 8.04 (1 H, d, J=2 Hz), 7.40 (1 H, dd, J=8 Hz, 2 Hz), 7.33 (5 H, m), 6.98 (1 H, s), 6.56 (1 H, d, J=8 Hz), 5.31 (1 H, m), 5.10 (2 H, s), 4.75 (1 H, d, J=12 Hz), 4.70 (1 H, d, J=12 Hz), 4.62 (1 H, m), 2.78 (1 H, dd, J=16 Hz, 7 Hz), 2.21 (1 H, dd, J=16 Hz, 6 Hz), 2.42 (2 H, t, J=7 Hz), 2.25 (3 H, s), 1.60–2.02 (6 H, m), 1.14–1.40 (22 H, m), 0.88 (3 H, t, J=7 Hz)

EXAMPLE 47

(3S)-(2,2,2-Trichloroethyl) 3-[(2S)-5-benzyloxycarbonyl-2-{3-(2-quinolyl)ureido}pentanoyl]oxyhexadecanoate NMR (CDCl$_3$, δ): 8.03 (1 H, d, J=8 Hz), 7.88 (1 H, d, J=8 Hz), 7.70 (1 H, d, J=8 Hz), 7.59–7.68 (2 H, m), 7.42 (1 H, dd, J=7 Hz, 8 Hz), 7.30 (5 H, m), 6.80 (1 H, d, J=8 Hz), 5.36 (1 H, m), 5.10 (2 H, s), 4.76 (1 H, d, J=12 Hz), 4.71 (1 H, d, J=12 Hz), 4.69 (1 H, m), 2.80 (1 H, dd, J=16 Hz, 7 Hz), 2.73 (1 H, dd, J=16 Hz, 6 Hz), 2.46 (2 H, t, J=7 Hz), 1.60–2.09 (6 H, m), 1.09–1.40 (22 H, m), 0.86 (3 H, t, J=7 Hz)

EXAMPLE 48

(3S)-(2,2,2-Trichloroethyl) 3-[(2S)-5-benzyloxycarbonyl-2-{3-(3-quinolyl)ureido}pentanoyl]oxyhexadecanoate NMR (CDCl$_3$, δ): 9.14 (1 H, br s), 8.75 (1 H, d, J=3 Hz), 8.44 (1 H, d, J=3 Hz), 7.89 (1 H, d, J=8 Hz), 7.80 (1 H, d, J=8 Hz), 7.46–7.60 (2 H, m), 7.35 (5 H, m), 6.91 (1 H, d, J=8 Hz), 5.20 (1 H, m), 5.10 (2 H, s), 4.86 (1 H, d, J=12 Hz), 4.81 (1 H, d, J=12 Hz), 4.21 (1 H, m), 2.87 (1 H, dd, J=16 Hz, 6 Hz), 2.76 (1 H, dd, J=16 Hz, 7 Hz), 2.41 (2 H, t, J=7 Hz), 1.50–1.84 (6 H, m), 1.02–1.38 (22 H, m), 0.84 (3 H, t, J=7 Hz)

EXAMPLE 49

(3S)-(2,2,2-Trichloroethyl) 3-[(2S)-5-benzyloxycarbonyl-2-{3-(2-benzothiazolyl)ureido}pentanoyl]oxyhexadecanoate NMR (CDCl$_3$, δ): 7.75 (1 H, d, J=8 Hz), 7.70 (1 H, d, J=8 Hz) 7.27–7.42 (7 H, m), 5.34 (1 H, m), 5.19 (2 H, s), 4.75 (1 H, d, J=12 Hz), 4.70 (1 H, d, J=12 Hz), 4.52 (1 H, m), 2.75 (2 H, m), 2.42 (2 H, t, J=7 Hz), 1.50–2.06 (6 H, m), 1.14–1.40 (22 H, m), 0.87 (3 H, t, J=7 Hz)

EXAMPLE 50

(3S)-(2,2,2-Trichloroethyl) 3-[(2S)-5-benzyloxycarbonyl-2-{3-(5-chloro-2-benzoxazolyl)ureido}pentanoyl]-oxyhexadecanoate NMR (CDCl$_3$, δ): 9.06 (1 H, d, J=8 Hz), 8.10 (1 H, s), 7.53 (1 H, d, J=2 Hz), 7.27–7.38 (6 H, m), 7.18 (1 H, dd, J=8 Hz, 2 Hz), 5.35 (1 H, m), 5.11 (2 H, s), 4.75 (1 H, d, J=12 Hz), 4.70 (1 H, d, J=12 Hz), 4.61 (1 H, m), 2.77 (2 H, m), 2.43 (2 H, t, J=7 Hz), 1.59–2.09 (6 H, m), 1.15–1.44 (22 H, m), 0.87 (3 H, t, J=7 Hz)

EXAMPLE 51

(3S)-(2,2,2-Trichloroethyl) 3-[(2S)-5-benzyloxycarbonyl-2-(3-morpholinoureido)pentanoyl]oxyhexadecanoate NMR (CDCl$_3$, δ): 7.34 (5 H, m), 6.50 (1 H, d, J=8 Hz), 5.28 (1 H, m), 5.16 (1 H, br s), 5.10 (2 H, s), 4.77 (1 H, d, J=12 Hz), 4.70 (1 H, d, J=12 Hz), 4.47 (1 H, m), 3.60–3.92 (4 H, m), 2.48–3.13 (4 H, m), 2.38 (2 H, m), 1.58–1.94 (6 H, m), 1.16–1.40 (22 H, m), 0.87 (3 H, t, J=7 Hz)

EXAMPLE 52

(3S)-(2,2,2-Trichloroethyl) 3-[(2S)-5-benzyloxycarbonyl-2-(piperidinocarbonylamino)pentanoyl]oxyhexadecanoate NMR (CDCl$_3$, δ): 7.35 (5 H, m), 5.29 (1 H, m), 5.11 (2 H, s), 5.02 (1 H, d, J=7 Hz), 4.77 (1 H, d, J=12 Hz), 4.70 (1 H, d, J=12 Hz), 4.49 (1 H, m), 3.33 (4 H, m), 2.77 (1 H, dd, J=15 Hz, 7 Hz), 2.70 (1 H, dd, J=15 Hz, 6 Hz), 2.39 (2 H, t, J=7 Hz), 1.48–1.96 (12 H, m), 1.15–1.43 (22 H, m), 0.88 (3 H, t, J=7 Hz)

EXAMPLE 53

(3S)-(2,2,2-Trichloroethyl) 3-[(2S)-5-benzyloxycarbonyl-2-{4-(3,4-methylenedioxybenzyl-1-piperazinylcarbonylamino}-pentanoyl]oxyhexadecanoate NMR (CDCl$_3$, δ): 7.34 (5 H, m), 6.85 (1 H, s), 6.76 (1 H, d, J=9 Hz), 6.73 (1 H, d, J=9 Hz), 5.95 (2 H, s), 5.28 (1 H, m), 5.10 (1 H, s), 5.04 (1 H, d, J=8 Hz), 4.77 (1 H, d, J=12 Hz), 4.70 (1 H, d, J=12 Hz), 3.32–3.46 (6 H, m), 2.73 (2 H, m), 2.31–2.46 (6 H, m), 1.55–1.92 (6 H, m), 1.13–1.41 (22 H, m), 0.88 (3 H, t, J=7 Hz)

EXAMPLE 54

(3S)-2,2,2-Trichloroethyl) 3-[(2S)-5-benzyloxycarbonyl-2-(morpholinocarbonylamino)pentanoyl]oxyhexadecanoate NMR (CDCl$_3$, δ): 7.35 (5 H, m), 5.29 (1 H, m), 5.21 (2 H, s), 5.08 (1 H, d, J=7 Hz), 4.77 (1 H, d, J=12 Hz), 4.70 (1 H, d, J=12 Hz), 4.47 (1 H, m), 3.69 (4 H, m), 3.37 (4 H, m), 2.73 (2 H, m), 2.38 (2 H, m), 1.50–1.90 (6 H, m), 1.15–1.27 (22H., m), 0.88 (3 H, t, J=7 Hz)

EXAMPLE 55

(3R)-3-[(2R)-5-Benzyloxycarbonyl-2-(phenoxycarbonylamino)pentanoyl]oxyhexadecanamide was obtained according to a similar manner to that of Example 14.

NMR (CDCl$_3$, δ): 7.29–7.52 (7 H, m), 7.22 (1 H, dd, J=7 Hz, 7 Hz), 7.13 (2 H, d, J=8 Hz), 5.76 (1 H, br s), 5.69 (1 H, d, J=7 Hz), 5.30 (1 H, m), 5.12 (2 H, s), 4.38 (1 H, m), 1.54–2.03 (6 H, m), 1.12–1.48 (22 H, m), 0.87 (3 H, t, J=7 Hz)

The following compounds (Examples 56 to 74) were obtained according to a similar manner to that of Example 1.

EXAMPLE 56

Tetradecyl (S)-5-benzyloxycarbonyl-2-(tertiarybutoxycarbonylamino)pentanoate

NMR (CDCl$_3$, δ): 7.34 (5 H, m), 5.10 (2 H, s), 5.03 (1 H, m), 4.27 (1 H, m), 4.11 (2 H, t, J=7 Hz), 2.38 (2 H, m), 1.43 (9 H, s), 1.12–1.93 (28 H, m), 0.87 (3 H, t, J=7 Hz)

EXAMPLE 57

(3S)-3-[6-Benzyloxycarbonyl-2-(tert-butoxycarbonylamino)hexanoyl]oxyhexadecanamide NMR (CDCl$_3$, δ): 7.32 (5 H, m), 6.32 & 5.96 (1 H, br s), 5.58 & 5.50 (1 H, br s), 4.95–5.30 (1 H, m), 5.10 (2 H, s), 4.0–4.3 (1 H, m), 2.3–2.6 (4 H, m), 1.6–1.9 (8 H, m), 1.40 & 1.45 (9 H, s), 1.2–1.4 (22 H, m), 0.88 (3 H, t, J=7 Hz)

EXAMPLE 58

2-[(2S)-5-Benzyloxycarbonyl-2-(tertiarybutoxycarbonylamino)pentanoyl]oxypentadecanamide NMR (CDCl$_3$, δ): 7.36 (5 H, m), 7.01·6.96 (sum 1 H, br s), 5.26 (1 H, s), 5.18 (1 H, m), 5.12 (2 H, s), 5.04 (1 H, m), 4.23·4.11 (sum 1 H, m), 2.43 (2 H, m), 1.64–1.98 (4 H, m), 1.46·1.41 (sum 9 H, s), 1.14–1.38 (24 H, m), 0.87 (3 H, t, J=7 Hz)

EXAMPLE 59

3-[(2S)-5-Benzyloxycarbonyl-2-(tertiarybutoxycarbonylamino)pentanoyl]oxydecanamide NMR (CDCl$_3$, δ): 7.35 (5 H, m), 6.28·5.94 (sum 1 H, br s), 5.40 (1 H, br s), 5.25·5.15 (sum 1 H, m), 5.11 (2 H, s), 5.06 (1 H, m), 4.23·4.13 (sum 1 H, m), 2.30–2.51 (4 H, m), 1.55–1.93 (6 H, m), 1.43·1.42 (sum 9 H, s), 1.15–1.38 (10 H, m), 0.87 (3 H, t, J=7 Hz)

EXAMPLE 60

3-[(2S)-5-Benzyloxycarbonyl-2-(tertiarybutoxycarbonylamino)pentanoyl]oxydodecanamide NMR (CDCl$_3$, δ): 7.36 (5 H, m), 6.28·5.93 (sum 1 H, m), 5.27 (1 H, m), 5.11 (2 H, s), 4.95–5.12 (1 H, m), 4.23·4.13 (sum 1 H, m), 2.32–2.51 (4 H, m), 1.49–1.95 (6 H, m), 1.46·1.45 (sum 9 H, s), 1.08–1.40 (14 H, m), 0.88 (3 H, t, J=7 Hz)

EXAMPLE 61

3-[(2S)-5-Benzyloxycarbonyl-2-(tertiarybutoxycarbonylamino)pentanoyl]oxytetradecanamide NMR (CDCl$_3$, δ): 7.35 (5 H, m), 6.27·5.92 (sum 1 H, br s), 5.27 (1 H, br s), 5.24 (1 H, m), 5.12 (2 H, s), 4.98–5.17 (1 H, m), 4.23·4.12 (sum 1 H, m), 2.32–2.50 (4 H, m), 1.54–1.92 (6 H, m), 1.43·1.41 (sum 9 H, s), 1.13–1.38 (18 H, m), 0.88 (3 H, t, J=7 Hz)

EXAMPLE 62

(3S)-3-[(2S)-5-Benzyloxycarbonyl-2-(tertiarybutoxycarbonylamino)pentanoyl]oxybutyramide NMR (CDCl$_3$, δ): 7.36 (5 H, m), 5.81 (1 H, br s), 5.31 (2 H, m), 5.12 (2 H, s), 5.06 (1 H, d, J=7 Hz), 4.23 (1 H, m), 2.35–2.55 (4 H, m), 1.62–1.89 (4 H, m), 1.44 (9 H, s), 1.34 (3 H, t, J=7 Hz)

EXAMPLE 63

(3R)-3-[(2R)-5-Benzyloxycarbonyl-2-(tertiarybutoxycarbonylamino)pentanoyl]oxyhexadecanamide NMR (DMSO-d$_6$, δ): 7.35 (5 H, m), 7.22 (1 H, d, J=8 Hz), 6.84 (1 H, br s), 5.07 (3 H, m), 3.84 (1 H, br s), 2.31 (4 H, m), 1.41–1.70 (4 H, m), 1.37 (9 H, s), 1.05–1.32 (24 H, m), 0.85 (3 H, t, J=7 Hz)

EXAMPLE 64

(3R)-3-[(2S)-5-Benzyloxycarbonyl-2-(tertiarybutoxycarbonylamino)pentanoyl]oxyhexadecanamide NMR (CDCl$_3$, δ): 7.35 (5 H, m), 6.28 (1 H, br s), 5.32 (1 H, br s), 5.13 (1 H, m), 5.11 (1 H, s), 5.02 (1 H, d, J=7 Hz), 4.12 (1 H, m), 2.35–2.62 (4 H, m), 1.57–1.91 (6 H, m), 1.43 (9 H, s), 1.18–1.37 (22 H, m), 0.88 (3 H, t, J=7 Hz)

EXAMPLE 65

(3S)-3-[(2R)-5-Benzyloxycarbonyl-2-(tertiarybutoxycarbonylamino)pentanoyl]oxyhexadecanamide NMR (CDCl$_3$, δ): 7.35 (5 H, m), 6.28 (1 H, br s), 5.32 (1 H, br s), 5.13 (1 H, m), 5.11 (1 H, s), 5.02 (1 H, d, J=7 Hz), 4.12 (1 H, m), 2.35–2.62 (4 H, m), 1.57–1.91 (6 H, m), 1.43 (9 H, s), 1.18–1.37 (22 H, m), 0.88 (3 H, t, J=7 Hz)

EXAMPLE 66

2-[(2S)-5-Benzyloxycarbonyl-2-(tertiarybutoxycarbonylamino)pentanoyl]oxy-N-methylpentadecanamide NMR (CDCl$_3$, δ): 7.35 (5 H, m), 6.98 (1 H, br s), 5.20. (1 H, m), 5.13·5.11 (sum 2 H, s), 5.06·5.01 (sum 1 H, d, J=7 Hz), 4.21·4.08 (sum 1 H, m), 2.79·2.78 (sum 3 H, d, J=5 Hz), 2.42 (2 H, m), 1.66–1.98 (6 H, m), 1.46·1.43 (sum 9 H, s), 1.15–1.37 (22 H, m), 0.87 (3 H, t, J=7 Hz)

EXAMPLE 67

(3S)-Benzyl 3-[(2S)-5-benzyloxycarbonyl-2-(tertiarybutoxycarbonylamino)pentanoyl]oxyhexadecanoate NMR (CDCl$_3$, δ): 7.35 (10 H, m), 5.27 (1 H, m), 5.11 (2 H, s), 5.09 (2 H, s), 4.99 (1 H, d, J=8 Hz), 4.22 (1 H, m), 2.53–2.69 (2 H, m), 2.33 (2 H, m), 1.48–1.81 (6 H, m), 1.43 (9 H, s), 1.16–1.35 (22 H, m), 0.88 (3 H, t, J=7 Hz)

EXAMPLE 68

Methyl 2-[(2S)-5-benzyloxycarbonyl-2-(tertiarybutoxycarbonylamino)pentanoyl]oxypentadecanoate NMR (CDCl$_3$, δ): 7.36 (5 H, m), 5.12 (2 H, s), 5.03 (2 H, m), 4.38 (1 H, m), 3.75 3.71 (3 H, s), 2.43 (2 H, m), 1.63–2.05 (6 H, m), 1.44 (9 H, s), 1.16–1.48 (22 H, m), 0.89 (3 H, t, J=7 Hz)

EXAMPLE 69

(3S)-Methyl 3-[(2S)-5-benzyloxycarbonyl-2-(tertiarybutoxycarbonylamino)pentanoyl]oxyhexadecanoate NMR (CDCl$_3$, δ): 7.35 (5 H, m), 5.29 (1 H, m), 5.11 (2 H, s), 5.01 (1 H, m), 4.25 (1 H, m), 3.67 (3 H, s), 2.73 (2 H, m), 2.48 (2 H, ddd, J=6 Hz, 6 Hz, 3 Hz), 1.52–1.88 (6 H, m), 1.44 (9 H, s), 1.16–1.48 (22 H, m), 0.88 (3 H, t, J=7 Hz)

EXAMPLE 70

(3S)-(2,2,2-Trichloroethyl) 3-[(2S)-5-benzyloxycarbonyl-2-(tertiarybutoxycarbonylamino)pentanoyl]oxyhexadecanoate NMR (CDCl$_3$, δ): 7.35 (5 H, m), 5.29 (1 H, m), 5.11 (2 H, s), 5.01 (1 H, m), 4.76 (1 H, d, J=12 Hz), 4.70 (1 H, d, J=12 Hz), 4.25 (1 H, m), 2.73 (2 H, m), 2.48 (2 H, ddd, J=6 Hz, 6 Hz, 3 Hz), 1.52–1.88 (6 H, m), 1.44 (9 H, s), 1.16–1.48 (22 H, m), 0.88 (3 H, t, J=7 Hz)

EXAMPLE 71

(2S)-N-Tetradecyl-5-benzyloxycarbonyl-2-(tertiarylbutoxycarbonylamino)pentanamide NMR (CDCl$_3$, δ): 7.35 (5 H, m), 6.08 (1 H, m), 5.11 (2 H, s), 5.02 (1 H, m), 4.00 (1 H, m), 3.22 (2 H, dd, J=14 Hz, 7 Hz), 2.40 (2 H, m), 1.43 (9 H, s), 1.16–1.96 (28 H, m), 0.88 (3 H, t, J=7 Hz)

EXAMPLE 72

(3S)-3-[(2S)-5-Benzyloxycarbonyl-2-(tertiarybutoxycarbonylamino)pentanoyl]aminohexadecanamide NMR (CDCl$_3$, δ): 7.35 (5 H, m), 6.77 (1 H, d, J=8 Hz), 5.95 (1 H, br s), 5.32 (1 H, br s), 5.11 (2 H, s), 5.06 (1 H, d, J=7 Hz), 4.15 (1 H, m), 4.01 (1 H, m), 2.32–2.52 (4 H, m), 1.49–1.92 (6 H, m), 1.43 (9 H, s), 1.06–1.36 (22 H, m), 0.88 (3 H, t, J=7 Hz)

EXAMPLE 73

N-[(S)-5-Benzyloxycarbonyl-2-(tertiarybutoxycarbonylamino)pentanoyl]-N-(2-carbamoylethyl)tridecylamine NMR (CDCl$_3$, δ): 7.36 (5 H, m), 6.64·6.20 (sum 1 H, br s), 5.24 (2 H, m), 5.12 (2 H, s), 4.54 (1 H, m), 3.86·3.62 (sum 2 H, m), 3.50·3.30 (sum 2 H, m), 2.33–2.53 (4 H, m), 1.50–1.77 (4 H, m), 1.43 (9 H, s), 1.14–1.36 (22 H, m), 0.90 (3 H, t, J=7 Hz)

EXAMPLE 74

N-[(S)-5-Benzyloxycarbonyl-2-(tertiarybutoxycarbonylamino)pentanoyl]-N-(N-methylcarbamoylmethyl)tridecylamine NMR (CDCl$_3$, δ): 7.35 (5 H, m), 6.64 (1 H, br s), 5.17·5.09 (1 H, d, J=7 Hz), 5.11 (2 H, s), 4.45 (1 H, m), 4.29·4.07 (sum 1 H, d, J=16 Hz), 3.84·3.75 (sum 1 H, d, J=16 Hz), 3.50 (1 H, m), 3.25·3.11 (sum 1 H, m), 2.84·2.77 (sum 3 H, d, J=5 Hz), 2.40 (2 H, m), 1.50–1.85 (4 H, m), 1.42 (9 H, s), 1.12–1.35 (22 H, m), 0.87 (3 H, t, J=7 Hz)

The following compounds (Examples 75 to 96) were obtained according to a similar manner to that of Example 26.

EXAMPLE 75

(3S)-3-[(2S)-5-Benzyloxycarbonyl-2-(2-biphenylcarbonylamino)pentanoyl]oxyhexadecanamide NMR (DMSO-d$_6$, δ): 8.62 (1 H, d, J=10 Hz), 7.2–7.6 (10 H, m), 6.82 (1 H, br s), 5.10 (2 H, s), 4.18 (2 H, s), 4.18 (1 H, m), 2.2–2.35 (4 H, m), 1.35–1.8 (6 H, m), 1.2–1.35 (22 H, m), 0.84 (3 H, t, J=7 Hz)

FAB-MS: 685 [M+H]

EXAMPLE 76

(3S)-3-[(2S)-5-Benzyloxycarbonyl-2-(N-tert-butoxycarbonyl-L-prolylamino)pentanoyl]oxyhexadecanamide NMR (CDCl$_3$, δ): 7.35 (5 H, m), 6.36 (1 H, br s), 5.44 (1 H, br s), 5.15 (1 H, m), 5.10 (2 H, s), 4.50 (1 H, m), 4.26 (1 H, br s), 3.46 (2 H, br s), 2.35–2.5 (4 H, m), 1.5–1.95 (10 H, m), 1.45 (9 H, s), 1.2–1.35 (22 H, m), 0.88 (3 H, t, J=7 Hz)

EXAMPLE 77

(3S)-3-[(2S)-5-Benzyloxycarbonyl-2-(N-tert-butoxycarbonyl-D-prolylamino)pentanoyl]oxyhexadecanamide NMR (CDCl$_3$, δ): 7.35 (5 H, m), 6.36 (1 H, br s), 5.44 (1 H, br s), 5.15 (1 H, m), 5.10 (2 H, s), 4.50 (1 H, m), 4.26 (1 H, br s), 3.46 (2 H, br s), 2.35–2.5 (4 H, m), 1.5–1.95 (10 H, m), 1.45 (9 H, s), 1.2–1.35 (22 H, m), 0.88 (3 H, t, J=7 Hz)

EXAMPLE 78

(3S)-3-[(2S)-5-Benzyloxycarbonyl-2-(N-tert-butoxycarbonyl-2-piperidylcarbonylamino)pentanoyl]oxyhexadecanamide NMR (CDCl$_3$, δ): 7.34 (5 H, m), 6.75 & 6.65 (1 H, br s), 5.95 & 5.40 (1 H, br s), 5.14 (1 H, m), 5.10 (2 H, s), 4.74 (1 H, br), 4.53 (1 H, m), 2.90 (1 H, br), 2.2–2.5 (5 H, m), 1.46 & 1.44 (9 H, s), 1.35–2.0 (12 H, m), 1.2–1.35 (22 H, m), 0.88 (3 H, t, J=7 Hz)

EXAMPLE 79

(3S)-3-[(2S)-5-Benzyloxycarbonyl-2-(N-tert-butoxycarbonyl-4-piperidylcarbonylamino)pentanoyl]oxyhexadecanamide NMR (DMSO-d$_6$, δ): 8.14 (1 H, d, J=10 Hz), 7.34 (6 H, m), 6.82 (1 H, br s), 5.08 (2 H, s), 5.08 (1 H, m), 4.12 (1 H, m), 3.92 (2 H, d, J=10 Hz), 2.1–2.8 (7 H, m), 1.4–1.7 (10 H, m), 1.35 (9 H, s), 1.1–1.3 (22 H, m), 0.84 (3 H, t, J=7 Hz)

EXAMPLE 80

(3S)-3-[(2S)-5-Benzyloxycarbonyl-2-(6-methyl-2-pyridylcarbonylamino)pentanoyl]oxyhexadecanamide NMR (CDCl$_3$, δ): 8.60 (1 H, d, J=10 Hz), 7.94 (1 H, d, J=10 Hz), 7.72 (1 H, t, J=10 Hz), 7.35 (5 H, m), 7.30 (1 H, d, J=10 Hz), 5.96 (1 H, br s), 5.32 (2 H, m), 5.12 (2 H, s), 4.72 (1 H, m), 2.62 (3 H, s), 2.4–2.55 (4 H, m), 1.1–2.1 (6 H, m), 1.2–1.4 (22 H, m), 0.88 (3 H, t, J=7 Hz)

FAB-MS: 624 [M+H]

EXAMPLE 81

(3S)-3-[(2S)-5-Benzyloxycarbonyl-2-(nicotinoylamino)pentanoyl]oxyhexadecanamide

NMR (CDCl$_3$, δ): 9.11 (1 H, m), 8.76 (1 H, m), 8.17 (1 H, d, J=8 Hz), 7.42 (1 H, dd, J=8 Hz, 5 Hz), 7.22 (1 H, d, J=7 Hz), 5.87 (1 H, br s), 5.45 (1 H, br s), 5.32 (1 H, m), 5.12 (2 H, s), 4.72 (1 H, m), 2.49–2.52 (4 H, m), 1.57–2.09 (6 H, m), 1.16–1.39 (22 H, m), 0.87 (3 H, t, J=7 Hz)

EXAMPLE 82

(3S)-3-[(2S)-5-Benzyloxycarbonyl-2-(isonicotinoylamino)pentanoyl]oxyhexadecanamide NMR (CDCl$_3$, δ): 8.76 (2 H, d, J=6 Hz), 7.67 (2 H, d, J=6 Hz), 7.35 (5 H, m), 7.19 (1 H, J=7 Hz), 5.82 (1 H, br s), 5.40 (1 H, br s), 5.33 (1 H, m), 5.12 (2 H, s), 4.70 (1 H, m), 2.32–2.52 (4 H, m), 1.50–2.08 (6 H, m), 1.08–1.35 (22 H, m), 0.87 (3 H, t, J=7 Hz)

EXAMPLE 83

(3S)-3-[(2S)-5-Benzyloxycarbonyl-2-(2-pyridylcarbonylamino)pentanoyl]oxyhexadecanamide NMR (CDCl$_3$, δ): 8.58 (1 H, d, J=6 Hz), 8.53 (1 H, d, J=9 Hz), 8.15 (1 H, t, J=8 Hz), 7.45 (1 H, dd, J=8 Hz, 6 Hz), 7.34 (5 H, m), 5.93 (1 H, m), 5.28 (1 H, m), 5.11 (2 H, s), 4.72

(1 H, m), 2.38–2.52 (4 H, m), 1.49–2.12 (6 H, m), 1.12–1.39 (22 H, m), 0.87 (3 H, m)

EXAMPLE 84

(3S)-3-[(2S)-5-Benzyloxycarbonyl-2-(2-pyrazinylcarbonylamino)pentanoyl]oxyhexadecanamide NMR (CDCl$_3$, δ): 9.37 (1 H, s), 8.77 (1 H, d, J=4 Hz), 8.55 (1 H, d, J=4 Hz), 8.33 (1 H, d, J=10 Hz), 7.36 (5 H, m), 5.80 (1 H, br s), 5.36 (1 H, br s), 5.33 (1 H, m), 5.10 (2 H, s), 4.76 (1 H, m), 2.38–2.52 (4 H, m), 1.6–2.1 (6 H, m), 1.2–1.4 (22 H, m), 0.88 (3 H, t, J=7 Hz)

FAB-MS: 611 [M+H]

EXAMPLE 85

(3S)-3-[(2S)-5-Benzyloxycarbonyl-2-{(5-quinolyl)carbonylamino}pentanoyl]oxyhexadecanamide NMR (DMSO-d$_6$, δ): 9.02 (1 H, d, J=110 Hz), 8.94 (1 H, m), 8.64 (1 H, d, J=10 Hz), 8.12 (1 H, d, J=10 Hz), 7.75 (2 H, ABq), 7.56 (1 H, m), 7.38 (1 H, br s), 7.35 (5 H, m), 6.86 (1 H, br s), 5.18 (1 H, m), 5.08 (2 H, s), 4.44 (1 H, m), 2.3–2.5 (4 H, m), 1.5–1.9 (6 H, m), 1.1–1.4 (22 H, m), 0.82 (3 H, t, J=7 Hz)

EXAMPLE 86

(3R)-3-[(2R)-5-Benzyloxycarbonyl-2-{(3-quinolyl)carbonylamino}pentanoyl]oxyhexadecanamide NMR (CDCl$_3$, δ): 9.35 (1 H, d, J=1.5 Hz), 8.64 (1 H, d, J=1.5 Hz), 8.16 (1 H, d, J=8 Hz), 7.92 (1 H, d, J=8 Hz), 7.83 (1 H, t, J=8 Hz), 7.63 (1 H, t, J=8 Hz), 7.35 (5 H, m), 5.95 (1 H, br s), 5.50 (1 H, br s), 5.35 (1 H, m), 5.12 (2 H, s), 4.78 (1 H, m), 2.47 (4 H, m), 1.57–2.12 (6 H, m), 1.15–1.38 (22 H, m), 0.87 (3 H, t, J=7 Hz)

EXAMPLE 87

(3S)-3-[(2S)-5-Benzyloxycarbonyl-2-{(1-isoquinolyl)carbonylamino}pentanoyl]oxyhexadecanamide NMR (DMSO-d$_6$, δ): 9.10 (1 H, d, J=10 Hz), 8.85 (1 H, d, J=10 Hz), 8.54 (1 H, d, J=7 Hz), 8.04 (2 H, m), 7.82 (1 H, t, J=7 Hz), 7.70 (1 H, t, J=7 Hz), 7.38 (1 H, br 3), 7.32 (5 H, m), 6.86 (1 H, br 3), 5.18 (1 H, m), 5.08 (2 H, s), 4.45 (1 H, m), 2.2–2.45 (4 H, m), 1.45–1.95 (6 H, m), 1.1–1.3 (22 H, m), 0.84 (3 H, t, J=7 Hz)

FAB-MS: 660 [M+H]

EXAMPLE 88

(3S)-3-[(2S)-5-Benzyloxycarbonyl-2-{(3-isoquinolyl)carbonylamino}pentanoyl]oxyhexadecanamide NMR (CDCl$_3$, δ): 9.20 (1 H, s), 8.74 (1 H, d, J=10 Hz), 8.05 (1 H, d, J=10 Hz), 7.98 (1 H, d, J=10 Hz), 7.76 (2 H, m), 7.34 (5 H, m), 6.08 (1 H, br s), 5.53 (1 H, br s), 5.30 (1 H, m), 5.12 (2 H, s), 4.82 (1 H, m), 2.3–2.6 (4 H, m), 1.1–2.0 (6 H, m), 1.1–1.4 (22 H, m), 0.88 (3 H, t, J=7 Hz)

EXAMPLE 89

(3S)-3-[(2S)-5-Benzyloxycarbonyl-2-{(2-quinoxalinyl)carbonylamino}pentanoyl]oxyhexadecanamide NMR (DMSO-d$_6$, δ): 9.45 (1 H, s), 9.18 (1 H, d, J=10 Hz), 8.22 (2 H, m), 8.00 (2 H, m), 7.35 (1 H, br s), 7.25–7.35 (5 H, m), 6.85 (1 H, br s), 5.15 (1 H, m), 5.08 (2 H, s), 4.50 (1 H, m), 2.25–2.45 (2 H, m), 1.90 (2 H, m), 1.65 (2 H, m), 1.50 (2 H, m), 1.0–1.3 (22 H, m), 0.84 (3 H, t, J=7 Hz)

EXAMPLE 90

(3S)-3-[(2S)-5-Benzyloxycarbonyl-2-{((6S)-5-tert-butoxycarbonyl-3-tert-butoxycarbonyl-4,5,6,7-tetrahydro-3H-imidazo[4,5-c]pyridin-6-yl)carbonylamino}pentanoyl]oxyhexadecanamide NMR (CDCl$_3$, δ): 8.00 (1 H, s), 7.34 (5 H, m), 6.70 (1 H, br s), 5.85 (1 H, br s), 5.30 (1 H, br s), 5.20 (1 H, m), 5.10 (2 H, s), 4.42 (2 H, br s), 3.3 (1 H, m), 2.90 (1 H, m), 2.2–2.5 (4 H, m), 1.60 (9 H, s), 1.50 (9 H, s), 1.4–1.9 (8 H, m), 1.15–1.35 (22 H, m), 0.88 (3 H, t, J=7 Hz)

EXAMPLE 91

(3S)-3-[(2S)-5-Benzyloxycarbonyl-2-{((6R)-5-tert-butoxycarbonyl-3-tert-butoxycarbonyl-4,5,6,7-tetrahydro-3H-imidazo[4,5-c]pyridin-6-yl)carbonylamino}pentanoyl]oxyhexadecanamide NMR (CDCl$_3$, δ): 8.00 (1 H, s), 7.34 (5 H, m), 6.70 (1 H, br s), 5.85 (1 H, br s), 5.30 (1 H, br s), 5.20 (1 H, m), 5.10 (2 H, s), 4.42 (2 H, br s), 3.3 (1 H, m), 2.90 (2 H, m), 2.2–2.5 (4 H, m), 1.60 (9 H, s), 1.50 (9 H, s), 1.4–1.9 (8 H, m), 1.15–1.35 (22 H, m), 0.88 (3 H, t, J=7 Hz)

EXAMPLE 92

N-[(S)-5-Benzyloxycarbonyl-2-{(2-quinolyl)carbonylamino}pentanoyl]-N-(2-carbamoylethyl)tridecylamine NMR (CDCl$_3$, δ): 8.89·8.84 (sum 1 H, d, J=8 Hz), 8.31 (1 H, d, J=8 Hz), 8.26 (1 H, d, J=8 Hz), 8.17 (1 H, d, J=8 Hz), 7.88 (1 H, d, J=8 Hz), 7.78 (1 H, m), 7.63 (1 H, m), 7.34 (5 H, m), 6.78 (1 H, br s), 6.17 (1 H, br s), 5.11 (1 H, m), 5.10 (2 H, s), 3.85·3.68 (sum 2 H, m), 3.52·3.41 (sum 2 H, m), 2.37–2.63 (4 H, m), 1.62–2.00 (4 H, m), 1.16–1.38 (22 H, m), 0.88 (3 H, t, J=7 Hz)

EXAMPLE 93

N-[(S)-5-Benzyloxycarbonyl-2-{(2-quinolyl)carbonylamino}pentanoyl]-N-(N-methylcarbamoylmethyl)tridecylamine NMR (CDCl$_3$, δ): 8.83 (1 H, d, J=7 Hz), 8.33 (1 H, d, J=8 Hz), 8.35·8.34 (sum 1 H, d, J=8 Hz), 8.18 (1 H, m), 7.90 (1 H, d, J=8 Hz), 7.80 (1 H, m), 7.65 (1 H, m), 7.35 (5 H, m), 6.72 (1 H, br s), 5.14 (2 H, s), 5.05 (1 H, m), 4.18 (1 H, d, J=16 Hz), 3.95 (1 H, d, J=16 Hz), 3.60 (1 H, m), 3.43 (1 H, m), 2.88·2.79 (sum 3 H, d, J=5 Hz), 2.48 (2 H, m), 1.62–2.07 (4 H, m), 1.07–1.38 (22 H, m), 0.88 (3 H, t, J=7 Hz)

EXAMPLE 94

(3S)-3-[(2S)-5-Benzyloxycarbonyl-2-(5-imidazolylmethylcarbonylamino)pentanoyl]oxyhexadecanamide NMR (CDCl$_3$, δ): 7.60 (1 H, s), 7.35 (5 H, m), 6.90 (1 H, s), 6.30 (1 H, br s), 5.65 (1 H, br s), 5.20 (1 H, m), 5.10 (2 H, s), 4.50 (1 H, m), 3.57 (2 H, ABq), 2.3–2.5 (4 H, m), 1.5–1.9 (6 H, m), 1.1–1.4 (22 H, m), 0.88 (3 H, t, J=7 Hz)

EXAMPLE 95

(3S)-3-[(2S)-5-Benzyloxycarbonyl-2-(2-pyridylmethylcarbonylamino)pentanoyl]oxyhexadecanamide NMR (CDCl$_3$, δ): 8.56 (1 H, d, J=5 Hz), 8.00 (1 H, d, J=10 Hz), 7.66 (1 H, dd, J=10 Hz, 5 Hz), 7.35 (5 H, m), 7.25 (1 H, d, J=10 Hz), 7.20 (1 H, dd, J=10 Hz, 5 Hz), 6.00 (1 H, br s), 5.36 (1 H, br s), 5.20 (1 H, m), 5.10 (2 H, s), 4.50 (1

H, m), 3.75 (2 H, s), 2.3–2.45 (4 H, m), 1.5–2.0 (6 H, m), 1.1–1.35 (22 H, m), 0.88 (3 H, t, J=7 Hz)

FAB-MS: 624 [M+H]

EXAMPLE 96

(3S)-3-[(2S)-5-Benzyloxycarbonyl-2-(8-quinolylsulfonylamino)pentanoyl]oxyhexadecanamide NMR (DMSO-$d_6$, δ): 9.04 (1 H, d, J=5 Hz), 8.50 (1 H, d, J=10 Hz), 8.26 (2 H, m), 7.65 (2 H, q, J=10 Hz), 7.35 (5 H, m), 7.22 (1 H, br s), 6.72 (1 H, br s), 5.12 (2 H, s), 4.72 (1 H, m), 4.15 (1 H, m), 2.0–2.2 (4 H, m), 1.4–1.8 (6 H, m), 0.9–1.3 (22 H, m), 1.88 (3 H, t, J=7 Hz)

The following compounds (Examples 97 to 100) were obtained according to a similar manner to that of Preparation 4.

EXAMPLE 97

(3S)-3-[(2S)-5-Carboxy-2-{(2-piperidyl)carbonylamino}-pentanoyl]oxyhexadecanamide hydrochloride [from (3S)-3-[(2S)-5-carboxy-2-{(N-t-butoxycarbonyl-2-piperidyl)carbonylamino}-pentanoyl]oxyhexadecanamide]

NMR (CD$_3$OD, δ): 5.28 (1 H, m), 4.40 (1 H, m), 3.85 (1 H, d, J=12 Hz), 3.42 (1 H, d, J=12 Hz), 3.06 (1 H, t, J=12 Hz), 2.2–2.6 (5 H, m), 1.6–2.0 (12 H, m), 1.2–1.4 (22 H, m), 0.90 (3 H, t, J=7 Hz)

EXAMPLE 98

(3S)-3-[(2S)-5-Carboxy-2-{(4-piperidyl)carbonylamino}-pentanoyl]oxyhexadecanamide hydrochloride [from (3S)-3-[(2S)-5-carboxy-2-{(N-t-butoxycarbonyl-4-piperidyl)carbonylamino}pentanoyl]oxyhexadecanamide]

NMR (DMSO-$d_6$, δ): 8.14 (1 H, d, J=10 Hz), 7.34 (1 H, br s), 6.82 (1 H, br s), 5.08 (1 H, m), 4.12 (1 H, m), 3.92 (2 H, d, J=10 Hz), 2.1–2.8 (7 H, m), 1.4–1.7 (10 H, m), 1.35 (9 H, s), 1.1–1.3 (22 H, m), 0.84 (3 H, t, J=7 Hz)

FAB-MS: 648 [M+Na]

EXAMPLE 99

(3S)-3-[(2S)-5-Carboxy-2-{((6R)-4,5,6,7-tetrahydro-3H-imidazo[4,5-c]pyridin-6-yl)carbonylamino}pentanoyl]-oxyhexadecanamide dihydrochloride [from (3S)-3-[(2S)-5-carboxy-2-{((6R)-3-t-butoxycarbonyl-5-t-butoxycarbonyl-4,5,6,7-tetrahydro-3H-imidazo[4,5-c]pyridin-6-yl)carbonylamino}pentanoyl]oxyhexadecanamide]

NMR (CD$_3$OD, δ): 8.98 (1 H, s), 5.30 (1 H, m), 4.4–4.6 (3 H, m), 3.08 (1 H, dd, J=15 Hz, 5 Hz), 3.17 (1 H, dd, J=15 Hz, 10 Hz), 2.52 (2 H, m), 2.36 (2 H, t, J=7 Hz), 1.4–2.0 (6 H, m), 1.2–1.4 (22 H, m), 0.90 (3 H, t, J=7 Hz)

EXAMPLE 100

(3S)-3-[(2S)-5-Carboxy-2-{((6S)-4,5,6,7-tetrahydro-3H-imidazo[4,5-c]pyridin-6-yl)carbonylamino}pentanoyl]-oxyhexadecanamide dihydrochloride [from (3S)-3-[(2S)-5-carboxy-2-{((6S)-3-t-butoxycarbonyl-5-t-butoxycarbonyl-4,5,6,7-tetrahydro-3H-imidazo[4,5-c]pyridin-6-yl)carbonylamino}pentanoyl]oxyhexadecanamide]

NMR (CD$_3$OD, δ): 8.98 (1 H, s), 5.30 (1 H, m), 4.4–4.6 (3 H, m), 3.08 (1 H, dd, J=15 Hz, 5 Hz), 3.17 (1 H, dd, J=15 Hz, 10 Hz), 2.52 (2 H, m), 2.36 (2 H, t, J=7 Hz), 1.4–2.0 (6 H, m), 1.2–1.4 (22 H, m), 0.90 (3 H, t, J=7 Hz)

The following compounds (Examples 101 to 148) were obtained according to a similar manner to that of Example 6.

EXAMPLE 101

(S)-Tetradecyl 5-carboxy-2-(tertiarybutoxycarbonylamino)pentanoate

NMR (CDCl$_3$, δ): 5.11 (1 H, m), 4.30 (1 H, m), 4.13 (2 H, t, J=7 Hz), 2.40 (2 H, m), 1.43 (9 H, s), 1.14–1.92 (28 H, m), 0.88 (3 H, t, J=7 Hz)

EXAMPLE 102

(3S)-3-[6-Carboxy-2-(tert-butoxycarbonylamino)hexanoyl]-oxyhexadecanamide

NMR (CDCl$_3$, δ): 6.32 & 5.96 (1 H, br s), 5.58 & 5.50 (1 H, br s), 4.95–5.30 (1 H, m), 4.0–4.3 (1 H, m), 2.3–2.6 (4 H, m), 1.6–1.9 (8 H, m), 1.40 & 1.45 (9 H, s), 1.2–1.4 (22 H, m), 0.88 (3 H, t, J=7 Hz)

EXAMPLE 103

2-[(2S)-5-Carboxy-2-(tertiarybutoxycarbonylamino)pentanoyl]oxypentadecanamide

NMR (CDCl$_3$, δ): 7.04·6.30 (1 H, br s), 5.33·5.21 (1 H, m), 5.25·5.05 (1 H, d, J=8 Hz), 4.44·4.19 (1 H, m), 2.43 (2 H, m), 1.64·1.98 (4 H, m), 1.46·1.43 (9 H, s), 1.12–1.37 (24 H, m), 0.88 (3H t, J=7 Hz)

EXAMPLE 104

3-[(2S)-5-Carboxy-2-(tertiarybutoxycarbonylamino)-pentanoyl]oxydecanamide

NMR (DMSO-$d_6$, δ): 7.36 (1 H, br s), 7.22 (1 H, d, J=7 Hz), 6.85 (1 H, br s), 5.08 (1 H, m), 3.83 (1 H, m), 2.07–2.45 (4 H, m), 1.38 (9 H, s), 1.14–1.86 (28 H, m), 0.85 (3 H, t, J=7 Hz)

EXAMPLE 105

3-[(2S)-5-Carboxy-2-(tertiarybutoxycarbonylamino)pentanoyl]oxydodecanamide

NMR (CDCl$_3$, δ): 7.05·6.41·6.22 (total 2 H, br s), 5.10–5.37 (2 H, m), 4.27·4.18 (sum 1 H, m), 2.26–2.62 (4 H, m), 1.50–1.94 (6 H, m), 1.44 (9 H, s), 1.08–1.39 (14 H, m), 0.88 (3 H, t, J=7 Hz)

EXAMPLE 106

3-[(2S)-5-Carboxy-2-(tertiarybutoxycarbonylamino)-pentanoyl]oxytetradecanamide

NMR (CDCl$_3$, δ): 7.07·6.44·6.23 (total 2 H, br s), 5.10–5.39 (2 H, m), 4.28·4.18 (sum 1 H, m), 2.25–2.60 (4 H, m), 1.50–1.92 (6 H, m), 1.44 (9 H, s), 1.10–1.39 (18 H, m), 0.88 (3 H, t, J=7 Hz)

EXAMPLE 107

(3S)-3-[(2S)-5-Carboxy-2-(tertiarybutoxycarbonylamino)pentanoyl]oxybutyramide

NMR (CDCl$_3$—CD$_3$OD(20:1), δ): 5.27 (1 H, m), 4.18 (1 H, m), 2.18–2.55 (4 H, m), 1.49–1.85 (4 H, m), 1.41 (9 H, s), 1.31 (3 H, d, J=7 Hz)

EXAMPLE 108

(3R)-3-[(2R)-5-Carboxy-2-(tertiarybutoxycarbonylamino)pentanoyl]oxyhexadecanamide NMR (DMSO-$d_6$, δ): 7.35 (1 H, br s), 7.21 (1 H, d, J=7.5 Hz), 6.84 (1 H, br s), 5.09 (1 H, m), 3.82 (1 H, m), 2.30 (2 H, dd, J=5 Hz, 4 Hz), 2.16 (2 H, m), 1.10–1.70 (37 H, m), 0.85 (3 H, t, J=7 Hz)

EXAMPLE 109

(3R)-3-[(2S)-5-Carboxy-2-(tertiarybutoxycarbonylamino)pentanoyl]oxyhexadecanamide NMR (CDCl$_3$, δ): 6.45 (1 H, br s), 6.30 (1 H, br s), 5.19 (2 H, m), 4.18 (1 H, m), 2.29–2.64 (4 H, m), 1.16–1.92 (6 H, m), 1.45 (9 H, s), 1.18–1.38 (22 H, m), 0.89 (3 H, t, J=7 Hz)

EXAMPLE 110

(3S)-3-[(2R)-5-Carboxy-2-(tertiarybutoxycarbonylamino)pentanoyl]oxyhexadecanamide NMR (CDCl$_3$, δ): 6.45 (1 H, br s), 6.30 (1 H, br s), 5.19 (2 H, m), 4.18 (1 H, m), 2.29–2.64 (4 H, m), 1.16–1.92 (6 H, m), 1.45 (9 H, s), 1.18–1.38 (22 H, m), 0.89 (3 H, t, J=7 Hz)

EXAMPLE 111

2-[(2S)-5-Carboxy-2-(tertiarybutoxycarbonylamino)pentanoyl]oxy-N-methylpentadecanamide NMR (CDCl$_3$, δ): 5.20 (1 H, m), 5.07 (1 H, m), 4.22·4.12 (sum 1 H, m), 2.79 (3 H, d, J=5 Hz), 2.42 (2 H, m), 1.70–2.00 (4 H, m), 1.46·1.44 (9 H, s), 1.16–1.35 (24 H, m), 0.87 (3 H, t, J=7 Hz)

EXAMPLE 112

(3S)-3-[(2S)-5-Carboxy-2-(tertiarybutoxycarbonylamino)-pentanoyl]oxyhexadecanoic acid NMR (CDCl$_3$, δ): 5.20–5.40 (2 H, m), 4.30 (1 H, m), 2.63 (2 H, m), 2.35 (2 H, m), 1.53–1.92 (6 H, m), 1.45 (9 H, s), 1.16–1.36 (22 H, m), 0.88 (3 H, t, J=7 Hz)

EXAMPLE 113

Methyl 2-[(2S)-5-Carboxy-2-(tertiarybutoxycarbonylamino)pentanoyl]oxypentadecanoate NMR (CDCl$_3$, δ): 5.05 (2 H, m), 4.39 (1 H, m), 3.74 (3 H, s), 2.42 (2 H, m), 1.65–2.03 (6 H, m), 1.44 (9 H, s), 1.13–1.40 (22 H, m), 0.88 (3 H, t, J=7 Hz)

EXAMPLE 114

(3S)-Methyl 3-[(2S)-5-carboxy-2-(tertiarybutoxycarbonylamino)pentanoyl]oxyhexadecanoate NMR (CDCl$_3$, δ): 5.26 (1 H, m), 5.10 (1 H, d, J=7 Hz), 4.27 (1 H, m), 3.67 (3 H, s), 2.59 (2 H, m), 2.39 (2 H, m), 1.53–1.90 (6 H, m), 1.45 (9 H, s), 1.15–1.37 (22 H, m), 0.88 (3 H, t, J=7 Hz)

EXAMPLE 115

N-[(2S)-5-Carboxy-2-(tertiarybutoxycarbonylamino)pentanoyl]tetradecylamine

NMR (CDCl$_3$, δ): 6.50 (1 H, br s), 5.41 (1 H, m), 4.06 (1 H, m), 3.22 (2 H, m), 2.37 (2 H, m), 1.43 (9 H, s), 1.03–1.96 (28 H, m), 0.88 (3 H, t, J=7 Hz)

EXAMPLE 116

(3S)-3-[(2S)-5-Carboxy-2-(tertiarybutoxycarbonylamino)pentanoyl]aminohexadecanamide NMR (DMSO-d$_6$, δ): 7.63 (1 H, d, J=8 Hz), 7.25 (1 H, br s), 6.82 (1 H, d, J=8 Hz), 6.77 (1 H, br s), 3.98 (1 H, m), 3.78 (1 H, m), 2.15 (4 H, m), 1.36 (9 H, s), 1.07–1.65 (28 H, m), 0.85 (3 H, t, J=7 Hz)

EXAMPLE 117

N-[(2S)-5-Carboxy-2-(tertiarybutoxycarbonylamino)pentanoyl]-N-(2-carbamoylethyl)tridecylamine NMR (CDCl$_3$, δ): 6.84·6.64 (1 H, br s), 6.58·6.27 (1 H, br s), 5.54·5.51 (1 H, d, J=7 Hz), 4.60 (1 H, m), 3.96 (1 H, m), 3.12–3.73 (3 H, m), 2.23–2.60 (4 H, m), 1.50–1.80 (4 H, m), 1.12–1.33 (22 H, m), 0.88 (3 H, t, J=7 Hz)

EXAMPLE 118

(3S)-3-[(2S)-5-Carboxy-2-(2-biphenylcarbonylamino)-pentanoyl]oxyhexadecanamide hydrochloride NMR (DMSO-d$_6$, δ): 8.65 (1 H, d, J=10 Hz), 7.25–7.55 (10 H, m), 6.85 (1 H, br s), 5.12 (1 H, m), 4.18 (1 H, m), 2.1–2.4 (4 H, m), 1.3–1.9 (6 H, m), 1.15–1.3 (22 H, m), 0.84 (3 H, t, J=7 Hz)

EXAMPLE 119

(3R)-3-[(2R)-5-Carboxy-2-(p-methoxybenzoylamino)pentanoyl]oxyhexadecanamide

NMR (CD$_3$OD, δ): 7.85 (2 H, d, J=8 Hz), 6.98 (2 H, d, J=8 Hz), 5.27 (1 H, m), 4.52 (1 H, m), 3.84 (3 H, s), 2.39–2.60 (2 H, m), 2.34 (2 H, t, J=7 Hz), 1.57–2.04 (6 H, m), 1.18–1.44 (22 H, m), 0.89 (3 H, t, J=7 Hz)

EXAMPLE 120

(3S)-N-Methyl-3-[(2S)-5-carboxy-2-(p-methoxybenzoylamino)pentanoyl]oxyhexadecanamide NMR (CDCl$_3$, δ): 7.79 (2 H, d, J=8 Hz), 7.08 (1 H, d, J=7 Hz), 6.91 (2 H, d, J=8 Hz), 6.28 (1 H, m), 5.30 (1 H, m), 4.71 (1 H, m), 3.84 (3 H, m), 2.74 (2 H, m), 2.32–2.52 (2 H, m), 1.52–2.07 (6 H, m), 1.13–1.36 (22 H, m), 0.89 (3 H, t, J=7 Hz)

EXAMPLE 121

(3S)-3-[(2S)-5-Carboxy-2-(N-tert-butoxycarbonyl-L-prolylamino)pentanoyl]oxyhexadecanamide NMR (CDCl$_3$, δ): 6.36 (1 H, br s), 5.44 (1 H, br s), 5.15 (1 H, m), 4.50 (1 H, m), 4.26 (1 H, br s), 3.46 (2 H, br s), 2.35–2.5 (4 H, m), 1.5–1.95 (10 H, m), 1.45 (9 H, s), 1.2–1.35 (22 H, m), 0.88 (3 H, t, J=7 Hz)

EXAMPLE 122

(3S)-3-[(2S)-5-Carboxy-2-(N-tert-butoxycarbonyl-D-prolylamino)pentanoyl]oxyhexadecanamide NMR (CDCl$_3$, δ): 6.36 (1 H, br s), 5.44 (1 H, br s), 5.15 (1 H, m), 4.50 (1 H, m), 4.26 (1 H, br s), 3.46 (2 H, br s), 2.35–2.5 (4 H, m), 1.5–1.95 (10 H, m), 1.45 (9 H, s), 1.2–1.35 (22 H, m), 0.88 (3 H, t, J=7 Hz)

EXAMPLE 123

(3S)-3-[(2S)-5-Carboxy-2-{(1-tert-butoxycarbonyl-2-piperidyl)carbonylamino}pentanoyl]oxyhexadecanamide NMR (CDCl$_3$, δ): 7.10 (1 H, br s), 6.80 (1 H, d, J=10 Hz), 5.28 (1 H, m), 4.76 (1 H, br), 4.55 (1 H, m), 2.90 (1 H, br), 2.2–2.6 (5 H, m), 1.50 (9 H, s), 1.35–2.0 (12 H, m), 1.2–1.35 (22 H, m), 0.88 (3 H, t, J=7 Hz)

EXAMPLE 124

(3S)-3-[(2S)-5-Carboxy-2-{(1-tert-butoxycarbonyl-4-piperidyl)carbonylamino}pentanoyl]oxyhexadecanamide NMR (DMSO-$d_6$, δ): 8.14 (1 H, d, J=10 Hz), 7.34 (1 H, br s), 6.82 (1 H, br s), 5.08 (1 H, m), 4.12 (1 H, m), 3.92 (2 H, d, J=10 Hz), 2.1–2.8 (7 H, m), 1.4–1.7 (10 H, m), 1.35 (9 H, s), 1.1–1.3 (22 H, m), 0.84 (3 H, t, J=7 Hz)

FAB-MS: 648 [M+Na]

EXAMPLE 125

(3S)-3-[(2S)-5-Carboxy-2-(piperidinocarbonylamino)-pentanoyl]oxyhexadecanamide

NMR (DMSO-$d_6$, δ): 7.34 (1 H, br s), 6.83 (1 H, br s), 6.57 (1 H, d, J=7 Hz), 5.05 (1 H, m), 3.96 (1 H, m), 3.27 (4 H, m), 2.33 (1 H, dd, J=15 Hz, 7 Hz), 2.26 (1 H, dd, J=15 Hz, 7 Hz), 2.16 (2 H, t, J=7 Hz), 1.13–1.73 (34 H, m), 0.86 (3 H, t, J=7 Hz)

EXAMPLE 126

(3S)-3-[(2S)-5-Carboxy-2-{{4-(3,4-methylenedioxybenzyl)-1-piperazinyl}carbonylamino}pentanoyl]oxyhexadecanamide NMR (DMSO-$d_6$, δ): 7.35 (1 H, s), 6.85 (3 H, m), 6.74 (2 H, d, J=8 Hz), 5.98 (2 H, s), 5.05 (1 H, m), 3.94 (1 H, m), 3.37 (6 H, m), 2.05–2.42 (8 H, m), 1.40–1.75 (6 H, m), 1.06–1.36 (22 H, m), 0.84 (3 H, t, J=7 Hz)

EXAMPLE 127

(3S)-3-[(2S)-5-Carboxy-2-(morpholinocarbonylamino) pentanoyl]oxyhexadecanamide

NMR (DMSO-$d_6$, δ): 7.33 (1 H, br s), 6.83 (1 H, br s), 6.73 (1 H, d, J=7 Hz), 5.05 (1 H, m), 3.97 (1 H, m), 3.52 (4 H, m), 3.27 (4 H, m), 2.32 (1 H, dd, J=15 Hz, 8 Hz), 2.26 (1 H, dd, J=15 Hz, 7 Hz), 2.16 (2 H, t, J=7 Hz), 1.40–1.75 (6 H, m), 1.12–1.35 (22 H, m), 0.84 (3 H, t, J=7 Hz)

EXAMPLE 128

(3S)-3-[(2S)-5-Carboxy-2-(nicotinoylamino)pentanoyl] oxyhexadecanamide

NMR (DMSO-$d_6$, δ): 9.02 (1 H, m), 8.96 (1 H, m), 8.73 (1 H, m), 8.22 (1 H, m), 7.52 (1 H, dd, J=8 Hz, 5 Hz), 7.36 (1 H, br s), 6.85 (1 H, br s), 5.12 (1 H, m), 4.36 (1 H, m), 2.34 (2 H, t, J=7 Hz), 2.23 (2 H, t, J=7 Hz), 1.43–1.92 (6 H, m), 1.09–1.36 (22 H, m), 0.85 (3 H, t, J=7 Hz)

EXAMPLE 129

(3S)-3-[(2S)-5-Carboxy-2-isonicotinoylamino) pentanoyl]oxyhexadecanamide

NMR (DMSO-$d_6$, δ): 8.72 (2 H, d, J=6 Hz), 7.87 (2 H, d, J=6 Hz), 7.37 (1 H, br s), 6.86 (1 H, br s), 5.11 (1 H, m), 4.25 (1 H, m), 2.32 (2 H, t, J=7 Hz), 2.11 (2 H, t, J=7 Hz), 1.78 (2 H, m), 1.43–1.65 (4 H, m), 1.10–1.38 (22 H, m), 0.85 (3 H, t, J=7 Hz)

EXAMPLE 130

(3S)-3-[(2S)-5-Carboxy-2-{(2-pyridyl)carbonylamino}-pentanoyl]oxyhexadecanamide

NMR (CDCl$_3$, δ): 8.60 (2 H, m), 8.15 (1 H, d, J=9 Hz), 7.84 (1 H, t, J=8 Hz), 7.43 (1 H, dd, J=8 Hz, 6 Hz), 5.46 (1 H, m), 4.77 (1 H, m), 2.19–2.75 (4 H, m), 1.50–2.12 (6 H, m), 1.08–1.36 (22 H, m), 0.87 (3 H, m)

EXAMPLE 131

(3S)-3-[(2S)-5-Carboxy-2-{(2-pyrazinyl)carbonylamino}pentanoyl]oxyhexadecanamide NMR (DMSO-$d_6$, δ): 9.20 (1 H, s), 9.04 (1 H, br s), 8.90 (1 H, s), 8.76 (1 H, s), 7.42 (1 H, br s), 6.88 (1 H, br s), 5.12 (1 H, m), 4.40 (1 H, m), 1.9–2.4 (4 H, m), 1.4–1.9 (6 H, m), 1.2–1.4 (22 H, m), 0.88 (3 H, t, J=7 Hz)

FAB-MS: 543 [M+Na]

EXAMPLE 132

(3S)-3-[(2S)-5-Carboxy-2-{(5-quinolyl)carbonylamino}-pentanoyl]oxyhexadecanamide NMR (DMSO-$d_6$, δ): 9.02 (1 H, d, J=10 Hz), 8.94 (1 H, m), 8.64 (1 H, d, J=10 Hz), 8.12 (1 H, d, J=10 Hz), 7.75 (2 H, ABq), 7.56 (1 H, m), 7.38 (1 H, br s), 6.86 (1 H, br s), 5.18 (1 H, m), 4.44 (1 H, m), 2.3–2.5 (4 H, m), 1.5–1.9 (6 H, m), 1.1–1.4 (22 H, m), 0.82 (3 H, t, J=7 Hz)

EXAMPLE 133

(3S)-3-[(2S)-5-Carboxy-2-{(1-isoquinolyl)carbonylamino}-pentanoyl]oxyhexadecanamide NMR (DMSO-$d_6$, δ): 9.10 (1 H, d, J=10 Hz), 8.85 (1 H, d, J=10 Hz), 8.54 (1 H, d, J=7 Hz), 8.04 (2 H, m), 7.82 (1 H, t, J=7 Hz), 7.70 (1 H, t, J=7 Hz), 7.38 (1 H, br s), 6.86 (1 H, br s), 5.18 (1 H, m), 4.45 (1 H, m), 2.2–2.45 (4 H, m), 1.45–1.95 (6 H, m), 1.1–1.3 (22 H, m), 0.84 (3 H, t, J=7 Hz)

FAB-MS: 592 [M+Na]

EXAMPLE 134

(3S)-3-[(2S)-5-Carboxy-2-{(3-isoquinolyl)carbonylamino}-pentanoyl]oxyhexadecanamide NMR (DMSO-$d_6$, δ): 9.42 (1 H, s), 8.97 (1 H, d, J=10 Hz), 8.56 (1 H, s), 8.1–8.4 (2 H, m), 7.7–7.9 (2 H, m), 5.15 (1 H, m), 4.50 (1 H, m), 2.2–2.4 (4 H, m), 1.4–2.0 (6 H, m), 1.1–1.4 (22 H, m), 0.83 (3 H, t, J=7 Hz)

FAB-MS: 570 [M+H]

EXAMPLE 135

(3S)-3-[(2S)-5-Carboxy-2-{(2-quinoxalinyl)carbonylamino}pentanoyl]oxyhexadecanamide NMR (DMSO-$d_6$, δ): 9.45 (1 H, s), 9.18 (1 H, d, J=10 Hz), 8.22 (2 H, m), 8.00 (2 H, m), 7.35 (1 H, br s), 6.85 (1 H, br s), 5.15 (1 H, m), 4.50 (1 H, m), 2.25–2.45 (2 H, m), 1.90 (2 H, m), 1.65 (2 H, m), 1.50 (2 H, m), 1.0–1.3 (22 H, m), 0.84 (3 H, t, J=7 Hz)

EXAMPLE 136

(3S)-3-[(2S)-5-Carboxy-2-{((6S)-5-tert-butoxycarbonyl-3-tert-butoxycarbonyl-4,5,6,7-tetrahydro-3H-imidazo[4,5-c]-pyridin-6-yl)carbonylamino}pentanoyl] oxyhexadecanamide NMR (CDCl$_3$, δ): 8.00 (1 H, s), 6.70 (1 H, br s), 5.85 (1 H, br s), 5.30 (1 H, br s), 5.20 (1 H, m), 4.42 (2 H, br s), 3.3 (1 H, m), 2.90 (2 H, m), 2.2–2.5 (4 H, m), 1.60 (9 H, s), 1.50 (9 H, s), 1.4–1.9 (8 H, m), 1.15–1.35 (22 H, m), 0.88 (3 H, t, J=7 Hz)

EXAMPLE 137

(3S)-3-[(2S)-5-Carboxy-2-{((6R)-5-tert-butoxycarbonyl-3-tert-butoxycarbonyl-4,5,6,7-tetrahydro-3H-imidazo[4,5-c]-pyridin-6-yl)carbonylamino}pentanoyl] oxyhexadecanamide NMR (CDCl₃, δ): 8.00 (1 H, s), 6.70 (1 H, br s), 5.85 (1 H, br s), 5.30 (1 H, br s), 5.20 (1 H, m), 4.42 (2 H, br s), 3.3 (1 H, m), 2.90 (2 H, m), 2.2–2.5 (4 H, m), 1.60 (9 H, s), 1.50 (9 H, s), 1.4–1.9 (8 H, m), 1.15–1.35 (22 H, m), 0.88 (3 H, t, J=7 Hz)

EXAMPLE 138

(3S)-3-[(2S)-5-Carboxy-2-{(2-pyridyl)methylamino}pentanoyl]oxyhexadecanamide

NMR (DMSO-d₆, δ): 8.45 (1 H, d, J=5 Hz), 7.72 (1 H, dd, J=7.5 Hz), 7.40 (1 H, d, J=10 Hz), 7.38 (1 H, br s), 6.84 (1 H, br s), 5.16 (1 H, m), 3.72 (2 H, ABq), 3.14 (1 H, br), 2.35 (2 H, m), 2.18 (2 H, br), 1.45–1.65 (6 H, m), 1.15–1.35 (22 H, m), 0.88 (3 H, t, J=7 Hz)

EXAMPLE 139

(3S)-3-[(2S)-5-Carboxy-2-{(5-imidazolyl)methylcarbonylamino}pentanoyl]oxyhexadecanamide NMR (DMSO-d₆, δ): 8.33 (1 H, d, J=10 Hz), 7.52 (1 H, s), 7.36 (1 H, br s), 6.83 (2 H, s), 5.08 (1 H, m), 4.16 (1 H, m), 3.40 (2 H, s), 2.1–2.4 (4 H, m), 1.4–1.7 (6 H, m), 1.15–1.35 (22 H, m), 0.84 (3 H, t, J=7 Hz)

EXAMPLE 140

(3S)-3-[(2S)-5-Carboxy-2-{(2-pyridyl)methylcarbonylamino}pentanoyl]oxyhexadecanamide NMR (CDCl₃, δ): 8.48 (1 H, d, J=5 Hz), 8.07 (1 H, d, J=10 Hz), 7.69 (1 H, t, J=7 Hz), 7.40 (1 H, d, J=7 Hz), 7.25 (1 H, t, J=7 Hz), 6.50 (1 H, br s), 6.15 (1 H, br s), 5.25 (1 H, m), 4.52 (1 H, m), 2.35–2.5 (4 H, m), 2.30 (2 H, t, J=7 Hz), 1.5–1.9 (6 H, m), 1.2–1.35 (22 H, m), 0.86 (3 H, t, J=7 Hz)

FAB-MS: 534 [M+H]

EXAMPLE 141

(3S)-3-[(2S)-5-Carboxy-2-(phenoxycarbonylamino)pentanoyl]oxyhexadecanenitrile

NMR (CDCl₃, δ): 7.06–7.41 (5 H, m), 5.92 (1 H, m), 5.06 (1 H, m), 4.43 (1 H, m), 2.32–2.82 (4 H, m), 1.56–2.12 (6 H, m), 1.04–1.42 (22 H, m), 0.88 (3 H, t, J=7 Hz)

EXAMPLE 142

(3S)-3-[(2S)-5-Carboxy-2-{3-((2S)-2-hydroxypropyl)ureido}pentanoyl]oxyhexadecanamide NMR (DMSO-d₆, δ): 7.35 (1 H, br s), 6.83 (1 H, br s), 6.34 (1 H, d, J=8 Hz), 6.05 (1 H, t, J=6 Hz), 5.07 (1 H, m), 4.07 (1 H, m), 3.56 (1 H, m), 2.98 (1 H, m), 2.85 (1 H, m), 2.34 (1 H, dd, J=15 Hz, 7 Hz), 2.27 (1 H, dd, J=15 Hz, 6 Hz), 2.18 (2 H, t, J=7 Hz), 1.37–1.70 (6 H, m), 1.10–1.32 (22 H, m), 0.99 (3 H, d, J=7 Hz), 0.85 (3 H, t, J=7 Hz)

EXAMPLE 143

(3S)-3-[(2S)-5-Carboxy-2-(3-morpholinoureido)pentanoyl]oxyhexadecanamide

NMR (DMSO-d₆, δ): 7.45 (1 H, br s), 7.38 (1 H, br s), 6.86 (1 H, br s), 6.58 (1 H, d, J=9 Hz), 5.08 (1 H, m), 4.10 (1 H, m), 3.64 (4 H, m), 2.68 (4 H, m), 2.32 (2 H, d, J=7 Hz), 2.18 (2 H, t, J=7 Hz), 1.06–1.80 (28 H, m), 0.85 (3 H, t, J=7 Hz)

EXAMPLE 144

(3R)-3-[(2R)-5-Carboxy-2-{3-(2-pyridyl)ureido}pentanoyl]oxyhexadecanamide

NMR (CDCl₃—CD₃OD(20:1), δ): 8.21 (1 H, d, J=5 Hz), 7.62 (1 H, dd, J=8 Hz, 7 Hz), 7.03 (1 H, d, J=8 Hz), 6.92 (1 H, dd, J=7 Hz, 5 Hz), 5.26 (1 H, m), 4.54 (1 H, dd, J=7 Hz, 6 Hz), 2.49 (2 H, d, J=7 Hz), 2.37 (2 H, m), 1.55–2.07 (6 H, m), 1.13–1.43 (22 H, m), 0.88 (3 H, t, J=7 Hz)

EXAMPLE 145

(3S)-3-[(2S)-5-Carboxy-2-{3-methyl-3-(2-pyridyl)ureido}pentanoyl]oxyhexadecanamide NMR (CDCl₃, δ): 8.33 (1 H, m), 7.71 (1 H, m), 6.98 (2 H, m), 6.81 (1 H, br s), 6.27 (1 H, br s), 5.28 (1 H, m), 4.60 (1 H, m), 3.39 (3 H, s), 2.28–2.60 (4 H, m), 1.53–2.07 (6 H, m), 1.12–1.38 (22 H, m), 0.88 (3 H, t, J=7 Hz)

EXAMPLE 146

(3S)-3-[(2S)-5-Carboxy-2-{3-(2-quinolyl)ureido}-pentanoyl]oxyhexadecanamide

NMR (CDCl₃, δ): 9.97 (1 H, s), 8.23 (1 H, d, J=8 Hz), 7.84 (1 H, d, J=7 Hz), 7.78 (1 H, d, J=8 Hz), 7.66 (1 H, dd, J=8 Hz, 7 Hz), 7.37–7.47 (2 H, m), 7.27 (1 H, d, J=8 Hz), 6.87 (1 H, br s), 5.16 (1 H, m), 4.36 (1 H, m), 2.39 (1 H, dd, J=15 Hz, 8 Hz), 2.33 (1 H, dd, J=15 Hz, 6 Hz), 2.26 (2 H, t, J=7 Hz), 1.45–1.94 (6 H, m), 1.09–1.39 (22 H, m), 0.84 (3 H, t, J=7 Hz)

EXAMPLE 147

(3S)-3-[(2S)-5-Carboxy-2-{3-(3-quinolyl)ureido}pentanoyl]oxyhexadecanamide

NMR (DMSO-d₆, δ): 9.15 (1 H, br s), 8.74 (1 H, d, J=2 Hz), 8.45 (1 H, d, J=2 Hz), 7.89 (1 H, d, J=8 Hz), 7.82 (1 H, d, J=8 Hz), 7.47–7.60 (2 H, m), 7.38 (1 H, br s), 6.81–6.90 (2 H, m), 5.15 (1 H, m), 4.21 (1 H, m), 2.18–2.39 (4 H, m), 1.43–1.82 (6 H, m), 1.02–1.34 (22 H, m), 0.84 (3 H, t, J=7 Hz)

EXAMPLE 148

(3S)-3-[(2S)-5-Carboxy-2-{(8-quinolyl)sulfonylamino}pentanoyl]oxyhexadecanamide

NMR (DMSO-d₆, δ): 9.04 (1 H, d, J=5 Hz), 8.50 (1 H, d, J=10 Hz), 8.26 (2 H, m), 7.65 (2 H, q, J=10 Hz), 7.22 (1 H, br s), 6.72 (1 H, br s), 4.72 (1 H, m), 4.15 (1 H, m), 2.0–2.2 (4 H, m), 1.4–1.8 (6 H, m), 0.9–1.3 (22 H, m), 1.88 (3 H, t, J=7 Hz)

The following compounds (Examples 149 and 150) were obtained according to a similar manner to that of Example 2.

EXAMPLE 149

(3R)-3-[(2R)-5-Benzyloxycarbonyl-2-(p-methoxybenzoylamino)pentanoyl]oxyhexadecanamide NMR (CDCl₃, δ): 7.78 (2 H, d, J=8 Hz), 7.28–7.41 (5 H, m), 6.94 (2 H, d, J=8 Hz), 6.85 (1 H, d, J=8 Hz) 5.98 (1 H, br s), 5.33 (2 H, m), 5.12 (2 H, s), 4.70 (1 H, m), 3.86 (3 H, s), 2.38–2.50 (4 H, m), 1.57–2.08 (6 H, m), 1.13–1.37 (22 H, m), 0.88 (3 H, t, J=7 Hz)

EXAMPLE 150

(3S)-N-Methyl-3-[(2S)-5-benzyloxycarbonyl-2-(p-methoxybenzoylamino)pentanoyl]oxyhexadecanamide NMR (CDCl$_3$, δ): 7.81 (2 H, d, J=8 Hz), 7.35 (5 H, m), 6.94 (2 H, d, J=8 Hz), 6.85 (1 H, d, J=7 Hz), 6.04 (1 H, m), 5.28 (1 H, m), 5.13 (2 H, s), 4.68 (1 H, m), 3.86 (3 H, s), 2.70 (3 H, d, J=5 Hz), 2.35–2.51 (4 H, m), 1.53–2.06 (6 H, m), 1.15–1.37 (22 H, m), 0.88 (3 H, t, J=7 Hz)

The following compounds (Examples 151 to 158) were obtained according to a similar manner to that of Example 27.

EXAMPLE 151

(3S)-3-[(2S)-5-Carboxy-2-{(6-methyl-2-pyridyl)carbonylamino}pentanoyl]oxyhexadecanamide NMR (CDCl$_3$, δ): 8.70 (1 H, d, J=10 Hz), 7.96 (1 H, d, J=10 Hz), 7.70 (1 H, t, J=10 Hz), 7.30 (1 H, d, J=10 Hz), 7.20 (1 H, br s), 6.26 (1 H, br s), 5.35 (1 H, m), 4.80 (1 H, m), 2.60 (3 H, s), 2.3–2.55 (4 H, m), 1.6–2.2 (6 H, m), 1.2–1.4 (22 H, m), 0.88 (3 H, t, J=7 Hz)

FAB-MS: 534 [M+H]

EXAMPLE 152

(3R)-3-[(2R)-5-Carboxy-2-{(3-quinolyl)carbonylamino}pentanoyl]oxyhexadecanamide

NMR (DMSO-d$_6$, δ): 9.29 (1 H, d, J=1.5 Hz), 9.10 (1 H, d, J=8 Hz), 8.87 (1 H, d, J=1.5 Hz), 8.10 (1 H, d, J=8 Hz), 8.09 (1 H, d, J=8 Hz), 7.88 (1 H, t, J=8 Hz), 7.70 (1 H, t, J=8 Hz), 7.35 (1 H, br s), 6.85 (1 H, br s), 5.15 (1 H, m), 4.42 (1 H, m), 2.19–2.45 (4 H, m), 1.45–1.98 (6 H, m), 1.07–1.40 (22 H, m), 0.84 (3 H, t, J=7 Hz)

EXAMPLE 153

N-[(S)-5-Carboxy-2-{(2-quinolyl)carbonylamino}pentanoyl]-N-(2-carbamoylethyl)tridecylamine NMR (CDCl$_3$, δ): 9.02·8.95 (1 H, d, J=8 Hz), 8.31 (1 H, d, J=8 Hz), 8.26·8.23 (sum 1 H, d, J=8 Hz), 8.18 (1 H, d, J=8 Hz), 7.88 (1 H, d, J=8 Hz), 7.78 (1 H, m), 7.62 (1 H, m), 7.04·6.84 (sum 1 H, br s), 6.71·6.54 (sum 1 H, m), 5.22 (1 H, m), 4.09 (1 H, m), 3.77·3.66 (sum 2 H, m), 3.34·3.15 (sum 2 H, m), 2.67 (1 H, m), 2.30–2.56 (3 H, m), 1.49–2.08 (4 H, m), 1.11–1.36 (22 H, m), 0.88 (3 H, t, J=7 Hz)

EXAMPLE 154

N-[(S)-5-Carboxy-2-{(2-quinolyl)carbonylamino}pentanoyl]-N-(N-methylcarbamoylmethyl)tridecylamine NMR (CDCl$_3$, δ): 8.89·8.83 (sum 1 H, d, J=7 Hz), 8.31·8.29 (sum 1 H, d, J=8 Hz), 8.23·8.21 (sum 1 H, d, J=8 Hz), 8.15 (1 H, d, J=8 Hz), 7.87 (1 H, m), 7.77 (1 H, m), 7.62 (1 H, m), 6.71 (1 H, m), 5.07·4.84 (sum 1 H, m), 4.16 (1 H, d, J=16 Hz), 3.96 (1 H, d, J=16 Hz), 3.62 (1 H, m), 3.47·3.22 (1 H, m), 2.87·2.80 (sum 3 H, d, J=5 Hz), 2.45 (2 H, m), 1.50–2.07 (4 H, m), 1.14–1.38 (22 H, m), 0.88 (3 H, m)

EXAMPLE 155

(3S)-3-[(2S)-5-Carboxy-2-{3-(5-chloro-2-pyridyl)ureido}pentanoyl]oxyhexadecanamide NMR (DMSO-d$_6$, δ): 9.37 (1 H, br s), 8.23 (1 H, d, J=2 Hz), 7.86 (1 H, d, J=7 Hz), 7.78 (1 H, dd, J=8 Hz, 2 Hz), 7.59 (1 H, d, J=8 Hz), 7.35 (1 H, br s), 6.84 (1 H, br s), 5.13 (1 H, m), 4.22 (1 H, m), 2.37 (1 H, dd, J=15 Hz, 8 Hz), 2.31 (1 H, dd, J=15 Hz, 6 Hz), 2.24 (2 H, t, J=7 Hz), 1.42–1.83 (6 H, m), 1.11–1.36 (22 H, m), 0.85 (3 H, t, J=7 Hz)

EXAMPLE 156

(3S)-3-[(2S)-5-Carboxy-2-{3-(5-methyl-2-pyridyl)ureido}pentanoyl]oxyhexadecanamide NMR (DMSO-d$_6$, δ): 9.18 (1 H, br s), 8.47 (1 H, br s), 8.02 (1 H, d, J=2 Hz), 7.50 (1 H, dd, J=8 Hz, 2 Hz), 7.35 (1 H, br s), 7.27 (1 H, d, J=8 Hz), 6.83 (1 H, br s), 5.13 (1 H, m), 4.25 (1 H, m), 2.37 (1 H, dd, J=15 Hz, 7 Hz), 2.31 (1 H, dd, J=15 Hz, 6 Hz), 2.25 (2 H, t, J=7 Hz), 2.19 (3 H, s), 1.43–1.85 (6 H, m), 1.12–1.34 (22 H, m), 0.85 (3 H, t, J=7 Hz)

EXAMPLE 157

(3S)-3-[(2S)-5-Carboxy-2-{3-(2-benzothiazolyl)ureido}-pentanoyl]oxyhexadecanamide NMR (DMSO-d$_6$, δ): 7.85 (1 H, d, J=8 Hz), 7.63 (1 H, d, J=8 Hz), 7.36 (2 H, m), 7.21 (2 H, m), 6.85 (1 H, br s), 5.15 (1 H, m), 4.26 (1 H, m), 2.38 (1 H, dd, J=15 Hz, 8 Hz), 2.33 (1 H, dd, J=15 Hz, 6 Hz), 2.25 (2 H, t, J=7 Hz), 1.45–1.85 (6 H, m), 1.09–1.34 (22 H, m), 0.84 (3 H, t, J=7 Hz)

EXAMPLE 158

(3S)-3-[(2S)-5-Carboxy-2-{3-(5-chloro-2-benzoxazolyl)ureido}pentanoyl]oxyhexadecanamide NMR (DMSO-d$_6$, δ): 8.68 (1 H, m), 7.62 (2 H, m), 7.37 (1 H, br s), 7.26 (1 H, dd, J=8 Hz, 2 Hz), 6.85 (1 H, br s), 5.16 (1 H, m), 4.34 (1 H, m), 2.32–2.42 (2 H, m), 2.27 (2 H, t, J=7 Hz), 1.47–1.88 (6 H, m), 1.11–1.36 (22 H, m), 0.84 (3 H, t, J=7 Hz)

EXAMPLE 159

To a solution of (3S)-3-[(2S)-5-carboxy-2-{(3-quinolyl)carbonylamino}pentanoyl]oxyhexadecanamide (100 mg) in methanol (10 ml) was added 2M solution of trimethylsilyl-diazomethane in hexane (2 ml) at room temperature. After being stirred at the same temperature for 2 days, the solvent was removed under reduced pressure and the resulting solid was triturated with ethyl ether to give (3S)-3-[(2S)-5-methoxycarbonyl-2-{(3-quinolyl)carbonylamino}pentanoyl]oxyhexadecanamide (68.4 mg).

NMR (DMSO-d$_6$, δ): 9.42 (1 H, d, J=5 Hz), 9.14 (1 H, d, J=10 Hz), 9.05 (1 H, m), 8.18 (2 H, t, J=7 Hz), 7.95 (1 H, t, J=7 Hz), 7.75 (1 H, t, J=7 Hz), 7.44 (1 H, br s), 6.85 (1 H, br s), 5.15 (1 H, m), 4.42 (1 H, m), 3.58 (3 H, s), 2.22–2.40 (4 H, m), 1.4–1.95 (6 H, m), 1.1–1.4 (22 H, m), 0.82 (3 H, t, J=7 Hz)

EXAMPLE 160

(3S)-3-[(2S)-5-Carboxy-2-{(3-quinolyl)carbonylamino}pentanoyl]oxyhexadecanamide (100 mg) was dissolved in 4N-hydrogen chloride in 1,4-dioxane (5 ml) at room temperature. After being stirred at the same temperature for 10 minutes, the solvent was removed under reduced pressure and the resulting solid was triturated with ethyl ether to give (3S)-3-[(2S)-5-carboxy-2-{(3-quinolyl)carbonylamino}pentanoyl]oxyhexadecanamide hydrochloride (100 mg).

NMR (DMSO-d$_6$, δ): 9.42 (1 H, d, J=5 Hz), 9.14 (1 H, d, J=10 Hz), 9.05 (1 H, m), 8.18 (2 H, t, J=7 Hz), 7.95 (1 H, t, J=7 Hz), 7.75 (1 H, t, J=7 Hz), 7.44 (1 H, br s), 6.85 (1 H, br s), 5.15 (1 H, m) , 4.42 (1 H, m), 2.22–2.40 (4 H, m), 1.4–1.95 (6 H, m), 1.1–1.4 (22 H, m), 0.82 (3 H, t, J=7 Hz)

EXAMPLE 161

To a solution of (3S)-3-[(2S)-5-carboxy-2-{(3-quinolyl)carbonylamino}pentanoyl]oxyhexadecanamide (100 mg) in 1,4-dioxane (5 ml) was added 1M aqueous sulfuric acid (0.18 ml) at room temperature. After being stirred at the same temperature for 10 minutes, the solvent was removed under reduced pressure and the resulting solid was triturated with ethyl ether to give (3S)-3-[(2S)-5-carboxy-2-{(3-quinolyl)carbonylamino}pentanoyl]oxyhexadecanamide sulfate (100 mg).

NMR (DMSO-$d_6$, δ): 9.42 (1 H, d, J=5 Hz), 9.14 (1 H, d, J=10 Hz), 9.05 (1 H, m), 8.18 (1 H, d, J=7 Hz), 8.14 (1 H, d, J=7 Hz), 7.95 (1 H, t, J=7 Hz), 7.75 (1 H, t, J=7 Hz), 7.44 (1 H, br s), 6.85 (1 H, br s), 5.15 (1 H, m), 4.42 (1 H, m), 2.22–2.40 (4 H, m), 1.4–1.95 (6 H, m), 1.1–1.4 (22 H, m), 0.82 (3 H, t, J=7 Hz)

EXAMPLE 162

To a solution of (3S)-3-[(2S)-5-carboxy-2-{(3-quinolyl)carbonylamino}pentanoyl]oxyhexadecanamide (100 mg) in 1,4-dioxane (5 ml) was added 1 N aqueous sodium hydroxide (0.18 ml) at room temperature. After being stirred at the same temperature for 10 minutes, the solvent was removed under reduced pressure and the resulting solid was triturated with ethyl ether to give sodium (3S)-3-[(2S)-5-carboxy-2-{(3-quinolyl)carbonylamino}pentanoyl]oxyhexadecanamide (100 mg).

NMR (DMSO-$d_6$, δ): 9.42 (1 H, d, J=5 Hz), 9.05 (1 H, m), 8.08 (2 H, d, J=7 Hz), 7.86 (1 H, t, J=7 Hz), 7.68 (1 H, t, J=7 Hz), 7.44 (1 H, br s), 6.90 (1 H, br s), 5.12 (1 H, m), 4.25 (1 H, m), 2.22–2.40 (2 H, m), 2.00 (2 H, m), 1.83 (2 H, m), 1.45–1.65 (4 H, m), 1.1–1.4 (22 H, m), 0.82 (3 H, t, J=7 Hz)

EXAMPLE 163

To a solution of (3S)-3-[(2S)-5-benzyloxycarbonyl-2-(tertiarybutoxycarbonylamino)pentanoyl]oxy-15-methylhexadecanamide (0.13 g) and anisole (0.2 g) in dichloromethane (10 ml) was added trifluoroacetic acid (2 ml). The mixture was stirred at room temperature for 30 minutes and evaporated. The residue was dissolved in ethyl acetate (10 ml) and washed with water, sodium bicarbonate aqueous solution and water. The solution was dried over magnesium sulfate. (S)-3-hydroxy-15-methylhexadecanoic acid (60 mg), 1-hydroxybenzotriazole (30 mg) and 1-ethyl-3-(3-dimethylaminopropyl)carbodiimide hydrochloride (42 mg) were added to the solution. The mixture was stirred at room temperature for 6 hours and poured into a mixture of ethyl acetate and diluted hydrochloric acid. The organic layer was washed with water, dried over magnesium sulfate and evaporated. The residue was chromatographed on a silica gel column eluting with a mixture of chloroform and methanol (50:1) to give (3S)-3-[(2S)-5-benzyloxycarbonyl-2-{(3S)-3-hydroxy-15-methylhexadecanoylamino}pentanoyl]oxy-15-methylhexadecanamide as an oil (0.10 g).

NMR (CDCl$_3$, δ): 7.35 (5 H, s), 6.55 (1 H, d, J=7 Hz), 5.82 (1 H, br s), 5.40 (1 H, br s), 5.26 (1 H, m), 5.10 (2 H, s), 4.53 (1 H, m), 3.98 (1 H, m), 3.52 (1 H, d, J=3 Hz), 2.3–2.5 (6 H, m), 1.1–1.9 (50 H, m), 0.87 (12 H, d, J=7 Hz)

EXAMPLE 164

To a solution of (3S)-3-[(2S)-5-benzyloxycarbonyl-2-{(3S)-3-hydroxy-15-methylhexadecanoylamino}pentanoyl]oxy-15-methylhexadecanamide (80 mg) in a mixture of 1,4-dioxane (10 ml) and methanol (10 ml) were added 10% palladium on active carbon (50 mg) and water (1 ml). The mixture was stirred at room temperature under hydrogen atmosphere for 1 hour. The catalyst was filtered off and the solvent was removed under reduced pressure to give (3S)-3-[(2S)-5-carboxy-2-{(3S)-3-hydroxy-15-methylhexadecanoylamino}-pentanoyl]oxy-15-methylhexadecanamide as white powder (56 mg).

NMR (CD$_3$OD, δ): 5.26 (1 H, m), 4.38 (1 H, m), 3.95 (1 H, m), 2.3–2.6 (6 H, m), 1.1–1.9 (50 H, m), 0.89 (12 H, d, J=7 Hz)

What is claimed is:

1. A fatty acid compound having the formula:

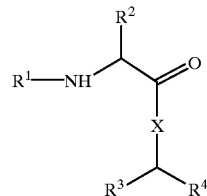

wherein $R^1$ is acyl or lower aliphatic hydrocarbon which is substituted by quinolyl or isoquinolyl;
$R^2$ is acyl(lower)alkyl;
$R^3$ is alkyl;
$R^4$ is acyl or acyl(lower)alkyl; and
X is —O— or —N($R^5$)—;
wherein $R^5$ is hydrogen or acyl(lower)alkyl; or a pharmaceutically acceptable salt thereof.

2. The compound of claim 1, wherein:
$R^1$ is acyl, which is lower alkanoyl, higher alkanoyl, lower alkenoyl, higher alkenoyl, each of which are optionally substituted.

3. The compound of claim 2, wherein said lower alkanoyl which is optionally substituted comprises formyl, acetyl, proprionyl, butyryl, isobutyryl, valeryl, hexanoyl, or pivaloyl, which are each optionally substituted by halogen, hydroxy, lower alkoxy, amino, protected amino di (lower) alkylamino, lower alkoxyamino, or (lower) alkoxyamino.

4. The compound of claim 2, wherein said higher alkanoyl which is optionally substituted comprises heptanoyl, octanoyl, nonanoyl, decanoyl, undecanoyl, lauroyl, tridecanoyl, myristoyl, pentadecanoyl, palmitoyl, 14-methylpentadecanoyl, 15-methylhexadecanoyl, 10,12-dimethyltetradecanoyl, heptadecanoyl, stearoyl, nonadecanoyl or icosanoyl, which are each optionally substituted by halogen, hydroxy, lower alkoxy, amino, protected amino, de (lower) alkylamino, lower alkoxyamino, or (lower) alkoxyamino.

5. The compound of claim 2, wherein said lower alkanoyl which is optionally substituted comprises acryloyl, crotonoyl, isocrotonoyl, methacryloyl, 3-pentenoyl, 2,4-pentadienoyl, 5-hexenoyl or 2,4-hexadienoyl, which are each optionally substituted by halogen, hydroxy, lower alkoxy, amino, protected amino, di (lower) alkylamino, lower alkoxyamino, or (lower) alkoxyamino.

6. The compound of claim 2, wherein said high alkanoyl, which is optionally substituted comprises 4-heptenoyl, 3-octenoyl, 3,6-decadienoyl, 3,7,11-trimethyl-2,6,10-dodecatrienoyl or 4,10 heptadecadienoyl, which are each optionally substituted by halogen, hydroxy, lower alkoxy, amino, protected amino, di (lower) alkylamino, lower alkoxyamino, or (lower) alkoxyamino.

7. The compound of claim 1, wherein $R^3$ is higher alkyl of at least 7 carbons.

8. The compound of claim 1, wherein X is —O—.

9. The compound of claim 1, which is (3S)-3-[(2S)-5-carboxy-2-{(2-quinolyl) carbonylamino}-pentanoyl] oxyhexadecanamide.

10. A process for the preparation of the fatty acid derivative of claim 1 or a salt thereof, which comprises 1) reacting the compound of the formula

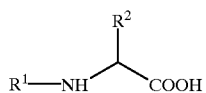

wherein $R^1$ and $R^2$ are each as defined in claim 1, or a salt thereof, with the compound of the formula:

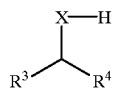

wherein $R^3$, $R^4$ and X are each as defined in claim 1, or a salt thereof;

2) reacting the compound of the formula:

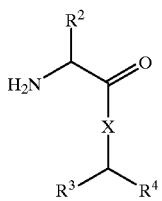

wherein $R^2$, $R^3$, $R^4$ and X are each as defined in claim 1, or a salt thereof, with the compound of the formula:

wherein $R_a^1$ is acyl group,
or a salt thereof, to give the compound of the formula:

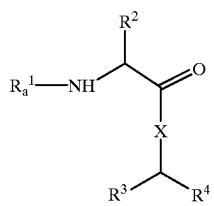

wherein $R^2$, $R^3$, $R^4$ and X are each as defined in claim 1; and
$R_a^1$ is as defined above, or a salt thereof, 3) reacting the compound of the formula:

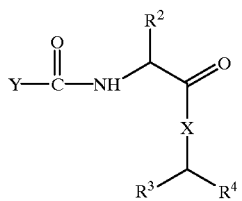

wherein $R^2$, $R^3$, $R^4$ and X are each as defined in claim 1; and
Y is a leaving group; or a salt thereof, with an amidating agent, to give the compound of the formula:

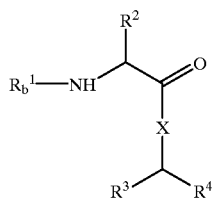

wherein $R^2$, $R^3$, $R^4$ and X are each as defined in claim 1; and $R_b^1$ is amidated carboxy or a salt thereof, 4) subjecting the compound of the formula:

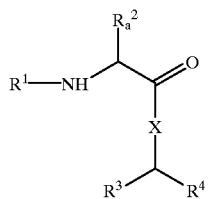

wherein $R^1$, $R^3$, $R^4$ and X are each as defined in claim 1; and
$R_a^2$ is protected carboxy(lower)alkyl,
or a salt thereof, to an elimination reaction of the carboxy protective group, to give the compound of the formula:

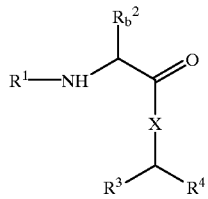

wherein $R^1$, $R^3$, $R^4$ and X are each as defined in claim 1; and $R_b^2$ is carboxy(lower)alkyl, or a salt thereof, 5) reacting the compound of the formula:

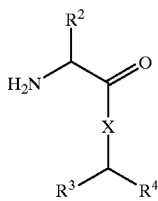

wherein $R^2$, $R^3$, $R^4$ and X are each as defined in claim 1, or a reactive variation thereof at the amino group or a salt thereof, with a lower aliphatic hydrocarbon compound substituted with oxo which optionally has one or more substituent(s) in the presence of a reducing agent, to give the compound of the formula:

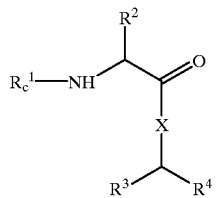

wherein $R^2$, $R^3$, $R^4$ and X are each as defined above, and $R_c^1$ is lower aliphatic hydrocarbon group which optionally has one or more substituent(s), or a salt thereof, 6) reacting the compound of the formula:

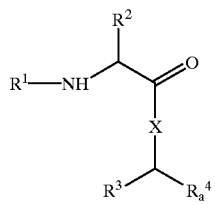

wherein $R^1$, $R^2$, $R^3$ and X are each as defined in claim 1; and $R_a^4$ is carboxy or carboxy(lower)alkyl, or a salt thereof, with an amidating agent, to give the compound of the formula:

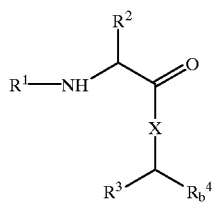

wherein $R^1$, $R^2$, $R^3$ and X are each as defined in claim 1; and $R_a^4$ is amidated carboxy or amidated carboxy(lower)alkyl, or a salt thereof, or 7) reacting the compound of the formula:

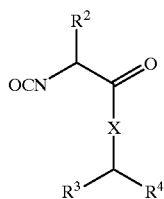

wherein $R^2$, $R^3$, $R^4$ and X are each as defined in claim 1; or a salt thereof, with an amidating agent, to give the compound of the formula:

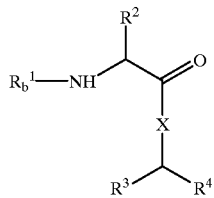

wherein $R^2$, $R^3$, $R^4$ and X are each as defined in claim 1, or a salt thereof.

11. A pharmaceutical composition, which comprises, as an active ingredient, the fatty acid compound of claim 1, or a pharmaceutically acceptable salt thereof in admixture with a pharmaceutically acceptable carrier.

12. A method for inhibiting phospholipase A2, which comprises administering an effective amount of the compound of claim 1, or a pharmaceutically acceptable salt thereof to a patient in need thereof.

* * * * *